(12) United States Patent
Elson et al.

(10) Patent No.: US 8,029,794 B2
(45) Date of Patent: Oct. 4, 2011

(54) COMBINING THERAPIES TARGETING MULTIPLE TOLL-LIKE RECEPTORS

(75) Inventors: Greg Elson, Collonges sous Saleve (FR); Olivier Leger, St. Sixt (FR)

(73) Assignee: Novimmune S.A., Geneva (CH)

( * ) Notice: Subject to any disclaimer, the term of this patent is extended or adjusted under 35 U.S.C. 154(b) by 0 days.

(21) Appl. No.: 11/301,373

(22) Filed: Dec. 12, 2005

(65) Prior Publication Data

US 2006/0165686 A1 Jul. 27, 2006

Related U.S. Application Data

(60) Provisional application No. 60/635,421, filed on Dec. 10, 2004.

(51) Int. Cl.
*A61K 39/395* (2006.01)
(52) U.S. Cl. ................ 424/143.1; 424/130.1; 424/141.1
(58) Field of Classification Search ........................ None
See application file for complete search history.

(56) References Cited

U.S. PATENT DOCUMENTS

| 6,444,206 | B1 | 9/2002 | Leturcq | 424/141.1 |
| 7,271,248 | B2 * | 9/2007 | Hardiman et al. | 530/387.1 |
| 7,312,320 | B2 | 12/2007 | Elson | 530/388.2 |
| 2005/0265998 | A1 * | 12/2005 | Elson | 424/143.1 |
| 2008/0118514 | A1 | 5/2008 | Elson | 424/143.1 |

FOREIGN PATENT DOCUMENTS

| WO | WO 03/013440 | 2/2003 |
| WO | WO 2005/028509 | 3/2005 |
| WO | WO 2005/047330 | 5/2005 |

OTHER PUBLICATIONS

Meng et al. The Journal of Clinical Investigation 2004, 113:1473-1481.*
Strom et al. (in Therapeutic Immunology, Austen et al. (Ed.) Blackwell Science, Cambridge MA, 1996; see pp. 451-456).*
Akashi et al., "Cutting edge: Cell surface expression and lipopolysaccharide signaling via the Toll-like receptor 4-MD-2 complex on mouse peritoneal macrophages," J. Immunol., vol. 164(7): 3471-3475 (2000).
Akashi et al., "Lipopolysaccharide interaction with cell surface Toll-like receptor 4-MD-2: Higher affinity than that with MD-2 or CD14," J. Exp. Med., vol. 198(7): 1035-1042 (2003).
Akira et al., "Toll-like receptor signaling," Nature Reviews Immunology, vol. 4: 491-511 (2004).
Backhed et al, "TLR4-dependent recognition of lipopolysaccharide by epithelial cells requires sCD14," Cellular Microbiology, vol. 4(8): 493-501 (2002).
Buell et al., "Blockade of human P2X7 receptor function with a monoclonal antibody." Blood 92: 3521-3528 (1998).
Devaney et al., "Neutrophil elastase up-regulates interleukin via toll-like receptor 4," FEBS Letters, vol. 544 (1-3): 129-132 (2003).
GenBank Accession No. AAH20690.1 "Lymphocyte antigen 96 [*Homo sapiens*]".

GenBank Accession No. BAA78717.1 "MD-2 [*Homo sapiens*]".
GenBank Accession No. CAH72619.1 "toll-like receptor 4 [*Homo sapiens*]".
GenBank Accession No. CAH72620 "toll-like receptor 4 [*Homo sapiens*]".
GenBank Accession No. NP_003254.2 "toll-like receptor 1 [*Homo sapiens*]".
GenBank Accession No. NP_003255.2 "toll-like receptor 2 [*Homo sapiens*]".
GenBank Accession No. NP_003259.2 "toll-like receptor 5 [*Homo sapiens*]".
GenBank Accession No. NP_006059.2 "toll-like receptor 6 [*Homo sapiens*]".
GenBank Accession No. NP_056179, "MD-2 protein [*Homo sapiens*]".
GenBank Accession No. Q9Y6Y9, "RecName: Full=Lymphocyte antigen 96; AltName: Full=Protein MD-2; AltName: Full=ESPO-1; Flags: Precursor".
Ishida et al., "Hypoxia diminishes Toll-like Receptor 4 expression through reactive oxygen species generated by mitochondria in endothelial cells," J. Immunol., vol. 169(4): 2069-2075 (2002).
Johnson et al., "Activation of mammalian Toll-like receptors by endogenous agonists" Crit. Rev. Immunol., 23(1-2):15-44 (2003).
Jones and Bendig, "Rapid PCR-cloning of full-length mouse immunoglobulin variable regions." Biotechnology (N.Y.), 9: 88-89 (1991).
Kammann et al., "Rapid insertional mutagenesis of DNA by polymerase chain reaction (PCR)," Nucleic Acids Res.. vol. 17: 5404 (1989).
Kawasaki et al., "Identification of mouse MD-2 residues important for forming the cell surface TLR4-MD-2 complex recognized by anti-TLR4-MD2 antibodies, and for conferring LPS and taxol responsiveness on mouse TLR4 by alanine-scanning mutagenesis," J. Immunol., vol. 170(1): 413-420 (2003).
Kirkland et al., "Analysis of Lipopolysaccharide Binding by CD14," J. Biol. Chem., vol. 268(33): 24818-24823(1993).
Kolbinger et al., "Humanization of a mouse anti-human IgE antibody: a potential therapeutic for IgE-mediated allergies" Protein Eng. 6, 971-980, 1993).
Lakhani et al., "Toll-like receptor signaling in sepsis" Curr. Opin. Pediatr. 15: 278-282 (2003).
Lenhardt et al., "Activation of innate immunity in the CNS triggersneurodegeneration through a Toll-like receptor 4-dependent pathway," PNAS, vol. 100(14): 8514-8519 (2003).
Medzhitov et al., Nature, "A human homologue of the *Drosophila* Toll protein signals activation of adaptive immunity," vol. 388(6640):394-7 (1997).

(Continued)

*Primary Examiner* — Sharon Wen
(74) *Attorney, Agent, or Firm* — Mintz Levin Cohn Ferris Glovsky and Popeo, P.C.; Ivor R. Elrifi

(57) ABSTRACT

The invention relates generally to compositions that contain multiple antibodies, e.g., multiple neutralizing antibodies, that immunospecifically bind to one or more toll-like receptors, e.g., two or more toll-like receptors, and methods of using these compositions in the treatment of inflammatory disorders.

6 Claims, 24 Drawing Sheets

OTHER PUBLICATIONS

Meng et al., "Antagonistic antibody prevents toll-like receptor 2-driven lethal shock-like syndromes," J. Clin. Invest., vol. 113: 1473-1481 (2004).

Miyake, "Endotoxin recognition molecules MD-2 and Toll-like Receptor 4 as potential targets for therapeutic intervention of endotoxin shock," Current Drug Targets: Inflammation and Allergy, vol. 3(3): 291-297 (2004).

Miyake, "Innate recognition of lipopolysaccharide by CD14 and toll-like receptor 4-MD-2: unique roles for MD-2," International Immunopharmacology, vol. 3(1): 1199-128 (2003).

Mizel et al., "Induction of macrophage nitric oxide production by gram-negative flagellin involves signaling via heteromeric toll-like receptor 5/toll-like receptor 4 complexes," J. Immunol., vol. 170: 6217-3223 (2003).

Nijhuis et al, "Endothelial cells are main producers of Interleukin 8 through Toll-like receptor 2 and 4 signaling during bacterial infection in leukopenic cancer patients," Clinical and Diagnostic Laboratory Immunology, vol. 10(4): 558-563 (20030.

O'Neill, "Therapeutic targeting of Toll-like receptors for inflammatory and infectious diseases" Curr. Opin. Pharmacol. 3: 396-403 (2003).

Ohashi et al., "Cutting Edge: Heat Shock Protein 60 is a Putative Endogenous Ligand of the Tdl-Like Receptor-4 Complex," J. Immunol., vol. 164: 558-561 (2000).

Okamura et al., "The Extra Domain A of Fibronectin Activates Toll-like Receptor 4," J. Biol. Chem. vol. 276(13): 10229-10233 (2001).

Pasterkamp et al., "Role of Toll-like Receptor 4 in the initiation and progression of atherosclerotic disease," Eur. J. Clin. Invest., vol. 34(5): 328-334 (2004).

Pivarcsi et al., "Expression and Function of Toll-like Receptors 2 and 4 in Human Keratinocytes," International Immunology, vol. 15(6): 721-730 (2003).

Pugin et al., "Soluble MD-2 activity in plasma from patients with severe sepsis and septic shock," Blood, vol. 104(13): 4071-4079 (2004).

Rock et al., "A family of human receptors structurally related to *Drosophila* Toll," Proc. Natl. Acad. Sci. USA, vol. 95: 588-593 (1998).

Santa Cruz Biotechnology, Inc., "TLR (H-80): sc-10741", catalog page for TLR4 (H-80), a rabbit polyclonal antibody raised against amino acids 242-321 of TLR4 of human origin.

Sato et al., "Reshaping a human antibody to inhibit the interleukin 6-dependent tumor cell growth," Cancer Res. vol. 53: 851-856 (1993).

Shimazu et al., "MD-2, a molecule that confers lipopolysaccharide responsiveness on Toll-like receptor 4," J. Exp. Med., vol. 189(11): 1777-1782 (1999).

Takeda et al., "Toll-like receptors" Annu. Rev. Immunol., 21: 335-76 (2003).

Uehori et al., "Simultaneous blocking of human Toll-like receptors 2 and 4 suppresses myeloid dendritic cell activation induced by *Mycobacterium bovis* bacillus Calmette-Guérin peptidoglycan," Infect. Immun., vol. 71(8): 4238-4249 (2003).

Weingarten et al., "Interactions of lipopolysaccharide with neutrophils in blood via CD14," J. Leukocyte Biol., vol. 53: 518-524 (1993).

Yang et al., "Cellular events mediated by lipopolysaccharide-stimulated Toll-like receptor 4," J. Biol. Chem., vol. 275(27): 20861-20866 (2000).

* cited by examiner

A

B

B

A

B

C

D

C
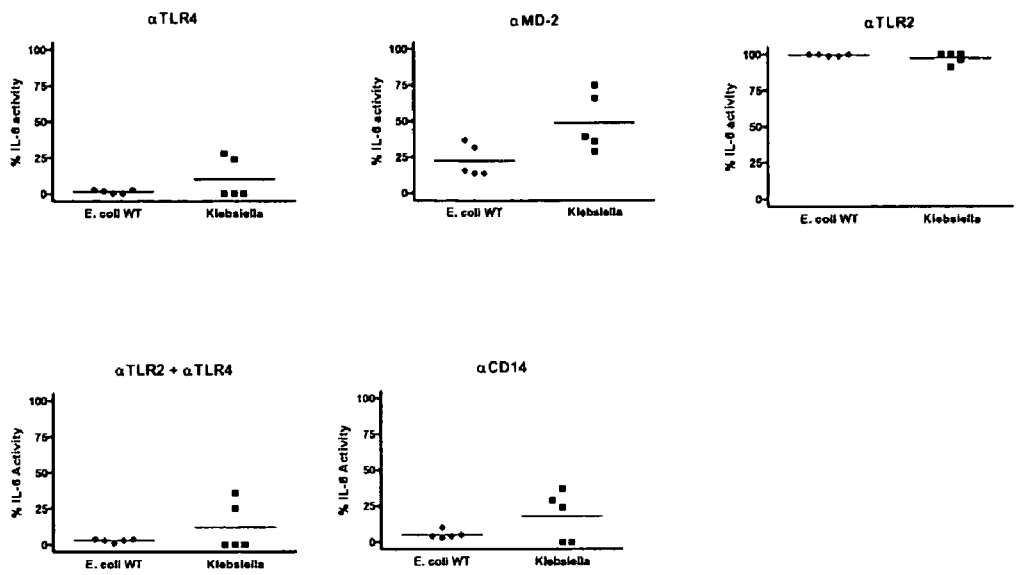
D
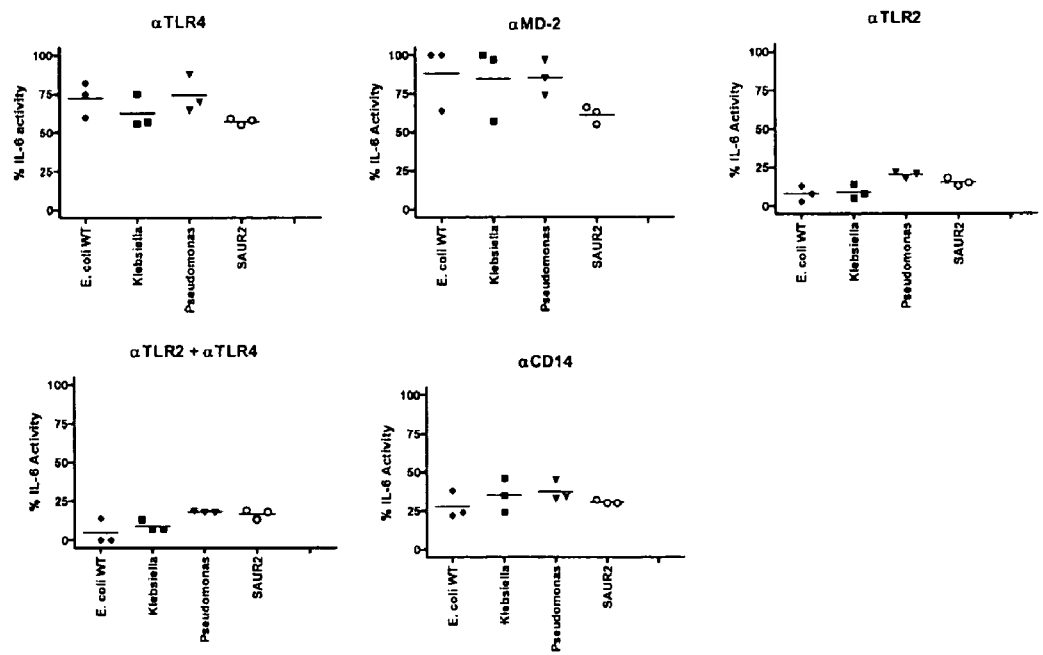

E. coli WT

Klebsiella

Pseudomonas

SAUR2

Figure 10A: 18H10 VH nucleotide sequence

```
  1 caggtgcaac tgcagcagtc tggggctgat cttgtgaggc cagggcctt
      q  v  q   l  q  q  s   g  a  d   l  v  r   p  g  a
 51 agtcaagttg tcctgcacag cttctggctt caacattaaa gactcctata
      l  v  k   l  s  c   t  a  s  g   f  n  i  k   d  s  y
101 tacactgggt gaagaagagg cctgaatggg gcctggagtg gattggatgg
      i  h  w   v  k  k  r   p  e  w   g  l  e  w   i  g  w
151 actgatcctg agaatgttaa ttctatatat gacccgaggt tcagggcaa
      t  d  p   e  n  v  n   s  i  y   d  p  r   f  q  g
201 ggccagtata acagcagaca catcctccaa cacagccttc cttcagctca
      k  a  s  i   t  a  d   t  s  s   n  t  a  f   l  q  l
251 ccagcctgac atctgaggac actgccgtct attactgtgc taggggttat
      t  s  l   t  s  e  d   t  a  v   y  y  c   a  r  g  y
301 aacggtgttt actatgctat ggactactgg ggccaaggga cctcagtcac
      n  g  v   y  y  a   m  d  y  w   g  q  g   t  s  v
351 cgtctcctca (SEQ ID NO:1)
      t  v  s  s  (SEQ ID NO:2)
```

Figure 10B: 18H10 VH protein sequence

```
  1 qvqlqqsgad lvrpgalvkl sctasgfnik dsyihwvkkr pewglewigw
 51 tdpenvnsiy dprfqgkasi tadtssntaf lqltsltsed tavyycargy
101 ngvyyamdyw gqgttvtvss (SEQ ID NO:2)
```

Figure 10C: 18H10 VH CDR protein sequences dsyih (SEQ ID NO:3)
wtdpenvnsiydprfqg (SEQ ID NO:4)
gyngvyyamdy (SEQ ID NO:5)

Figure 10D: 18H10 VL nucleotide sequence

```
  1 caaattgttc tcacccagtc tccatcaatc atgtctgcgt ctctagggga
      q  i  v   l  t  q   s  p  s  i   m  s  a   s  l  g
 51 ggagatcacc ctaacctgca gtgccagctc gagtgtaatt tacatgcact
      e  e  i  t   l  t  c   s  a  s   s  v  i   y  m  h
101 ggtaccagca gaagtcaggc acttctccca aactcttgat ttataggaca
      w  y  q   q  k  s  g   t  s  p   k  l  l   i  y  r  t
151 tacaacctgg cttctggagt cccttctcgc ttcagtggca gtgggtctgg
      y  n  l   a  s  g   v  p  s  r   f  s  g   s  g  s
201 gacctttat tctctcacaa tcagcagtgt ggaggctgaa gatgctgccg
      g  t  f  y   s  l  t   i  s  s   v  e  a   e  d  a  a
251 attattactg ccatcagtgg agtagttttc cgtacacgtt cggaggggg
      d  y  y   c  h  q  w   s  s  f   p  y  t   f  g  g  g
301 accaagctgg aaatcaaacg g (SEQ ID NO:6)
      t  k  l   e  i  k   r  (SEQ ID NO:7)
```

Figure 10E: 18H10 VL protein sequence

```
  1 qviltqspsi msaslgeeit ltcsasssvi ymhwyqqksg tspklliyrt
 51 ynlasgvpsr fsgsgsgtfy sltissveae daadyychqw ssfpytfggg
101 tkleikr (SEQ ID NO:7)
```

Figure 10F: 18H10 VL CDR protein sequences sasssviymh (SEQ ID NO:8)
rtynlas (SEQ ID NO:9)
hqwssfpyt (SEQ ID NO:10)

Figure 11A: 16G7 VH nucleotide sequence

```
1    aggtgaaact gcaggagtct ggagctgagc tgatgaagcc tggggcctca
      v  k  l   q  e  s    g  a  e   l  m  k    p  g  a  s
51   gtgaagatat cctgcaaggc tactggctac aaattcagtg actactggat
      v  k  i   s  c  k    a  t  g  y  k  f  s   d  y  w
101  agagtggata aaacagaggc ctggacatgg ccttgagtgg attggagaga
      i  e  w  i  k  q  r    p  g  h    g  l  e  w    i  g  e
151  ttttgcctgg aagtggtagt actaactaca atgaggactt caaggacaag
      i  l  p   g  s  g  s    t  n  y   n  e  d    f  k  d  k
201  gccacattca cttcagatac atcctccaac acagcctaca tgcaactcag
       a  t  f   t  s  d    t  s  s  n   t  a  y   m  q  l
251  cagcctgaca tctgaagact ctgccgtcta ttactgtgca aaagaggaga
      s  s  l  t    s  e  d    s  a  v   y  y  c  a    k  e  e
301  gggcgtacta ctttggctat tggggccaag ggaccacggt caccgtctcc
       r  a  y  y  f  g  y    w  g  q   g  t  t   v  t  v  s
351  tca (SEQ ID NO:11)
      s  (SEQ ID NO:12)
```

Figure 11B: 16G7 VH protein sequence

```
1    qvqlqqsgaelmkpgasvkisckatgykfs dywie wikqrpghglewige
51   ilpgsgstnynedfkd katftsdtssntaymqlssltsedsavyycak ee
101  rayyfgy wgqgttvtvss (SEQ ID NO:12)
```

Figure 11C: 16G7 VH CDR protein sequences dywie (SEQ ID NO:13)
eilpgsgstnynedfkd (SEQ ID NO:14)
eerayyfgy (SEQ ID NO:15)

Figure 11D: 16G7 VL nucleotide sequence

```
1    gatgttttga tgacccaaac tccactctcc ctgcctgtca gtcttggaga
       d  v  l   m  t  q    t  p  l  s    l  p  v   s  l  g
51   tcaagcctcc atctcttgca ggtctagtca gagccttgaa aacagtaatg
      d  q  a   s  i  c    r  s  s    q  s  l  e  n  s  n
101  gaaacaccta tttgaactgg tacctccaga aaccaggcca gtctccacag
       g  n  t   y  l  n  w    y  l  q    k  p  g  q  s  p  q
151  ctcctgatct acagggtttc aaccgatttt ctggggtcc tagacaggtt
       l  l  i   y  r  v   s  n  r  f    s  g  v    l  d  r
201  cagtggtagt ggatcaggga cagatttcac actgaaaatc agcagagtgg
       f  s  g  s    g  s  g   t  d  f    t  l  k  i    s  r  v
251  aggctgagga tttgggagtt tatttctgcc tccaagttac acatgtccct
      e  a  e   d  l  g  v    y  f  c    l  q  v   t  h  v  p
301  cccacgttcg gtgctgggac caagctggaa ctgaaacgg (SEQ ID NO:16)
       p  t  f   g  a  g   t  k  l  e   l  k  r (SEQ ID NO:17)
```

Figure 11E: 16G7 VL protein sequence

```
1    dvvmtqtplslpvslgdqasisc rssqslensngntyln wylqkpgqspq
51   lliy rvsnrfs gvldrfsgsgsgtdftlkisrveaedlgvyfc lqvthvp
101  pt fgagtklelkr (SEQ ID NO:17)
```

Figure 11F: 16G7 VL CDR protein sequences rssqslensngntyln (SEQ ID NO:18)
rvsnrfs (SEQ ID NO:19)
lqvthvppt (SEQ ID NO:20)

Figure 12A: 15C1 VH nucleotide sequence

```
1   gatgtgcagc ttcaggagtc aggacctgac ctaatacaac cttctcagtc actttcactc acctgcactg
     d   v   q   l   q   e   s   g   p   d   l   i   q   p   s   q   s   l   s   l   t   c   t
71  tcactggcta ctccatcacc ggtggttata gctggcactg gatccggcag tttccaggaa acaaactgga
     v   t   g   y   s   i   t   g   g   y   s   w   h   w   i   r   q   f   p   g   n   k   l
141 atggatgggc tacatccact acagtggtta cactgacttc aacccctctc tcaaaactcg aatctctatc
     e   w   m   g   y   i   h   y   s   g   y   t   d   f   n   p   s   l   k   t   r   i   s   i
211 actcgagaca catccaagaa ccagttcttc ctgcagttga attctgtgac tactgaagac acagccacat
     t   r   d   t   s   k   n   q   f   f   l   q   l   n   s   v   t   t   e   d   t   a   t
281 attactgtgc aagaaaagat ccgtccgacg gatttcctta ctggggccaa gggactctgg tcactgtctc
     y   y   c   a   r   k   d   p   s   d   g   f   p   y   w   g   q   g   t   l   v   t   v
351 tgca (SEQ ID NO:21)
     s   a (SEQ ID NO:22)
```

Figure 12B: 15C1 VH protein sequence

```
1   dvqlqesgpd liqpsqslsl tctvtgysit ggyswhwirq fpgnklewmg
51  yihysgytdf npslktrisi trdtsknqff lqlnsvtted tatyycarkd
101 psdgfpywgq gtlvtvsa (SEQ ID NO:22)
```

Figure 12C: 15C1 VH CDR protein sequences

```
ggyswh (SEQ ID NO:23)
yihysgytdfnpslkt (SEQ ID NO:24)
kdpsdgfpy (SEQ ID NO:25)
```

Figure 12D: 15C1 VL nucleotide sequence

```
1   gacattgtga tgacccagtc tccagccacc ctgtctgtga ctccaggtga tagagtctct
     d   i   v   m   t   q   s   p   a   t   l   s   v   t   p   g   d   r   v   s
61  ctttcctgca gggccagcca gagtatcagc gaccacttac actggtatca acaaaaatca
     l   s   c   r   a   s   q   s   i   s   d   h   l   h   w   y   q   q   k   s
121 catgagtctc cacggcttct catcaaatat gcttccatg ccatttctgg gatcccctcc
     h   e   s   p   r   l   l   i   k   y   a   s   h   a   i   s   g   i   p   s
181 aggttcagtg gcagtggatc agggacagat ttcactctca gcatcaaaag tgtggaacct
     r   f   s   g   s   g   s   g   t   d   f   t   l   s   i   k   s   v   e   p
241 gaagatattg gggtgtatta ctgtcaaaat ggtcacagtt ttccgctcac gttcggtgct
     e   d   i   g   v   y   y   c   q   n   g   h   s   f   p   l   t   f   g   a
301 gggaccaagc tggagctgaa a (SEQ ID NO:26)
     g   t   k   l   e   l   k (SEQ ID NO:27)
```

Figure 12E: 15C1 VL protein sequence

```
1   divmtqspat lsvtpgdrvs lscrasqsis dhlhwyqqks hesprlliky
51  ashaisgips rfsgsgsgtd ftlsiksvep edigvyycqn ghsfpltfga
101 gtklelkr (SEQ ID NO:27)
```

Figure 12F: 15C1 VL CDR protein sequences

```
rasqsisdhlh (SEQ ID NO:28)
yashais (SEQ ID NO:29)
qnghsfplt (SEQ ID NO:30)
```

Figure 13A: 7E3 VH nucleotide sequence

```
1   caggttactc tgaaagagtc tggccctggg atattgcagc cctcccagac cctcagtctg acttgttctt
      q  v  t   l  k  e   s  g  p   g  i  l   q  p  s  q   t  l  s  l   t  c  s
71  tctctgggtt ttcactgacc acttataata taggagtagg ctggattcgt cagccttcag ggaagggtct
      f  s  g   f  s  l  t  t  y  n   i  g  v   g  w  i  r   q  p  s   g  k  g
141 ggagtggctg gcacacattt ggtggaatga taatatttac tataatacag tccttaagag ccgactcaca
      l  e  w  l   a  h  i   w  w  n   d  n  i  y   y  n  t   v  l  k   s  r  l  t
211 ttctccaagg ataccccaa caaccaggtt ttcctcaaga tcgccagtgt ggacattgca gatactgcca
      f  s  k   d  t  s   n  n  q  v   f  l  k   i  a  s   v  d  i  a   d  t  a
281 catattactg tattcgaatg gctgagggaa ggtacgacgc tatggactac tggggtcaag gaacctcagt
      t  y  y   c  i  r  m   a  e  g   r  y  d   a  m  d  y   w  g  q   g  t  s
351 caccgtctcc tca (SEQ ID NO:31)
      v  t  v  s   s (SEQ ID NO:32)
```

Figure 13B: 7E3 VH protein sequence

```
1    qvtlkesgpg ilqpsqtlsl tcsfsgfslt tynigvgwir qpsgkglewl
51   ahiwwndniy yntvlksrlt fskdtsnnqv flkiasvdia dtatyycirm
101  aegrydamdy wgqgtsvtvs s (SEQ ID NO:32)
```

Figure 13C: 7E3 VH CDR protein sequences tynigvg (SEQ ID NO:33)
hiwwndniyyntvlks (SEQ ID NO:34)
maegrydamdy (SEQ ID NO:35)

Figure 13D: 7E3 VL nucleotide sequence

```
1   gctatccaga tgacacagag tacatcctcc ctgtctgcct ctctgggaga cagagtcacc atcaattgca
      a  i  q   m  t  q   s  t  s  s   l  s  a   s  l  g   d  r  v  t   i  n  c
71  gggcaagtca ggacatcacc aattatttaa attggtatca gcagaaacca gatggaactg tcagactcct
      r  a  s   q  d  i  t   n  y  l   n  w  y   q  q  k  p   d  g  t   v  r  l
141 gatctattat acatcaaaat tacactcagg agccccatca aggttcagtg gccgtgggtc tggaacagat
      l  i  y  y   t  s  k   l  h  s   g  a  p  s   r  f  s   g  r  g   s  g  t  d
211 tattctctca ccattagtaa cctggagcaa gaggatattg ccacttactt ttgccaacag ggtaatacgt
      y  s  l   t  i  s   n  l  e  q   e  d  i   a  t  y   f  c  q  q   g  n  t
281 ttccgtggac gttcggtgga ggcaccaaac tggaaatcaa acgt (SEQ ID NO: 36)
      f  p  w   t  f  g  g   g  t  k   l  e  i   k  r (SEQ ID NO:37)
```

Figure 13E: 7E3 VL protein sequence

```
1    aiqmtqstss lsaslgdrvt incrasqdit nylnwyqqkp dgtvrlliyy
51   tsklhsgaps rfsgrsgtd ysltisnleq ediatyfcqq gntfpwtfgg
101  gtkleikr (SEQ ID NO:37)
```

Figure 13F: 7E3 VL CDR protein sequences rasqditnyln (SEQ ID NO:38)
ytsklhs (SEQ ID NO:39)
qqgntfpwt (SEQ ID NO:40)

Figure 14A

15C1 Hu V<sub>H</sub> version 4-28
QVQLQESGPG LVKPSDTLSL TCAVSGYSI X$_1$ GGYSWHWIRQ PPGKGLEW X$_2$G
YIHYSGYTDF NPSLKTR X$_3$T X$_4$ SRDTSKNQFS LKLSSVTAVD TAVYYCARKD
PSDGFPYWGQ GTLVTVSS (SEQ ID NO:41)

CDR 1: GGYSWH (SEQ ID NO:23)
    CDR 2: YIHYSGYTDFNPSLKT (SEQ ID NO:24)
    CDR 3: KDPSDGFPY (SEQ ID NO:25)

Where X$_1$ is Thr or Ser
Where X$_2$ is Ile or Met
Where X$_3$ is Val or Ile
Where X$_4$ is Met or Ile

15C1 Hu V<sub>H</sub> version 3-66
EVQLVESGGG LVQPGGSLRL SCAX$_1$SGYSIT GGYSWHWVRQ APGKGLEWX$_2$S
YIHYSGYTDF NPSLKTRFTI SRDNSKNTX$_3$Y LQMNSLRAED TAVYYCARKD
PSDGFPYWGQ GTLVTVSS (SEQ ID NO:42)

CDR 1: GGYSWH (SEQ ID NO:23)
    CDR 2: YIHYSGYTDFNPSLKT (SEQ ID NO:24)
    CDR 3: KDPSDGFPY (SEQ ID NO:25)

Where X$_1$ is Ala or Val
Where X$_2$ is Val or Met
Where X$_3$ is Leu or Phe

Figure 14B

15C1 Hu VL version L6
EIVLTQSPAT LSLSPGERAT LSCRASQSIS DHLHWYQQKP GQAPRLLIX$_1$Y
ASHAISGIPA RFSGSGSGTD FTLTISSLEP EDFAVYYCQN GHSFPLTFGG
GTKVEIK (SEQ ID NO:43)

CDR1: RASQSISDHLH (SEQ ID NO:28)
    CDR2: YASHAIS (SEQ ID NO:29)
    CDR3: QNGHSFPLT (SEQ ID NO:30)

Where X$_1$ is Lys or Tyr

15C1 Hu VL version A26
EIVLTQSPDF QSVTPKEKVT ITCRASQSIS DHLHWYQQKP DQSPKLLIKY
ASHAISGVPS RFSGSGSGTD FTLTINSLEA EDAATYYCQN GHSFPLTFGG
GTKVEIK (SEQ ID NO:44)

CDR1: RASQSISDHLH (SEQ ID NO:28)
    CDR2: YASHAIS (SEQ ID NO:29)
    CDR3: QNGHSFPLT (SEQ ID NO:30)

Figure 15

18H10 Hu VH version 1-69
QVQLVQSGAE VKKPGSSVKV SCKASGFNIK DSYIHWVRQA PGQGLEWX$_1$GW
TDPENVNSIY DPRFQGRVTI TADX$_2$STSTAY X$_3$ELSSLRSED TAVYYCARGY
NGVYYAMDYW GQGTTVTVSS (SEQ ID NO:45)

CDR1: DSYIH (SEQ ID NO:3)
    CDR2: WTDPENVNSIYDPRFQG (SEQ ID NO:4SEQ ID NO:4)
    CDR3: GYNGVYYAMDY (SEQ ID NO:5)

Where X$_1$ is Met or Ile
Where X$_2$ is Lys or Thr
Where X$_3$ is Met or Leu

18H10 Hu VL version L6
EIVLTQSPAT LSLSPGERAT LSCSASSSVI YMHWYQQKPG QAPRLLIYRT
YNLASGIPAR FSGSGSGTDX$_1$ TLTISSLEPE DFAVYYCHQW SSFPYTFGQG
TKVEIK (SEQ ID NO:46)

CDR1: SASSSVIYMH (SEQ ID NO:8)
    CDR2: RTYNLAS (SEQ ID NO:9)
    CDR3: HQWSSFPYT (SEQ ID NO:10)

Where X$_1$ is Phe or Tyr

Figure 16

7E3 Hu VH version 2-70
QVTLRESGPA LVKPTQTLTL TCTFSGFSLX$_1$ TYNIGVGWIR QPPGKALEWL
AHIWWNDNIY YNTVLKSRLT X$_2$SKDTSKNQV VLTMTNMDPV DTATYYCX$_3$RM
AEGRYDAMDY WGQGTLVTVS S (SEQ ID NO:47)

CDR1: TYNIGVG (SEQ ID NO:33)
    CDR2: HIWWNDNIYYNTVLKS (SEQ ID NO:34)
    CDR3: MAEGRYDAMDY (SEQ ID NO:35)

Where X$_1$ is Ser or Thr
Where X$_2$ is Ile or Phe
Where X$_3$ is Ile or Ala

7E3 Hu VH version 3-66
EVQLVESGGG LVQPGGSLRL SCAX$_1$SGFSLT TYNIGVGWVR QAPGKGLEWX$_2$
SHIWWNDNIY YNTVLKSRLT X$_3$SX$_4$DNSKNTX$_5$ YLQMNSLRAE DTAVYYCX$_6$RM
AEGRYDAMDY WGQGTLVTVS S (SEQ ID NO:48)

CDR1: TYNIGVG (SEQ ID NO:33)
    CDR2: HIWWNDNIYYNTVLKS (SEQ ID NO:34)
    CDR3: MAEGRYDAMDY (SEQ ID NO:35)

Where X$_1$ is Phe or Ala
Where X$_2$ is Val or Leu
Where X$_3$ is Ile or Phe
Where X$_4$ is Lys or Arg
Where X$_5$ is Leu or Val
Where X$_6$ is Ile or Ala

7E3 Hu VL version L19
DIQMTQSPSS VSASVGDRVT ITCRASQDIT NYLNWYQQKP GKAPKLLIYY
TSKLHSGVPS RFSGSGSGTD X$_1$TLTISSLQP EDFATYX$_2$CQQ GNTFPWTFGG
GTKVEIK (SEQ ID NO:49)

CDR1: RASQDITNYLN (SEQ ID NO:38)
    CDR2: YTSKLHS (SEQ ID NO:39)
    CDR3: QQGNTFPWT (SEQ ID NO:40)

Where X$_1$ is Phe or Tyr
Where X$_2$ is Tyr or Phe

Figure 17

```
5'  CCC CCC CTC GAG CTT CAG CAG TCA GGA CCT GGC CTG GTG AAA CCT TCT CAG TCT CTG TCC CTC ACC TGC ACT GTC
    pro pro leu glu leu gln gln ser gly pro gly leu val lys pro ser gln ser leu ser leu thr cys thr val
                 4                Fr.1

ACT GGC TAC ATA ACC AGT GAT GCC TGG TCT CCC GCC AAC TGG ATC CGG CAG TTT CCA GGA AAC AGA CTG GAG TGG
    thr gly tyr ile thr ser asp ala trp ser pro ala asn trp ile arg gln phe pro gly asn arg leu glu trp
                 31       CDR                         35B       Fr.2

ATG GGG TAC AGC TAC AGT GGT AGC ACT AGT TAC AAC CCA TCT CTC AAA TCT CGA ATC TCT ATC
    met gly tyr ser tyr ser gly ser thr ser tyr asn pro ser leu lys ser arg ile ser ile
        50              CDR2                                                Fr.3

ACT CGA GAC ACA TCC AAG AAC CAG TTG AAT TCG GTG ACT GAG GAC ACA GCC ACA TAT TAC
    thr arg asp thr ser lys asn gln leu asn ser val thr glu asp thr ala thr tyr tyr TGT GTA AGA GGG CTC CGG TTT GCT TAC TGG GGA CAA GGG ACT CTG GTC ACT GTC TCT GCA
    cys val arg gly leu arg phe ala tyr trp gly gln gly thr leu val thr val ser ala
                95      CDR3                    102    Fr.4                 113  CH-1

CCC CCC TCT GTC TAT CCA CTG GCC CCT GGA TCT GCT GCC CAA ACA ACT GCC ATG GTG ACC CTG GGA TGC CTG GTC
    pro pro ser val tyr pro leu ala pro gly ser ala ala gln thr thr ala met val thr leu gly cys leu val AAG GCT TAT TTC CCT GAG CCA GTG ACA GTG ACC TGG AAC TCT GGA TCC CTG TCC AGC GGT GTG CAC ACC TTC CCA
    lys ala tyr phe pro glu pro val thr val thr trp asn ser gly ser leu ser ser gly val his thr phe pro GCT GTC CTG CAG TCT GAC CTC TAC ACT CTG AGC AGC TCA GTG ACT GTC CCC TCC AGC ACC TGG CCC AGC GAG ACC
    ala val leu gln ser asp leu tyr thr leu ser ser ser val thr val pro ser ser thr trp pro ser glu thr GTC ACC TGC AAC GTT GCC CAC CCG GCC AGC AGC ACC AAG GTG GAC AAG AAA ATT 3'       SEQ ID NO:50
    val thr cys asn val ala his pro ala ser ser thr lys val asp lys lys ile          SEQ ID NO:51
                                                                  223
```

Figure 18

```
5'
    5                                                    FR.1
ATG ACA CAG TCT CCA GCT TCT TTG GCT GTG TCT CTA GGG CAG AGG GCC CCA TAT CCT
met thr gln ser pro ala ser leu ala val ser leu gly gln arg ala pro tyr pro
                                                                24    CDR1
TGC AGA GCC AGT GAA
cys arg ala ser glu AGT GTT GAT AGT TAT GTC AAT AGT TTT CTC CAC TGG TAC CAG CAG AAA CCA GGA CAG
ser val asp ser tyr val asn ser phe leu his trp tyr gln gln lys pro gly gln
                                       34
CCA CCC AAA CTC
pro pro lys leu 50 CDR2                             56                   Fr.3
CTC ATC TAT CGT GCA TCC AAC CTA CAA TCT GGG ATC CCT GCC AGG TTC AGT GGC AGT
leu ile tyr arg ala ser asn leu gln ser gly ile pro ala arg phe ser gly ser
GGG TCT AGG ACA GAC
gly ser arg thr asp TTC ACC CTC ACC ATT AAT CCT GTG GAG GCT GAT GAT GTT GCA ACC TAT TAC TGT CAG
phe thr leu thr ile asn pro val glu ala asp asp val ala thr tyr tyr cys gln
                                                                     89   CDR3
CAA AGT AAT GAG GAT
gln ser asn glu asp Fr.4                              107 CH-1
CCG ACG TTC GGA GGG GGG ACC AAG CTG GAA ATA AAA CGG GCT GAT GCT GCA CCC CTT
pro thr phe gly gly gly thr lys leu glu ile lys arg ala asp ala ala pro leu
GTA TCC ATC TTC CCC
val ser ile phe pro CCA TCC AGT GAG CAG TTA ACA TCT GGA GGT GCC TCA GTT GTG TGC TTC TTG AAC AAC
pro ser ser glu gln leu thr ser gly gly ala ser val val cys phe leu asn asn
TTC TAC CCC AAA GAC ATC
phe tyr pro lys asp ile AAT GTC AAG TGG AAG ATT GAT GGC AGT GAA CGA CAA CGA CAA GGC GTC CTG AAC AGT TGG ACT GAT CAG GAC AGC AAA
asn val lys trp lys ile asp gly ser glu arg gln arg gln gly val leu asn ser trp thr asp gln asp ser lys GAC AGC ACC TAC AGC ATG AGC AGC ACC CTC ACG TTG ACC GAG GAG TAT GAA CGA CAT AAC AGC TAT ACC TGT
asp ser thr tyr ser met ser ser thr leu thr leu thr glu glu tyr glu arg his asn ser tyr thr cys 214
GAG GCC ACT CAC AAG ACA TCA ACT CCC ATT GTC AAG AGC TTC AAC AGG AAT GAG TGT 3'      SEQ ID NO:52
glu ala thr his lys thr ser thr pro ile val lys ser phe asn arg asn glu cys         SEQ ID NO:53
```

Figure 19

```
          10         20         30         40         50
   ATGTCCTCTC CACAGTCCCT GAAGACACTG ATTCTAACCA TGGGATGGAG        SEQ ID NO:54
   TACAGGAGAG GTGTCAGGGA CTTCTGTGAC TAAGATTGGT ACCCTACCTC        SEQ ID NO:55
   MetSerSer ProGlnSerLeu LysThrLeu IleLeuThr MetGlyTrpSer>      SEQ ID NO:56

60         70         80         90        100
   CTGGATCTTT CTCTTCCTCC TGTCAGGAAC TGCAGGTGTC CACTCCCAGG
   GACCTAGAAA GAGAAGGAGG ACAGTCCTTG ACGTCCACAG GTGAGGGTCC

TrpIlePhe LeuPheLeu LeuSerGlyThr AlaGlyVal HisSerGln>

110        120        130        140        150
   TTCAGCTGCA GCAGTCTGGA CCTGAGCTGG TGAACCCTGG GGCGTCAGTG
   AAGTCGACGT CGTCAGACCT GGACTCGACC ACTTGGGACC CCGCAGTCAC
   ValGlnLeuGln GlnSerGly ProGluLeu ValAsnProGly AlaSerVal>

160        170        180        190        200
   AAGTTGTCCT GCAAGGCTTC TGGCTTCACC TTCACAACCT ACGGTATAAA
   TTCAACAGGA CGTTCCGAAG ACCGAAGTGG AAGTGTTGGA TGCCATATTT
   LysLeuSer CysLysAlaSer GlyPheThr PheThrThr TyrGlyIleAsn>

210        220        230        240        250
   CTGGGTGAAG CAGGGGCCTG GACAGGGACT TGAGTGGATT GGATGGATTT
   GACCCACTTC GTCCCCGGAC CTGTCCCTGA ACTCACCTAA CCTACCTAAA
    TrpValLys GlnGlyPro GlyGlnGlyLeu GluTrpIle GlyTrpIle>

260        270        280        290        300
   ATCCTAGAGA TGGTAGTACT AACTTCAATG AGAATTTCAA GGACAAGGCC
   TAGGATCTCT ACCATCATGA TTGAAGTTAC TCTTAAAGTT CCTGTTCCGG
   TyrProArgAsp GlySerThr AsnPheAsn GluAsnPheLys AspLysAla>

310        320        330        340        350
   GCATTGACTG TAGACACATC CTCCAGCACA GCGTACATGG AACTCCACAG
   CGTAACTGAC ATCTGTGTAG GAGGTCGTGT CGCATGTACC TTGAGGTGTC
   AlaLeuThr ValAspThrSer SerSerThr AlaTyrMet GluLeuHisSer>

360        370        380        390        400
   CCTGACATCT GAAGACTCTG CGGTCTATTT CTGTGCAAGA CTGACTGGTG
   GGACTGTAGA CTTCTGAGAC GCCAGATAAA GACACGTTCT GACTGACCAC
    LeuThrSer GluAspSer AlaValTyrPhe CysAlaArg LeuThrGly>

410        420        430        440        450
   GGACATTCCT TGACTATTGG GGCCAGGGCA CCACTCTCAC AGTCTCCTCA
   CCTGTAAGGA ACTGATAACC CCGGTCCCGT GGTGAGAGTG TCAGAGGAGT
   GlyThrPheLeu AspTyrTrp GlyGlnGly ThrThrLeuThr ValSerSer>

460        470        480        490        500
   GCCAAAACGA CACCCCCATC TGTCTATCCA CTGGCCCCTG GATCTGCTGC
   CGGTTTTGCT GTGGGGGTAG ACAGATAGGT GACCGGGGAC CTAGACGACG
   AlaLysThr ThrProProSer ValTyrPro LeuAlaPro GlySerAlaAla>

```
           10          20          30          40          50
    ATGGAGTCAG  ACACACTCCT  GCTATGGGTG  CTGCTGCTCT  GGGTTCCAGG
    TACCTCAGTC  TGTGTGAGGA  CGATACCCAC  GACGACGAGA  CCCAAGGTCC
    MetGluSer   AspThrLeuLeu  LeuTrpVal  LeuLeuLeu   TrpValProGly>

60          70          80          90         100
    CTCCACTGGT  GACATTGTGC  TCACCCAATC  TCCAGCTTCT  TTGGCTGTGT
    GAGGTGACCA  CTGTAACACG  AGTGGGTTAG  AGGTCGAAGA  AACCGACACA
     SerThrGly  AspIleVal   LeuThrGlnSer  ProAlaSer  LeuAlaVal>

110         120         130         140         150
    CTCTAGGGCA  GAGAGCCACC  ATCTCCTGCA  GAGCCAGTGA  AAGTGTTGAA
    GAGATCCCGT  CTCTCGGTGG  TAGAGGACGT  CTCGGTCACT  TTCACAACTT
    SerLeuGlyGln  ArgAlaThr  IleSerCys   ArgAlaSerGlu  SerValGlu>

160         170         180         190         200
    TATTATGGCA  CAAGTTTAAT  GCAGTGGTAC  CAACAGAAAC  CAGGACAGCC
    ATAATACCGT  GTTCAAATTA  CGTCACCATG  GTTGTCTTTG  GTCCTGTCGG
    TyrTyrGly   ThrSerLeuMet  GlnTrpTyr  GlnGlnLys   ProGlyGlnPro>

210         220         230         240         250
    ACCCAAACTC  CTCATCTTTG  GTGCATCCAA  CGTAGAATCT  GGGGTCCCTG
    TGGGTTTGAG  GAGTAGAAAC  CACGTAGGTT  GCATCTTAGA  CCCCAGGGAC
     ProLysLeu  LeuIlePhe   GlyAlaSerAsn  ValGluSer  GlyValPro>

260         270         280         290         300
    TCAGGTTCAG  TGGCAGTGGG  TCTGGGACAG  ACTTCAGCCT  CAACATCCAT
    AGTCCAAGTC  ACCGTCACCC  AGACCCTGTC  TGAAGTCGGA  GTTGTAGGTA
    ValArgPheSer  GlySerGly  SerGlyThr   AspPheSerLeu  AsnIleHis>

310         320         330         340         350
    CCTGTGGAGG  AGGATGATAT  TGTAATGTAT  TTCTGTCAGC  AAAGTAGGAA
    GGACACCTCC  TCCTACTATA  ACATTACATA  AAGACAGTCG  TTTCATCCTT
    ProValGlu   GluAspAspIle  ValMetTyr  PheCysGln   GlnSerArgLys>

360         370         380         390         400
    ACTTCCGTGG  ACGTTCGGTG  GAGGCACCAA  GCTGGAAATC  AAACGGGCTG
    TGAAGGCACC  TGCAAGCCAC  CTCCGTGGTT  CGACCTTTAG  TTTGCCCGAC
    LeuProTrp   ThrPheGly   GlyGlyThrLys  LeuGluIle  LysArgAla>

410         420         430         440
    ATGCTGCACC  AACTGTATCC  ATCTTCCCAC  CATCCAGTGA  GCA       SEQ ID NO:57
    TACGACGTGG  TTGACATAGG  TAGAAGGGTG  GTAGGTCACT  CGT       SEQ ID NO:58
    AspAlaAlaPro  ThrValSer  IlePhePro   ProSerSerGlu  Xxx>    SEQ ID NO:59
```

Figure 21

```
  1  MLPFLFFSTL FSSIFTEAQK QYWVCNSSDA SISYTYCDKM QYPISINVNP CIELKGSKGL
 61  LHIFYIPRRD LKQLYFNLYI TVNTMNLPKR KEVICRGSDD DYSFCRALKG ETVNTTISFS
121  FKGIKFSKGK YKCVVEAISG SPEEMLFCLE FVILHQPNSN (SEQ ID NO:60)
```

Figure 22

```
  1  mmsasrlagt lipamaflsc vrpeswepcv evvpnityqc melnfykipd nlpfstknld
 61  lsfnplrhlg sysffsfpel qvldlsrcei qtiedgayqs lshlstlilt gnpiqslalg
121  afsglsslqk lvavetnlas lenfpighlk tlkelnvahn liqsfklpey fsnltnlehl
181  dlssnkiqsi yctdlrvlhq mpllnlsldl slnpmnfiqp gafkeirlhk ltlrnnfdsl
241  nvmktciqgl aglevhrlvl gefrnegnle kfdksalegl cnltieefrl ayldyylddi
301  idlfncltnv ssfslvsvti ervkdfsynf gwqhlelvnc kfgqfptlkl kslkrltfts
361  nkggnafsev dlpslefldl srnglsfkgc csqsdfgtts lkyldlsfng vitmssnflg
421  leqlehldfq hsnlkqmsef svflslrnli yldishthtr vafngifngl sslevlkmag
481  nsfqenflpd iftelrnltf ldlsqcqleq lsptafnsls slqvlnmshn nffsldtfpy
541  kclnslqvld yslnhimtsk kqelqhfpss laflnltqnd factcehqsf lqwikdqrql
601  lvevermeca tpsdkqgmpv lslnitcqmn ktiigvsvls vlvvsvvavl vykfyfhlml
661  lagcikygrg eniydafviy ssqdedwvrn elvknleegv ppfqlclhyr dfipgvaiaa
721  niihegfhks rkvivvvsqh fiqsrwcife yeiaqtwqfl ssragiifiv lqkvektllr
781  qqvelyrlls rntyleweds vlgrhifwrr lrkalldgks wnpegtvgtg cnwqeatsi
     (SEQ ID NO:61)
```

COMBINING THERAPIES TARGETING MULTIPLE TOLL-LIKE RECEPTORS

RELATED APPLICATIONS

This application claims priority under 35 U.S.C. §119(e) to U.S. Provisional Application No. 60/635,421, filed Dec. 10, 2004, which is hereby incorporated by reference in its entirety.

FIELD OF THE INVENTION

This invention relates generally to compositions that contain multiple antibodies, e.g., multiple neutralizing antibodies, that immunospecifically bind to one or more toll-like receptors, e.g., two or more toll-like receptors, and methods of using these compositions in the treatment of inflammatory disorders.

BACKGROUND

Toll receptors, which were first discovered in *Drosophila*, are type I transmembrane protein having leucine-rich repeats (LRRs) in the extracellular portion of the protein, and one or two cysteine-rich domains. The mammalian homologs of the *Drosophila* Toll receptors are known as "Toll-like receptors" (TLRs). TLRs have been have been shown to play a role in innate immunity by recognizing microbial particles and activating immune cells against the source of these microbial particles.

Currently, ten types of Toll-like receptors have been identified, TLRs 1-10. These TLRs are characterized by the homology of their intracellular domains to that of the IL-1 receptor, and by the presence of extracellular leucine-rich repeats.

TLRs are activated by different types of microbial particles known as pathogen-associated molecular patterns (PAMPs). For example, TLR4 is primarily activated by lipopolysaccharide (LPS), while TLR2 is activated by lipoteichoic acid (LTA), lipoarabinomannan (LAM), lipoprotein (BLP), and peptideglycans (PGN). It is therefore possible that any given microbe can stimulate several different TLRs in parallel at any given time during an infection.

In addition, certain TLRs have been shown to require the presence of accessory proteins in order to function. For example, TLR4 forms a complex with myeloid differentiation protein-2 (MD-2) on the cell surface. The MD-2 protein has been found to interact directly with TLR4, and MD-2 has the ability to enable post-translational modifications of TLR4, as well as facilitate its transport to the cell surface. CD14 is another protein that has been linked to TLR4 function, and in addition, CD14 has also been implicated in TLR2 recognition of microbes.

SUMMARY OF THE INVENTION

The invention provides compositions that contain a combination of antibodies, e.g., multiple neutralizing monoclonal antibodies (MAbs), or one or more multivalent antibodies that immunospecifically bind to one or more toll-like receptors, e.g., two or more toll-like receptors. The invention also provides methods of using these combinations of antibodies in the treatment of inflammatory disorders. The inflammatory disorder is, for example, sepsis, acute inflammation and chronic inflammation. For example, the chronic inflammation is associated with an autoimmune disease or inflammatory disorder such as inflammatory bowel disorder, osteoarthritis, rheumatoid arthritis, multiple sclerosis, atherosclerosis, asthma or COPD (Chronic Obstructive Pulmonary Disease).

The invention also relates to the identification of the relative contribution of TLR4, TLR2 and CD14 in the recognition of and immune response to the gram-negative bacterium *Escherichia coli* in human whole blood using neutralizing monoclonal antibodies to each receptor component. Furthermore, the invention relates to methods of detecting the effect of combination MAb treatment in inhibiting immune response.

The invention provides compositions that contain multiple antibodies or compositions that contain one or more multivalent antibodies. The combination of antibodies includes two or more antibodies, wherein the antibodies immunospecifically bind to two or more targets such as, for example, toll-like receptor 4 (TLR4), toll-like receptor 2 (TLR2), toll-like receptor 1 (TLR1), toll-like receptor 5 (TLR5), toll-like receptor 6 (TLR6), MD-2 and CD14. For example, the combination contains at least two antibodies, an antibody that immunospecifically binds TLR4 and an antibody that immunospecifically binds TLR2. For example, the combination contains at least three antibodies, an antibody that immunospecifically binds TLR4, an antibody that immunospecifically binds TLR2 and an antibody that immunospecifically binds MD-2. The combination contains at least three antibodies, for example, an antibody that immunospecifically binds TLR4, an antibody that immunospecifically binds TLR2 and an antibody that immunospecifically binds CD14. The combination contains at least four antibodies, an antibody that immunospecifically binds TLR4, an antibody that immunospecifically binds TLR2, an antibody that immunospecifically binds MD-2, and an antibody that immunospecifically binds CD14.

The antibodies are, for example, monoclonal antibodies, and more specifically, neutralizing monoclonal antibodies that are capable of blocking, i.e., neutralizing the biological activity or function of the target. As used herein, the terms "antibody" and "antibodies" refer to monovalent (i.e., monospecific) antibodies and multivalent (e.g., bispecific, trispecific) antibodies. Suitable antibodies include, e.g., humanized antibodies, fully human antibodies and fragments thereof. For example, the antibodies are capable of blocking LPS-induced pro-inflammatory cytokine production. As used herein, the term "pro-inflammatory cytokine" refers to those immunoregulatory cytokines that promote inflammation and/or are associated with inflammation. Pro-inflammatory cytokines, include, for example, IL-6, IL-8, TNF-alpha, IL1-alpha, IL1-beta, IFN-alpha, IFN-beta, IFN-gamma, IL-10, IL12, IL-23, IL17, and IL18.

The antibodies recognize, for example, the TLR4/MD-2 receptor complex expressed on the cell surface. Antibodies used in the compositions and methods of the invention include antibodies that bind the human TLR4/MD-2 receptor complex and also bind TLR4 independently of the presence of MD-2. Antibodies of the invention also include antibodies that bind the TLR4 portion of the human TLR4/MD-2 receptor complex, but binding is entirely dependent on the presence of MD-2. In addition, antibodies of the invention include antibodies that bind the human TLR4/MD-2 receptor complex and also bind MD-2 but only in the presence of TLR4. Other suitable antibodies include antibodies that bind MD-2 when not complexed to TLR4, antibodies that bind TLR2, antibodies that bind TLR1, antibodies that bind TLR5, antibodies that bind TLR6 and antibodies that bind CD14.

Exemplary antibodies of the invention include, for example, the murine 18H10 antibody, the murine 16G7 antibody, the murine 15C1 antibody, the murine 7E3 antibody, the humanized 18H10 antibody, the humanized 16G7 antibody, the humanized 15C1 antibody, the humanized 7E3. These antibodies show specificity for the human TLR4/MD-2 receptor complex, and they have been shown to inhibit receptor activation and subsequent intracellular signaling via LPS. These antibodies have distinct specificities. For example, 15C1 binds TLR4 independently of the presence of MD-2, 7E3 binds to TLR4, but binding is dependent on the presence of MD-2, and 18H10 binds to MD-2, but requires the presence of TLR4, as the MAb does not bind soluble forms of MD-2.

Other exemplary antibodies include antibodies that recognize CD14, such as the anti-CD14 monoclonal antibody known as 28C5 (see e.g., U.S. Pat. No. 6,444,206, hereby incorporated by reference in its entirety), and antibodies that recognize TLR4, including, e.g., the anti-TLR2 monoclonal antibody known as T2.5 (see e.g., WO 2005/028509, hereby incorporated by reference in its entirety).

Suitable antibodies used in the combinations and compositions of the invention contain a heavy chain variable region having the amino acid sequence of SEQ ID NOS: 2, 12, 22, 32, 41, 42, 45, 47, 48, 51 and 56. Suitable antibodies contain a light chain variable region having the amino acid sequence of SEQ ID NOS: 7, 17, 27, 37, 43, 44, 46, 49, 53 and 59. The three heavy chain CDRs include an amino acid sequence at least 90%, 92%, 95%, 97% 98%, 99% or more identical a sequence selected from the group consisting of GGYSWH (SEQ ID NO:23); YIHYSGYTDFNPSLKT (SEQ ID NO:24); KDPSDGFPY (SEQ ID NO:25); DSYIH (SEQ ID NO:3); WTDPENVNSIYDPRFQG (SEQ ID NO:4), GYNGVYYAMDY (SEQ ID NO:5); TYNIGVG (SEQ ID NO:33); HIWWNDNIYYNTVLKS (SEQ ID NO:34); MAEGRYDAMDY (SEQ ID NO:35), TYGIN (SEQ ID NO:62); GFTFTTYG (SEQ ID NO:63); WIYPRDGSTNFNENFKD (SEQ ID NO: 64); IYPRDGST (SEQ ID NO: 65); ARLTGGTFLDY (SEQ ID NO: 66); SDSAWN (SEQ ID NO: 72), YISYSGSTSYNPSLKS (SEQ ID NO: 73) and GLRFAY (SEQ ID NO: 74). The three light chain CDRs include an amino acid sequence at least 90%, 92%, 95%, 97% 98%, 99% or more identical to a sequence selected from the group consisting of the amino acid sequence of RASQSISDHLH (SEQ ID NO:28); YASHAIS (SEQ ID NO:29); QNGHSFPLT (SEQ ID NO:30); SASSSVIYMH (SEQ ID NO:8); RTYNLAS (SEQ ID NO:9); HQWSSFPYT (SEQ ID NO:10); RASQDITNYLN (SEQ ID NO:38); YTSKLHS (SEQ ID NO:39); QQGNTFPWT (SEQ ID NO:40); RASESVEYYGTSLMQ (SEQ ID NO: 67); ESVEYYGTSL (SEQ ID NO: 68); GASNVES (SEQ ID NO:69); GAS (SEQ ID NO:70); QQSRKLPWT (SEQ ID NO:71), RASESVDSYVNSFLH (SEQ ID NO: 75); RASNLQS (SEQ ID NO: 76) and QQSNEDPYT (SEQ ID NO:77).

For the antibodies that immunospecifically bind a TLR4/MD-2 complex, the antibody or a portion of a multivalent antibody binds to an epitope that includes one or more amino acid residues on human TLR4 between residues 289 and 375 of SEQ ID NO:61. For example, the antibody or a portion of a multivalent antibody specifically binds to an epitope that includes residues selected from the group consisting of at least residues 293 through 295 of SEQ ID NO:61; at least residues 296 and 297 of SEQ ID NO:61; at least residues 319 through 321 of SEQ ID NO:61; at least residues 328 and 329 of SEQ ID NO:61; at least residues 349 through 351 of SEQ ID NO:61; and at least residues 369 through 371 of SEQ ID NO:61. For example, the antibody or a portion of a multivalent antibody specifically binds to an epitope that contains at least residues 328, 329, 349 through 351 and 369 through 371 of SEQ ID NO:61. In another example, the antibody or a portion of a multivalent antibody specifically binds to an epitope that includes at least residues 293 through 295, 296, 297 and 319 through 321 of SEQ ID NO:61.

For antibodies that bind the TLR4/MD2 complex, the antibody or a portion of a multivalent antibody binds to an epitope on human MD-2 between residues 19 and 57 of SEQ ID NO:60. For example, the antibody specifically binds to an epitope that contains at least residues 53 of SEQ ID NO:60.

For antibodies that bind TLR2, the antibody or a portion of a multivalent antibody binds to an epitope in the C-terminal portion of the extracellular domain of TLR2 (i.e., TLR2ECD).

The invention also provides a method of alleviating a symptom of a pathology associated with an inflammatory disorder by administering a combination of antibodies to a subject in which such alleviation is desired in an amount sufficient to alleviate the symptom of the pathology in the subject. The subject is, for example, a human.

The combination of antibodies used in the methods of the invention includes two or more antibodies, wherein the antibodies immunospecifically bind to two or more targets such as, for example, toll-like receptor 4 (TLR4), toll-like receptor 2 (TLR2), MD-2 and CD14. For example, the combination contains at least two antibodies, an antibody that immunospecifically binds TLR4 and an antibody that immunospecifically binds TLR2. For example, the combination contains at least three antibodies, an antibody that immunospecifically binds TLR4, an antibody that immunospecifically binds TLR2 and an antibody that immunospecifically binds MD-2. The combination contains at least three antibodies, an antibody that immunospecifically binds TLR4, an antibody that immunospecifically binds TLR2 and an antibody that immunospecifically binds CD14. The combination contains at least four antibodies, an antibody that immunospecifically binds TLR4, an antibody that immunospecifically binds TLR2, an antibody that immunospecifically binds MD-2, and an antibody that immunospecifically binds CD14. The antibodies used in the methods of the invention also include multivalent antibodies that immunospecifically bind to at least two targets selected from TLR4, MD-2, TLR2 and CD14.

The combination of antibodies is present in amount that is sufficient to prevent or reduce initiation of an immune response in the subject to be treated.

BRIEF DESCRIPTION OF THE DRAWINGS

FIGS. 10A-10F are a series of illustrations depicting the VH nucleotide sequence (SEQ ID NO:1) (FIG. 10A), the VH amino acid sequence (SEQ ID NO:2) (FIG. 10B), the VL nucleotide sequence (SEQ ID NO:6) (FIG. 10D), and the VL amino acid sequence (SEQ ID NO:7) for mu18H10 (FIG. 10E). The VH complementarity determining regions (CDRs) (SEQ ID NOs:3, 4 and 5) (FIG. 10C) and the VL CDRs (SEQ ID NOs: 8, 9 and 10) (FIG. 10F) are highlighted in the underlined, italic text in FIGS. 10B and 10E.

FIGS. 11A-11F are a series of illustrations depicting the VH nucleotide sequence (SEQ ID NO:11) (FIG. 11A), the VH amino acid sequence (SEQ ID NO:12) (FIG. 11B), the VL nucleotide sequence (SEQ ID NO:16) (FIG. 11D), and the VL amino acid sequence (SEQ ID NO:17) (FIG. 11E) for mu16G7. The VH complementarity determining regions (CDRs) (SEQ ID NOs: 13, 14 and 15) (FIG. 11C) and the VL CDRs (SEQ ID NOs: 18, 19 and 20) (FIG. 11F) are highlighted in the underlined, italic text in FIGS. 11B and 11E.

FIGS. 12A-12F are a series of illustrations depicting the VH nucleotide sequence (SEQ ID NO:21) (FIG. 12A), the VH amino acid sequence (SEQ ID NO:22) (FIG. 12B), the VL nucleotide sequence (SEQ ID NO:26) (FIG. 12D), and the VL amino acid sequence (SEQ ID NO:27) (FIG. 12E) for mu15C1. The VH complementarity determining regions (CDRs) (SEQ ID NOs: 23, 24 and 25) (FIG. 12C) and the VL CDRs (SEQ ID NOs: 28, 29 and 30) (FIG. 12F) are highlighted in the underlined, italic text in FIGS. 12B and 12E.

FIGS. 13A-13F are a series of illustrations depicting the VH nucleotide sequence (SEQ ID NO:31) (FIG. 13A), the VH amino acid sequence (SEQ ID NO:32) (FIG. 13B), the VL nucleotide sequence (SEQ ID NO:36) (FIG. 13D), and the VL amino acid sequence (SEQ ID NO:37) (FIG. 13E) for mu7E3. The VH complementarity determining regions (CDRs) (SEQ ID NOs: 33, 34 and 35) (FIG. 13C) and the VL CDRs (SEQ ID NOs: 38, 39 and 40) (FIG. 13F) are highlighted in the underlined italic text in FIGS. 13B and 13E.

FIGS. 14A and 14B are a series of illustrations depicting two versions of the humanized VH amino acid sequence (SEQ ID NO:41), (SEQ ID NO:42) (FIG. 14A) and two versions of the humanized VL amino acid sequence (SEQ ID NO:43), (SEQ ID NO:44) (FIG. 14B) for hu15C1. The VH and VL CDRs are also shown.

FIG. 15 is an illustration depicting the VH amino acid sequence (SEQ ID NO:45) and the VL amino acid sequence (SEQ ID NO:46) for hu18H10. The VH and VL CDRs are also shown.

FIG. 16 is an illustration depicting two versions of the humanized VH amino acid sequence (SEQ ID NO:47), (SEQ ID NO:48) and the VL amino acid sequence (SEQ ID NO:49) for hu7E3. The VH and VL CDRs are also shown.

FIG. 17 is an illustration depicting the nucleic acid and amino acid sequences of the 28C5 heavy chain (SEQ ID NOS:50 and 51, respectively).

FIG. 18 is an illustration depicting the nucleic acid and amino acid sequences of the 28C5 light chain (SEQ ID NOS: 52 and 53, respectively).

FIG. 19 is an illustration depicting the nucleic acid and amino acid sequence of the T2.5 variable heavy chain (SEQ ID NOS:54-55 and 56, respectively).

FIG. 20 is an illustration depicting the nucleic acid and amino acid sequence of the T2.5 variable light chain (SEQ ID NOS:57-58 and 59, respectively).

FIG. 21 is an illustration depicting an amino acid sequence of a mature MD-2 accessory protein (SEQ ID NO:60).

FIG. 22 is an illustration depicting the amino acid sequence of human toll-like receptor 4 (TLR4) (SEQ ID NO:61).

DETAILED DESCRIPTION OF THE INVENTION

TLRs recognize microbial particles and activate immune cells against the source of these microbial particles. (See Takeda et al., Annu. Rev. Immunol., 21: 335-76 (2003), hereby incorporated by reference in its entirety). For example, TLR4 and MD-2 have been shown to form a complex on the cell surface, and the presence of MD-2 appears essential for the responsiveness of TLR4 to various ligands, including LPS. LPS is a gram-negative bacterial outer membrane glycolipid that is capable of strongly activating the innate immune system. LPS has been implicated as one of the major factors activating the immune system during the severe generalized inflammation resulting from gram-negative infection. (Lakhani et al., Curr. Opin. Pediatr. 15: 278-282 (2003), hereby incorporated by reference in its entirety).

Since the discovery of the mammalian TLRs in the latter part of the 1990s (Medzhitov et al, Nature 1997; Rock et al, PNAS 1998), a large number of activating ligands have been identified (reviewed in Akira, Nat Immun 2004). The majority of these ligands are purified or synthetic molecules known as PAMPs, derived from a variety of microorganisms. These ligands demonstrate a high level of specificity for individual TLRs and allow the host to detect the presence of invading pathogens within tissues. In general, these PAMPs are essential for the survival of the microorganism and therefore cannot be modified to avoid detection.

More recently, it has emerged that a second class of ligands derived from endogenous molecules is capable of initiating innate immunity by stimulating TLR signaling (reviewed in Johnson, Crit. Rev. Immunol 2003). These ligands are generally generated via the degradation of macromolecules arising as a result of inflammation, cellular rupture, activation of proteolytic cascades etc. and can be considered as initiating "danger signals" during times of tissue injury or stress. For example, endogenous ligands have been identified for TLR2, TLR4 and TLR9 (Johnson et al., Crit. Rev. Immunol., vol. 23(1-2) (2003)).

TLR signaling has been studied with highly purified TLR ligands. The examples provided herein demonstrate the elative TLR utilization of a whole microorganism during the initiation of the innate immune response. *E. coli* is composed of a number of PAMPs capable of stimulating TLR signaling. For example, the integral outer membrane component LPS is a very strong stimulator of TLR4. Gram-negative bacteria also possess lipoproteins, known to stimulate the immune system specifically via TLR2 (Akira and Takeda, Nat. Rev. Immunol., vol. 4(7):499-511 (2004)). Thus, an entire gram-negative bacterium may be capable of initiating an immune response via two TLRs in parallel.

Figure 2:
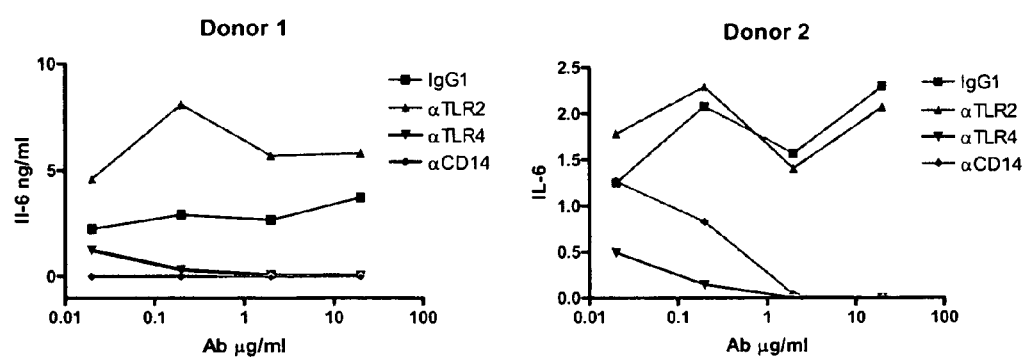
FIG. 2A is a series of graphs depicting the effect of the 15C1 anti-TLR4MAb, the T2.5 anti-TLR2MAb and the 28C5 anti-CD14 MAb on LPS-induced IL-6 production in whole blood.
FIG. 2B is a series of graphs depicting the effect of the 15C1 anti-TLR4MAb, the T2.5 anti-TLR2MAb and the 28C5 anti-CD14 MAb on $PAM_3CSK_4$-induced IL-6 production in whole blood.
Figure 2:
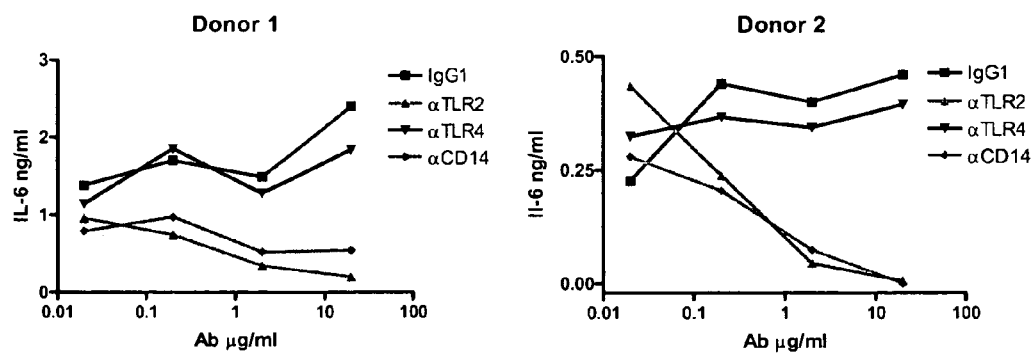
Figure 5:
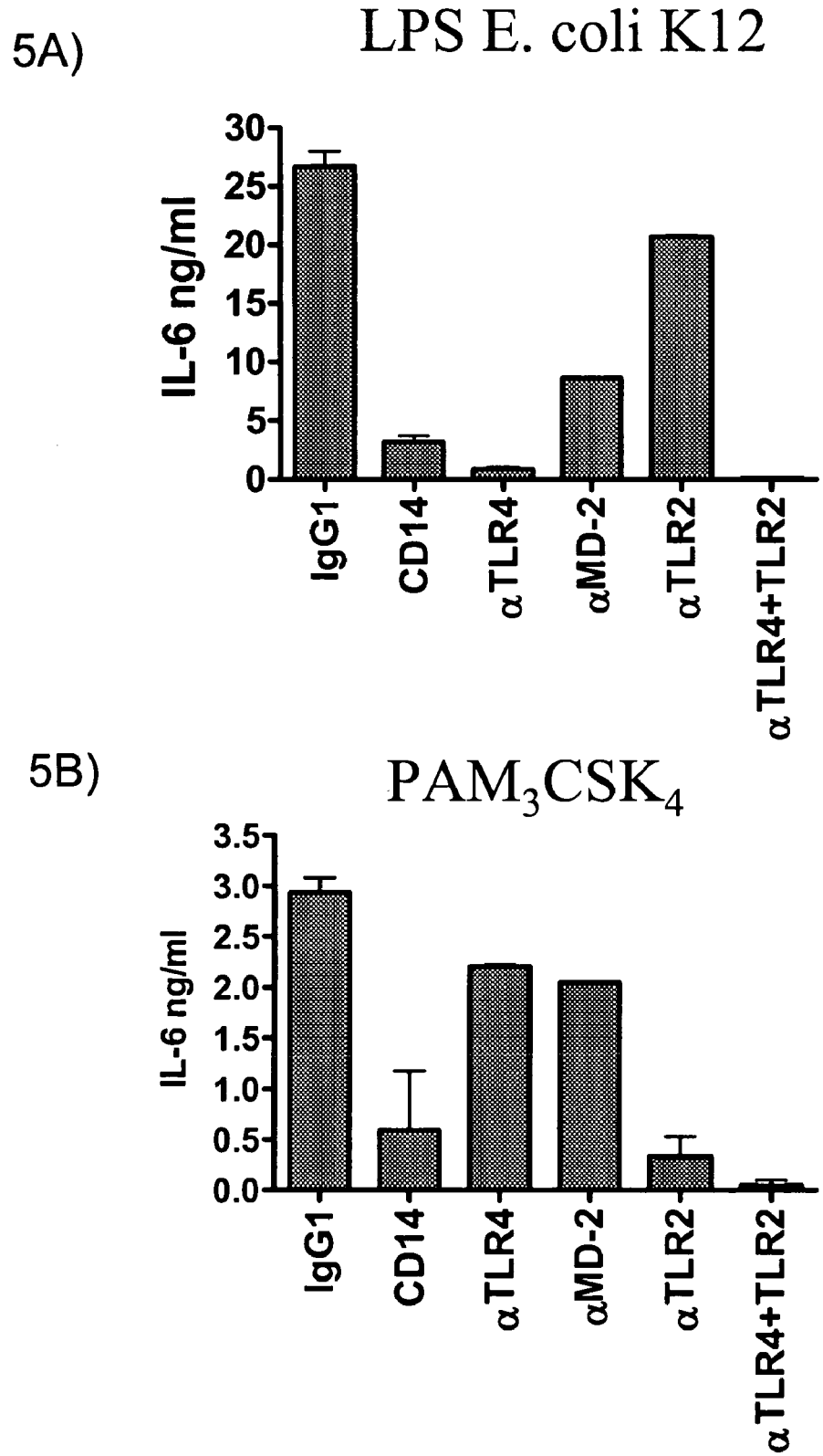
FIGS. 5A and 5B are a series of graphs depicting inhibition of bacterial PAMP-induced IL-6 production in human whole blood by specific anti-TLR MAbs.

The model used in the studies described in the Examples provided herein require the administration of heat inactivated E. coli gram-negative bacteria in human whole blood. IL-6 production was monitored as a readout for the immune response induced by heat inactivated E. coli. Blocking MAbs directed against TLR4, TLR2 and CD14 were used in an attempt to determine the contribution of each of these proteins in the resulting immune reaction. A partial inhibition of IL-6 with αTLR4 treatment was observed, whereas αTLR2 treatment did not affect cytokine levels. These results indicate that TLR4 ligands (e.g., LPS) are the major initiators of the immune response. However, a co-treatment of TLR4 and TLR2MAbs significantly reduced IL-6 levels in all donors (n=3) to a level well below the levels detected with the TLR4MAb alone. This data indicate that TLR2 ligands are playing a role in the initiation of the immune response, although these are not predominant. αCD14 MAbs had a greater neutralizing activity than the TLR4 and TLR2MAbs alone, due to the fact that CD14 is a co-receptor for both TLR4 and TLR2 ligands (FIG. 2, FIG. 5). An increased inhibition was observed when CD14 MAbs were co-administered with either TLR4 or TLR2 or both. This indicates that TLR2 and TLR4 ligands in E. coli can induce receptor signaling via a CD14-independent mechanism.

The methods described herein have many applications. For example, the methods described herein are used to target TLRs in the context of acute inflammatory diseases such as sepsis, and in chronic inflammatory diseases such as inflammatory bowel disorder (IBD), rheumatoid arthritis, multiple sclerosis and atherosclerosis (O'Neill, Curr. Op. Pharmacology, vol. 3:396-403 (2003)). The methods described herein target multiple TLRs or their accessory proteins in parallel, rather than as a mono-therapy. For example, systemic inflammation resulting from gram-negative bacterial infections has been implicated in the onset of sepsis and septic shock. A therapeutic approach aiming at reducing inflammation, using the methods described herein, targets more than one TLR or related protein. In addition, the methods described herein are used in IBD, where polymicrobial flora plays an important role in disease onset, to target more than one TLR or related protein, rather than one individual TLR or related protein. The methods described herein can also be used in to target TLR2 and TLR4 simultaneously in diseases where macromolecular degradation products or endogenous ligands are potentially exacerbating inflammation (osteoarthritis and rheumatoid arthritis are hypothetical indications for this), provide an advantage over targeting either TLR alone.

Accordingly, targeting more than one TLR or related protein is a potential therapeutic strategy in the treatment of disorders such as, for example, acute systemic inflammation and sepsis induced by gram-negative bacterial infection.

DEFINITIONS

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)). The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

As used herein, the term "antibody" refers to immunoglobulin molecules and immunologically active portions of immunoglobulin (Ig) molecules, i.e., molecules that contain an antigen binding site that specifically binds (immunoreacts with) an antigen. By "specifically bind" or "immunoreacts with" or "immunospecifically bind" is meant that the antibody reacts with one or more antigenic determinants of the desired antigen and does not react with other polypeptides or binds at much lower affinity ($K_d > 10^{-6}$). Antibodies include, but are not limited to, polyclonal, monoclonal, chimeric, dAb (domain antibody), single chain, $F_{ab}$, $F_{ab'}$ and $F_{(ab')2}$ fragments, scFvs, and an $F_{ab}$ expression library.

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. In general, antibody molecules obtained from humans relate to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain.

The term "monoclonal antibody" (MAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs contain an antigen binding site capable of immunoreacting with a particular epitope of the antigen characterized by a unique binding affinity for it.

The term "antigen-binding site," or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." The assignment of amino acids to each domain is in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987), Chothia et al. Nature 342:878-883 (1989).

As used herein, the term "epitope" includes any protein determinant capable of specific binding to an immunoglobulin, an scFv, or a T-cell receptor. The term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. For example, antibodies may be raised against N-terminal or C-terminal peptides of a polypeptide. An antibody is said to specifically bind an antigen when the dissociation constant is $\leq 1$ μM; preferably $\leq 100$ nM and most preferably $\leq 10$ nM.

As used herein, the terms "immunological binding," and "immunological binding properties" refer to the non-covalent interactions of the type which occur between an immunoglobulin molecule and an antigen for which the immunoglobulin is specific. The strength, or affinity of immunological binding interactions can be expressed in terms of the dissociation constant (IQ) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (See Nature 361:186-87 (1993)). The ratio of $K_{off}/K_{on}$ enables the cancellation of all parameters not related to affinity, and is equal to the dissociation constant $K_d$. (See, generally, Davies et al. (1990) Annual Rev Biochem 59:439-473). An antibody of the present invention is said to specifically bind to the Toll-like Receptor 4 (TLR4)/MD-2 complex or to TLR4 when not complexed to MD-2, when the equilibrium binding constant ($K_d$) is $\leq 1$ μM, preferably $\leq 100$ nM, more preferably $\leq 10$ nM, and most preferably $\leq 100$ pM to about 1 pM, as measured by assays such as radioligand binding assays or similar assays known to those skilled in the art.

The term "isolated polynucleotide" as used herein shall mean a polynucleotide of genomic, cDNA, or synthetic origin or some combination thereof, which by virtue of its origin the "isolated polynucleotide" (1) is not associated with all or a portion of a polynucleotide in which the "isolated polynucleotide" is found in nature, (2) is operably linked to a polynucleotide which it is not linked to in nature, or (3) does not occur in nature as part of a larger sequence. Polynucleotides in accordance with the invention include the nucleic acid molecules encoding the heavy chain immunoglobulin molecules presented in SEQ ID NOS: 2, 12, 22, 32, 41, 42, 45, 47 and 48, and nucleic acid molecules encoding the light chain immunoglobulin molecules represented in SEQ ID NOS: 7, 17, 27, 37, 43, 44, 46 and 53.

The term "isolated protein" referred to herein means a protein of cDNA, recombinant RNA, or synthetic origin or some combination thereof, which by virtue of its origin, or source of derivation, the "isolated protein" (1) is not associated with proteins found in nature, (2) is free of other proteins from the same source, e.g., free of marine proteins, (3) is expressed by a cell from a different species, or (4) does not occur in nature.

The term "polypeptide" is used herein as a generic term to refer to native protein, fragments, or analogs of a polypeptide sequence. Hence, native protein fragments, and analogs are species of the polypeptide genus. Polypeptides in accordance with the invention comprise the heavy chain immunoglobulin molecules represented in SEQ ID NOS: 2, 12, 22, 32, 41, 42, 45, 47 and 48, and the light chain immunoglobulin molecules represented in SEQ ID NOS: 7, 17, 27, 37, 43, 44, 46 and 49, as well as antibody molecules formed by combinations comprising the heavy chain immunoglobulin molecules with light chain immunoglobulin molecules, such as kappa light chain immunoglobulin molecules, and vice versa, as well as fragments and analogs thereof.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally-occurring.

The term "operably linked" as used herein refers to positions of components so described are in a relationship permitting them to function in their intended manner. A control sequence "operably linked" to a coding sequence is ligated in such a way that expression of the coding sequence is achieved under conditions compatible with the control sequences.

The term "control sequence" as used herein refers to polynucleotide sequences which are necessary to effect the expression and processing of coding sequences to which they are ligated. The nature of such control sequences differs depending upon the host organism in prokaryotes, such control sequences generally include promoter, ribosomal binding site, and transcription termination sequence in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences. The term "polynucleotide" as referred to herein means a polymeric boron of nucleotides of at least 10 bases in length, either ribonucleotides or deoxynucleotides or a modified form of either type of nucleotide. The term includes single and double stranded forms of DNA.

The term oligonucleotide referred to herein includes naturally occurring, and modified nucleotides linked together by naturally occurring, and non-naturally occurring oligonucleotide linkages. Oligonucleotides are a polynucleotide subset generally comprising a length of 200 bases or fewer. Preferably oligonucleotides are 10 to 60 bases in length and most preferably 12, 13, 14, 15, 16, 17, 18, 19, or 20 to 40 bases in length. Oligonucleotides are usually single stranded, e.g., for probes, although oligonucleotides may be double stranded, e.g., for use in the construction of a gene mutant. Oligonucleotides of the invention are either sense or antisense oligonucleotides.

The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes Oligonucleotides linkages such as phosphorothioate, phosphorodithioate, phosphoroselerloate, phosphorodiselenoate, phosphoroanilothioate, phoshoraniladate, phosphoronmidate, and the like. See e.g., LaPlanche et al. Nucl. Acids Res. 14:9081 (1986); Stec et al. J. Am. Chem. Soc. 106:6077 (1984), Stein et al. Nucl. Acids Res. 16:3209 (1988), Zon et al. Anti Cancer Drug Design 6:539 (1991); Zon et al. Oligonucleotides and Analogues: A Practical Approach, pp. 87-108 (F. Eckstein, Ed., Oxford University Press, Oxford England (1991)); Stec et al. U.S. Pat. No. 5,151,510; Uhlmann and Peyman Chemical Reviews 90:543 (1990). An oligonucleotide can include a label for detection, if desired.

The term "selectively hybridize" referred to herein means to detectably and specifically bind. Polynucleotides, oligonucleotides and fragments thereof in accordance with the invention selectively hybridize to nucleic acid strands under hybridization and wash conditions that minimize appreciable amounts of detectable binding to nonspecific nucleic acids. High stringency conditions can be used to achieve selective hybridization conditions as known in the art and discussed herein. Generally, the nucleic acid sequence homology between the polynucleotides, oligonucleotides, and fragments of the invention and a nucleic acid sequence of interest will be at least 80%, and more typically with preferably increasing homologies of at least 85%, 90%, 95%, 99%, and 100%. Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching gap lengths of 5 or less are preferred with 2 or less being more preferred. Alternatively and preferably, two protein sequences (or polypeptide sequences derived from them of at least 30 amino acids in length) are homologous, as this term is used herein, if they have an alignment score of at more than 5 (in standard deviation units) using the program ALIGN with the mutation data matrix and a gap penalty of 6 or greater. See Dayhoff, M. O., in Atlas of Protein Sequence and Structure, pp. 101-110 (Volume 5, National Biomedical Research Foundation (1972)) and Supplement 2 to this volume, pp. 1-10. The two sequences or parts thereof are more preferably homologous if their amino acids are greater than or equal to 50% identical when optimally aligned using the ALIGN program. The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The following terms are used to describe the sequence relationships between two or more polynucleotide or amino acid sequences: "reference sequence", "comparison window", "sequence identity", "percentage of sequence identity", and "substantial identity". A "reference sequence" is a defined sequence used as a basis for a sequence comparison a reference sequence may be a subset of a larger sequence, for example, as a segment of a full-length cDNA or gene sequence given in a sequence listing or may comprise a complete cDNA or gene sequence. Generally, a reference sequence is at least 18 nucleotides or 6 amino acids in length, frequently at least 24 nucleotides or 8 amino acids in length, and often at least 48 nucleotides or 16 amino acids in length. Since two polynucleotides or amino acid sequences may each (1) comprise a sequence (i.e., a portion of the complete polynucleotide or amino acid sequence) that is similar between the two molecules, and (2) may further comprise a sequence that is divergent between the two polynucleotides or amino acid sequences, sequence comparisons between two (or more) molecules are typically performed by comparing sequences of the two molecules over a "comparison window" to identify and compare local regions of sequence similarity. A "comparison window", as used herein, refers to a conceptual segment of at least 18 contiguous nucleotide positions or 6 amino acids wherein a polynucleotide sequence or amino acid sequence may be compared to a reference sequence of at least 18 contiguous nucleotides or 6 amino acid sequences and wherein the portion of the polynucleotide sequence in the comparison window may comprise additions, deletions, substitutions, and the like (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman Adv. Appl. Math. 2:482 (1981), by the homology alignment algorithm of Needleman and Wunsch J. Mol. Biol. 48:443 (1970), by the search for similarity method of Pearson and Lipman Proc. Natl. Acad. Sci. (U.S.A.) 85:2444 (1988), by computerized implementations of these algorithms (GAP, BESTFIT, FASTA, and TFASTA in the Wisconsin Genetics Software Package Release 7.0, (Genetics Computer Group, 575 Science Dr., Madison, Wis.), Geneworks, or MacVector software packages), or by inspection, and the best alignment (i.e., resulting in the highest percentage of homology over the comparison window) generated by the various methods is selected.

The term "sequence identity" means that two polynucleotide or amino acid sequences are identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T, C, G, U or I) or residue occurs in both sequences to yield the number of matched positions, dividing the number of matched positions by the total number of positions in the comparison window (i.e., the window size), and multiplying the result by 100 to yield the percentage of sequence identity. The terms "substantial identity" as used herein denotes a characteristic of a polynucleotide or amino acid sequence, wherein the polynucleotide or amino acid comprises a sequence that has at least 85 percent sequence identity, preferably at least 90 to 95 percent sequence identity, more usually at least 99 percent sequence identity as compared to a reference sequence over a comparison window of at least 18 nucleotide (6 amino acid) positions, frequently over a window of at least 24-48 nucleotide (8-16 amino acid) positions, wherein the percentage of sequence identity is calculated by comparing the reference sequence to the sequence which may include deletions or additions which total 20 percent or less of the reference sequence over the comparison window. The reference sequence may be a subset of a larger sequence.

As used herein, the twenty conventional amino acids and their abbreviations follow conventional usage. See Immunology—A Synthesis (2nd Edition, E. S. Golub and D. R. Gren, Eds., Sinauer Associates, Sunderland Mass. (1991)). Stereoisomers (e.g., D-amino acids) of the twenty conventional amino acids, unnatural amino acids such as α-,α-disubstituted amino acids, N-alkyl amino acids, lactic acid, and other unconventional amino acids may also be suitable components for polypeptides of the present invention. Examples of unconventional amino acids include: 4 hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

Similarly, unless specified otherwise, the left-hand end of single-stranded polynucleotide sequences is the 5' end the left-hand direction of double-stranded polynucleotide sequences is referred to as the 5' direction. The direction of 5' to 3' addition of nascent RNA transcripts is referred to as the transcription direction sequence regions on the DNA strand having the same sequence as the RNA and which are 5' to the 5' end of the RNA transcript are referred to as "upstream sequences", sequence regions on the DNA strand having the same sequence as the RNA and which are 3' to the 3' end of the RNA transcript are referred to as "downstream sequences".

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity, and most preferably at least 99 percent sequence identity.

Preferably, residue positions which are not identical differ by conservative amino acid substitutions.

Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine valine, glutamic-aspartic, and asparagine-glutamine.

As discussed herein, minor variations in the amino acid sequences of antibodies or immunoglobulin molecules are contemplated as being encompassed by the present invention, providing that the variations in the amino acid sequence maintain at least 75%, more preferably at least 80%, 90%, 95%, and most preferably 99%. In particular, conservative amino acid replacements are contemplated. Conservative replacements are those that take place within a family of amino acids that are related in their side chains. Genetically encoded amino acids are generally divided into families: (1) acidic amino acids are aspartate, glutamate; (2) basic amino acids are lysine, arginine, histidine; (3) non-polar amino acids are alanine, valine, leucine, isoleucine, proline, phenylalanine, methionine, tryptophan, and (4) uncharged polar amino acids are glycine, asparagine, glutamine, cysteine, serine, threonine, tyrosine. The hydrophilic amino acids include arginine, asparagine, aspartate, glutamine, glutamate, histidine, lysine, serine, and threonine. The hydrophobic amino acids include alanine, cysteine, isoleucine, leucine, methionine, phenylalanine, proline, tryptophan, tyrosine and valine. Other families of amino acids include (i) serine and threonine, which are the aliphatic-hydroxy family; (ii) asparagine and glutamine, which are the amide containing family; (iii) alanine, valine, leucine and isoleucine, which are the aliphatic family; and (iv) phenylalanine, tryptophan, and tyrosine, which are the aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al. Science 253:164 (1991). Thus, the foregoing examples demonstrate that those of skill in the art can recognize sequence motifs and structural conformations that may be used to define structural and functional domains in accordance with the invention.

Preferred amino acid substitutions are those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et at. Nature 354:105 (1991).

The term "polypeptide fragment" as used herein refers to a polypeptide that has an amino terminal and/or carboxy-terminal deletion, but where the remaining amino acid sequence is identical to the corresponding positions in the naturally-occurring sequence deduced, for example, from a full length cDNA sequence. Fragments typically are at least 5, 6, 8 or 10 amino acids long, preferably at least 14 amino acids long' more preferably at least 20 amino acids long, usually at least 50 amino acids long, and even more preferably at least 70 amino acids long. The term "analog" as used herein refers to polypeptides which are comprised of a segment of at least 25 amino acids that has substantial identity to a portion of a deduced amino acid sequence and which has specific binding to TLR4/MD2 complex or TLR4 alone, under suitable binding conditions. Typically, polypeptide analogs comprise a conservative amino acid substitution (or addition or deletion) with respect to the naturally-occurring sequence. Analogs typically are at least 20 amino acids long, preferably at least 50 amino acids long or longer, and can often be as long as a full-length naturally-occurring polypeptide.

Peptide analogs are commonly used in the pharmaceutical industry as non-peptide drugs with properties analogous to those of the template peptide. These types of non-peptide compound are termed "peptide mimetics" or "peptidomimetics". Fauchere, J. Adv. Drug Res. 15:29 (1986), Veber and Freidinger TINS p. 392 (1985); and Evans et al. J. Med. Chem. 30:1229 (1987). Such compounds are often developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from the group consisting of: —$CH_2NH$—, —$CH_2S$—, —$CH_2$—$CH_2$—, —CH=CH—(cis and trans), —$COCH_2$—, $CH(OH)CH_2$—, and —$CH_2SO$—, by methods well known in the art. Systematic substitution of one or more amino acids of a consensus sequence with a D-amino acid of the same type (e.g., D-lysine in place of L-lysine) may be used to generate more stable peptides. In addition, constrained peptides comprising a consensus sequence or a substantially identical consensus sequence variation may be generated by methods known in the art (Rizo and Gierasch Ann. Rev. Biochem. 61:387 (1992)); for example, by adding internal cysteine residues capable of forming intramolecular disulfide bridges which cyclize the peptide.

The term "agent" is used herein to denote a chemical compound, a mixture of chemical compounds, a biological macromolecule, or an extract made from biological materials.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). In certain situations, the label or marker can also be therapeutic. Various methods of labeling polypeptides and glycoproteins are known in the art and may be used. Examples of labels for polypeptides include, but are not limited to, the following: radioisotopes or radionuclides (e.g., $^3H$, $^{14}C$, $^{15}N$, $^{35}S$, $^{90}Y$, $^{99}Tc$, $^{111}In$, $^{125}I$, $^{131}I$), fluorescent labels (e.g., FITC, rhodamine, lanthanide phosphors), enzymatic labels (e.g., horseradish peroxidase, p-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance. The term "pharmaceutical agent or drug" as used herein refers to a chemical compound or composition capable of inducing a desired therapeutic effect when properly administered to a patient.

Other chemistry terms herein are used according to conventional usage in the art, as exemplified by The McGraw-Hill Dictionary of Chemical Terms (Parker, S., Ed., McGraw-Hill, San Francisco (1985)).

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present.

Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

The term patient "includes" human and veterinary subjects.

Antibodies

Monoclonal antibodies of the invention (e.g., murine monoclonal or humanized antibodies) have the ability to inhibit LPS-induced proinflammatory cytokine production. Inhibition is determined, for example, in the human whole blood and huTLR4/MD2 transfected HEK 293 cellular assays described herein. Exemplary monoclonal antibodies include, for example, the antibodies referred to herein as murine 18H10 monoclonal antibody ("mu18H10"), human 18H10 monoclonal antibody ("hu18H10"), murine 16G7 monoclonal antibody ("mu16G7"), murine 15C1 monoclonal antibody ("mu15C1"), human 15C1 monoclonal antibody ("hu15C1"), murine 7E3 monoclonal antibody ("mu7E3") and human 7E3 monoclonal antibody ("hu7E3"). The mu18H10 and hu18H10 antibodies recognize the TLR4/MD-2 complex, but do not recognize an MD-2 protein when not complexed with TLR4. The mu16G7, mu15C1, hu15C1, mu7E3 and hu7E3 monoclonal antibodies recognize the TLR4/MD-2 complex. mu15C1, hu15C1 and 16G7 also recognize TLR4 when not complexed with MD-2. Other exemplary antibodies include monoclonal antibodies that recognize TLR2, MD-2 or CD14, such as the anti-CD14 monoclonal antibody known as "28C5" and the anti-TLR2 monoclonal antibody known as "T2.5".

Also included in the invention are antibodies that bind to the same epitope as the antibodies described herein. For example, antibodies of the invention immunospecifically bind a TLR4/MD-2 complex, wherein the antibody binds to an epitope that includes one or more amino acid residues on human TLR4 between residues 289 and 375 of SEQ ID NO:61. Antibodies of the invention immunospecifically bind the TLR4/MD2 complex, wherein the antibody binds to an epitope on human MD-2 between residues 19 and 57 of SEQ ID NO:60. For antibodies that bind TLR2, the antibody or a portion of a multivalent antibody binds to an epitope in the C-terminal portion of the extracellular domain of TLR2 (i.e., TLR2ECD).

Those skilled in the art will recognize that it is possible to determine, without undue experimentation, if a monoclonal antibody (e.g., a murine monoclonal or humanized antibody) has the same specificity as a monoclonal antibody described herein (e.g., mu18H10, hu18H10, mu16G7, mu15C1, hu15C1, mu7E3, hu7E3, 28C5 and/or T2.5) by ascertaining whether the former prevents the latter from binding to the antibody target, e.g., the TLR4/MD-2 complex, TLR4 when not complexed to MD-2, MD-2 when complexed with TLR4, MD-2 when not complexed to TLR4, TLR2 and CD14. If the monoclonal antibody being tested competes with the monoclonal antibody of the invention, as shown by a decrease in binding by the monoclonal antibody of the invention, then the two monoclonal antibodies bind to the same, or a closely related, epitope. An alternative method for determining whether a monoclonal antibody has the specificity of monoclonal antibody of the invention is to pre-incubate the monoclonal antibody of the invention with the TLR4/MD-2 complex or a soluble TLR4 protein (with which it is normally reactive), and then add the monoclonal antibody being tested to determine if the monoclonal antibody being tested is inhibited in its ability to bind the target, e.g., TLR4/MD-2 complex, TLR4, MD-2, TLR2 or CD14. If the monoclonal antibody being tested is inhibited then, in all likelihood, it has the same, or functionally equivalent, epitopic specificity as the monoclonal antibody of the invention. Screening of monoclonal antibodies of the invention, can be also carried out by measuring LPS-induced IL-8 production and determining whether the test monoclonal antibody is able to neutralize LPS-induced IL-8 production. Screening can also be carried out by measuring $PAM_3CSK_4$-induced IL-6 production and determining whether the test monoclonal antibody is able to neutralize $PAM_3CSK_4$-induced IL-6 production.

Various procedures known within the art may be used for the production of polyclonal or monoclonal antibodies directed against the TLR4/MD-2 complex, TLR4 when not complexed to MD-2, MD-2, TLR2 or CD14 or against derivatives, fragments, analogs homologs or orthologs thereof. (See, e.g., Antibodies: A Laboratory Manual, Harlow E, and Lane D, 1988, Cold Spring Harbor Laboratory Press, Cold Spring Harbor, N.Y., incorporated herein by reference).

Antibodies are purified by well-known techniques, such as affinity chromatography using protein A or protein G, which provide primarily the IgG fraction of immune serum. Subsequently, or alternatively, the specific antigen which is the target of the immunoglobulin sought, or an epitope thereof, may be immobilized on a column to purify the immune specific antibody by immunoaffinity chromatography. Purification of immunoglobulins is discussed, for example, by D. Wilkinson (The Scientist, published by The Scientist, Inc., Philadelphia Pa., Vol. 14, No. 8 (Apr. 17, 2000), pp. 25-28).

The antibodies of the invention (e.g., hu18H10, 16G7, hu15C1 and hu7E3) are monoclonal antibodies. Monoclonal antibodies that neutralize LPS-signaling that is mediated by the TLR4/MD-2 complex are generated, e.g., by immunizing BALB/c mice with combinations of cell transfectants expressing high levels of TLR4 and MD-2 on their surface and a recombinant soluble chimeric protein comprising both TLR4 and MD-2 tethered by a flexible linker sequence. Hybridomas resulting from myeloma/B cell fusions are then screened for reactivity to this TLR4/MD-2 complex.

Monoclonal antibodies are prepared, for example, using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

The immunizing agent will typically include the protein antigen, a fragment thereof or a fusion protein thereof. Generally, either peripheral blood lymphocytes are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, *Monoclonal Antibodies: Principles and Practice*, Academic Press, (1986) pp. 59-103). Immortalized cell lines are usually transformed mammalian cells, particularly myeloma cells of rodent, bovine and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of monoclonal antibodies. (See Kozbor, J. Immunol., 133:3001 (1984); Brodeur et al., Monoclonal Antibody Production Techniques and Applications, Marcel Dekker, Inc., New York, (1987) pp. 51-63)).

The culture medium in which the hybridoma cells are cultured can then be assayed for the presence of monoclonal antibodies directed against the antigen. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, Anal. Biochem., 107:220 (1980). Moreover, in therapeutic applications of monoclonal antibodies, it is important to identify antibodies having a high degree of specificity and a high binding affinity for the target antigen.

After the desired hybridoma cells are identified, the clones can be subcloned by limiting dilution procedures and grown by standard methods. (See Goding, *Monoclonal Antibodies: Principles and Practice*, Academic Press, (1986) pp. 59-103). Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

Monoclonal antibodies can also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (see U.S. Pat. No. 4,816,567; Morrison, Nature 368, 812-13 (1994)) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

Monoclonal antibodies of the invention include humanized antibodies or human antibodies. These antibodies are suitable for administration to humans without engendering an immune response by the human against the administered immunoglobulin. Humanized forms of antibodies are chimeric immunoglobulins, immunoglobulin chains or fragments thereof (such as Fv, Fab, Fab', F(ab')$_2$ or other antigen-binding subsequences of antibodies) that are principally comprised of the sequence of a human immunoglobulin, and contain minimal sequence derived from a non-human immunoglobulin. Humanization is performed, e.g., by following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody. (See also U.S. Pat. No. 5,225,539.) In some instances, Fv framework residues of the human immunoglobulin are replaced by corresponding non-human residues. Humanized antibodies also comprise, e.g., residues which are found neither in the recipient antibody nor in the imported CDR or framework sequences. In general, the humanized antibody includes substantially all of at least one, and typically two, variable domains, in which all or substantially all of the CDR regions correspond to those of a non-human immunoglobulin and all or substantially all of the framework regions are those of a human immunoglobulin consensus sequence. The humanized antibody optimally also includes at least a portion of an immunoglobulin constant region (Fc), typically that of a human immunoglobulin (Jones et al., 1986; Riechmann et al., 1988; and Presta, Curr. Op. Struct. Biol., 2:593-596 (1992)).

Fully human antibodies are antibody molecules in which the entire sequence of both the light chain and the heavy chain, including the CDRs, arise from human genes. Such antibodies are termed "human antibodies", or "fully human antibodies" herein. Monoclonal antibodies can be prepared by using trioma technique; the human B-cell hybridoma technique (see Kozbor, et al., 1983 Immunol Today 4: 72); and the EBV hybridoma technique to produce monoclonal antibodies (see Cole, et al., 1985 In: MONOCLONAL ANTIBODIES AND CANCER THERAPY, Alan R. Liss, Inc., pp. 77-96). Monoclonal antibodies may be utilized and may be produced by using human hybridomas (see Cote, et al., 1983. Proc Natl Acad Sci USA 80: 2026-2030) or by transforming human B-cells with Epstein Barr Virus in vitro (see Cole, et al., 1985 In: MONOCLONAL ANTIBODIES AND CANCER THERAPY, Alan R. Liss, Inc., pp. 77-96).

In addition, human antibodies can also be produced using additional techniques, including phage display libraries. (See Hoogenboom and Winter, J. Mol. Biol., 227:381 (1991); Marks et al., J. Mol. Biol., 222:581 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in Marks et al., Bio/Technology 10, 779-783 (1992); Lonberg et al., Nature 368 856-859 (1994); Morrison, Nature 368, 812-13 (1994); Fishwild et al, Nature Biotechnology 14, 845-51 (1996); Neuberger, Nature Biotechnology 14, 826 (1996); and Lonberg and Huszar, Intern. Rev. Immunol. 13 65-93 (1995).

Human antibodies may additionally be produced using transgenic nonhuman animals which are modified so as to produce fully human antibodies rather than the animal's endogenous antibodies in response to challenge by an antigen. (See PCT publication WO94/02602). The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. An example of such a nonhuman animal is a mouse termed the Xenomouse™ as disclosed in PCT publications WO 96/33735 and WO 96/34096. This animal produces B cells which secrete fully human immunoglobulins. The antibodies can be obtained directly from the animal after immunization with an immunogen of interest, as, for example, a preparation of a polyclonal antibody, or alternatively from immortalized B cells derived from the animal, such as hybridomas producing monoclonal antibodies. Additionally, the genes encoding the immunoglobulins with human variable regions can be recovered and expressed to obtain the antibodies directly, or can be further modified to obtain analogs of antibodies such as, for example, single chain Fv (scFv) molecules.

An example of a method of producing a nonhuman host, exemplified as a mouse, lacking expression of an endogenous immunoglobulin heavy chain is disclosed in U.S. Pat. No. 5,939,598. It can be obtained by a method, which includes deleting the J segment genes from at least one endogenous heavy chain locus in an embryonic stem cell to prevent rearrangement of the locus and to prevent formation of a transcript of a rearranged immunoglobulin heavy chain locus, the deletion being effected by a targeting vector containing a gene encoding a selectable marker; and producing from the embryonic stem cell a transgenic mouse whose somatic and germ cells contain the gene encoding the selectable marker.

One method for producing an antibody of interest, such as a human antibody, is disclosed in U.S. Pat. No. 5,916,771. This method includes introducing an expression vector that contains a nucleotide sequence encoding a heavy chain into one mammalian host cell in culture, introducing an expression vector containing a nucleotide sequence encoding a light chain into another mammalian host cell, and fusing the two cells to form a hybrid cell. The hybrid cell expresses an antibody containing the heavy chain and the light chain.

In a further improvement on this procedure, a method for identifying a clinically relevant epitope on an immunogen, and a correlative method for selecting an antibody that binds immunospecifically to the relevant epitope with high affinity, are disclosed in PCT publication WO 99/53049.

The antibody can be expressed by a vector containing a DNA segment encoding the single chain antibody described above.

These can include vectors, liposomes, naked DNA, adjuvant-assisted DNA, gene gun, catheters, etc. Vectors include chemical conjugates such as described in WO 93/64701, which has targeting moiety (e.g. a ligand to a cellular surface receptor), and a nucleic acid binding moiety (e.g. polylysine), viral vector (e.g. a DNA or RNA viral vector), fusion proteins such as described in PCT/US 95/02140 (WO 95/22618) which is a fusion protein containing a target moiety (e.g. an antibody specific for a target cell) and a nucleic acid binding moiety (e.g. a protamine), plasmids, phage, etc. The vectors can be chromosomal, non-chromosomal or synthetic.

Preferred vectors include viral vectors, fusion proteins and chemical conjugates. Retroviral vectors include moloney murine leukemia viruses. DNA viral vectors are preferred. These vectors include pox vectors such as orthopox or avipox vectors, herpesvirus vectors such as a herpes simplex I virus (HSV) vector (see Geller, A. I. et al., J. Neurochem, 64:487 (1995); Lim, F., et al., in DNA Cloning: Mammalian Systems, D. Glover, Ed. (Oxford Univ. Press, Oxford England) (1995); Geller, A. I. et al., Proc Natl. Acad. Sci.: U.S.A. 90:7603 (1993); Geller, A. I., et al., Proc Natl. Acad. Sci. USA 87:1149 (1990), Adenovirus Vectors (see LeGal LaSalle et al., Science, 259:988 (1993); Davidson, et al., Nat. Genet. 3:219 (1993); Yang, et al., J. Virol. 69:2004 (1995) and Adeno-associated Virus Vectors (see Kaplitt, M. G. et al., Nat. Genet. 8:148 (1994).

Pox viral vectors introduce the gene into the cells cytoplasm. Avipox virus vectors result in only a short term expression of the nucleic acid. Adenovirus vectors, adeno-associated virus vectors and herpes simplex virus (HSV) vectors are preferred for introducing the nucleic acid into neural cells. The adenovirus vector results in a shorter term expression (about 2 months) than adeno-associated virus (about 4 months), which in turn is shorter than HSV vectors. The particular vector chosen will depend upon the target cell and the condition being treated. The introduction can be by standard techniques, e.g. infection, transfection, transduction or transformation. Examples of modes of gene transfer include e.g., naked DNA, $CaPO_4$ precipitation, DEAE dextran, electroporation, protoplast fusion, lipofection, cell microinjection, and viral vectors.

The vector can be employed to target essentially any desired target cell. For example, stereotaxic injection can be used to direct the vectors (e.g. adenovirus, HSV) to a desired location. Additionally, the particles can be delivered by intracerebroventricular (icv) infusion using a minipump infusion system, such as a SynchroMed® Infusion System. A method based on bulk flow, termed convection, has also proven effective at delivering large molecules to extended areas of the brain and may be useful in delivering the vector to the target cell. (See Bobo et al., Proc. Natl. Acad. Sci. USA 91:2076-2080 (1994); Morrison et al., Am. J. Physiol. 266: 292-305 (1994)). Other methods that can be used include catheters, intravenous, parenteral, intraperitoneal and subcutaneous injection, and oral or other known routes of administration.

These vectors can be used to express large quantities of antibodies that can be used in a variety of ways. For example, to detect the presence of the TLR4/MD-2 complex, or another target such as TLR4, MD2, TLR2 and/or CD14 in a sample. The antibody can also be used to try to bind to and disrupt signaling that is related to, mediated by or modulated by the TLR4/MD2 complex, TLR2 and/or CD14.

Techniques can be adapted for the production of single-chain antibodies specific to an antigenic protein of the invention (see e.g., U.S. Pat. No. 4,946,778). In addition, methods can be adapted for the construction of $F_{ab}$ expression libraries (see e.g., Huse, et al., 1989 Science 246: 1275-1281) to allow rapid and effective identification of monoclonal $F_{ab}$ fragments with the desired specificity for a protein or derivatives, fragments, analogs or homologs thereof. Antibody fragments that contain the idiotypes to a protein antigen may be produced by techniques known in the art including, but not limited to: (i) an $F_{(ab')2}$ fragment produced by pepsin digestion of an antibody molecule; (ii) an $F_{ab}$ fragment generated by reducing the disulfide bridges of an $F_{(ab')2}$ fragment; (iii) an $F_{ab}$ fragment generated by the treatment of the antibody molecule with papain and a reducing agent and (iv) $F_v$ fragments.

The invention also includes $F_v$, $F_{ab}$, $F_{ab'}$ and $F_{(ab')2}$ anti-TLR4/MD2 complex fragments, anti-TLR4 fragments, anti-MD2 fragments, anti-TLR2 fragments, anti-CD14, single chain antibodies that recognize and bind TLR4/MD2 complex, TLR4, MD2, TLR2 and/or CD14, bispecific antibodies that recognize and bind TLR4/MD2 complex, TLR4, MD2, TLR2 and/or CD14 and heteroconjugate antibodies that recognize and bind TLR4/MD2 complex, TLR4, MD2, TLR2 and/or CD14.

Bispecific antibodies are antibodies that have binding specificities for at least two different antigens. In the present case, one of the binding specificities is for the TLR4/MD2 complex, TLR4, MD-2, TLR2 or CD14. The second binding target is any other antigen, and advantageously is a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, Nature, 305:537-539 (1983)). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., EMBO J., 10:3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, e.g., Suresh et al., Methods in Enzymology, 121:210 (1986).

According to another approach described in WO 96/27011, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies can be prepared as full length antibodies or antibody fragments (e.g. F(ab')$_2$ bispecific antibodies). Techniques for generating bispecific antibodies from antibody fragments have been described in the literature. For example, bispecific antibodies can be prepared using chemical linkage. Brennan et al., Science 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Additionally, Fab' fragments can be directly recovered from *E. coli* and chemically coupled to form bispecific antibodies. Shalaby et al., J. Exp. Med. 175:217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., J. Immunol. 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, Gruber et al., J. Immunol. 152:5368 (1994).

Antibodies with more than two valencies are contemplated. For example, trispecific antibodies can be prepared. Tutt et al., J. Immunol. 147:60 (1991).

Exemplary bispecific antibodies can bind to two different epitopes, at least one of which originates in the protein antigen of the invention. Alternatively, an anti-antigenic arm of an immunoglobulin molecule can be combined with an arm which binds to a triggering molecule on a leukocyte such as a T-cell receptor molecule (e.g. CD2, CD3, CD28, or B7), or Fc receptors for IgG (FcγR), such as FcγRI (CD64), Fc-γRII (CD32) and FcγRIII (CD16) so as to focus cellular defense mechanisms to the cell expressing the particular antigen. Bispecific antibodies can also be used to direct cytotoxic agents to cells which express a particular antigen. These antibodies possess an antigen-binding arm and an arm which binds a cytotoxic agent or a radionuclide chelator, such as EOTUBE, DPTA, DOTA, or TETA. Another bispecific antibody of interest binds the protein antigen described herein and further binds tissue factor (TF).

Heteroconjugate antibodies are also within the scope of the present invention. Heteroconjugate antibodies are composed of two covalently joined antibodies. Such antibodies have, for example, been proposed to target immune system cells to unwanted cells (see U.S. Pat. No. 4,676,980), and for treatment of HIV infection (see WO 91/00360; WO 92/200373; EP 03089). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

It can be desirable to modify the antibody of the invention with respect to effector function, so as to enhance, e.g., the effectiveness of the antibody in treating diseases and disorders associated with aberrant LPS signaling. For example, cysteine residue(s) can be introduced into the Fc region, thereby allowing interchain disulfide bond formation in this region. The homodimeric antibody thus generated can have improved internalization capability and/or increased complement-mediated cell killing and antibody-dependent cellular cytotoxicity (ADCC). (See Caron et al., J. Exp Med., 176: 1191-1195 (1992) and Shopes, J. Immunol., 148: 2918-2922 (1992)). Alternatively, an antibody can be engineered that has dual Fc regions and can thereby have enhanced complement lysis and ADCC capabilities. (See Stevenson et al., Anti-Cancer Drug Design, 3: 219-230 (1989)).

The invention also pertains to immunoconjugates comprising an antibody conjugated to a cytotoxic agent such as a toxin (e.g., an enzymatically active toxin of bacterial, fungal, plant, or animal origin, or fragments thereof), or a radioactive isotope (i.e., a radioconjugate).

Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutaredehyde), bis-azido compounds (such as bis (p-azidobenzoyl) hexanediamine), bis-diazonium derivatives (such as bis-(p- diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. (See WO94/11026).

Those of ordinary skill in the art will recognize that a large variety of possible moieties can be coupled to the resultant antibodies of the invention. (See, e.g., "Conjugate Vaccines", Contributions to Microbiology and Immunology, J. M. Cruse and R. E. Lewis, Jr (eds), Carger Press, New York, (1989), the entire contents of which are incorporated herein by reference).

Coupling may be accomplished by any chemical reaction that will bind the two molecules so long as the antibody and the other moiety retain their respective activities. This linkage can include many chemical mechanisms, for instance covalent binding, affinity binding, intercalation, coordinate binding and complexation. The preferred binding is, however, covalent binding. Covalent binding can be achieved either by direct condensation of existing side chains or by the incorporation of external bridging molecules. Many bivalent or polyvalent linking agents are useful in coupling protein molecules, such as the antibodies of the present invention, to other molecules. For example, representative coupling agents can include organic compounds such as thioesters, carbodiimides, succinimide esters, diisocyanates, glutaraldehyde, diazobenzenes and hexamethylene diamines. This listing is not intended to be exhaustive of the various classes of coupling agents known in the art but, rather, is exemplary of the more common coupling agents. (See Killen and Lindstrom, Jour. Immun. 133:1335-2549 (1984); Jansen et al., Immunological Reviews 62:185-216 (1982); and Vitetta et al., Science 238: 1098 (1987).

Preferred linkers are described in the literature. (See, e.g., Ramakrishnan, S. et al., Cancer Res. 44:201-208 (1984) describing use of MBS (M-maleimidobenzoyl-N-hydroxysuccinimide ester). See also, U.S. Pat. No. 5,030,719, describing use of halogenated acetyl hydrazide derivative coupled to an antibody by way of an oligopeptide linker. Particularly preferred linkers include: (i) EDC (1-ethyl-3-(3-dimethylamino-propyl) carbodiimide hydrochloride; (ii) SMPT (4-succinimidyloxycarbonyl-alpha-methyl-alpha-(2-pridyl-dithio)-toluene (Pierce Chem. Co., Cat. (21558G); (iii) SPDP (succinimidyl-6 [3-(2-pyridyldithio) propionamido]hexanoate (Pierce Chem. Co., Cat #21651G); (iv) Sulfo-LC-SPDP (sulfosuccinimidyl 6 [3-(2-pyridyldithio)-propianamide] hexanoate (Pierce Chem. Co. Cat. #2165-G); and (v) sulfo-NHS(N-hydroxysulfo-succinimide: Pierce Chem. Co., Cat. #24510) conjugated to EDC.

The linkers described above contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

The antibodies disclosed herein can also be formulated as immunoliposomes. Liposomes containing the antibody are prepared by methods known in the art, such as described in Epstein et al., Proc. Natl. Acad. Sci. USA, 82: 3688 (1985); Hwang et al., Proc. Natl. Acad. Sci. USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., J. Biol. Chem., 257: 286-288 (1982) via a disulfide-interchange reaction.

Use of Antibodies Against the TLR4/MD2 Complex, TLR4, MD2, TLR2, CD14 and Combinations Thereof It will be appreciated that administration of therapeutic entities in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, Pa. (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2): 210-8 (2000), Wang W. "Lyophilization and development of solid protein pharmaceuticals." Int. J. Pharm. 203(1-2):1-60 (2000), Charman W N "Lipids, lipophilic drugs, and oral drug delivery-some emerging concepts." J Pharm Sci. 89(8):967-78 (2000), Powell et al., "Compendium of excipients for parenteral formulations" PDA J Pharm Sci Technol. 52:238-311 (1998) and the citations therein for additional information related to formulations, excipients and carriers well known to pharmaceutical chemists.

Therapeutic formulations of the invention, which include a monoclonal antibody of the invention (e.g., a murine monoclonal or humanized monoclonal antibody), are used to treat or alleviate a symptom associated with an immune-related disorder. The present invention also provides methods of treating or alleviating a symptom associated with an immune-related disorder. A therapeutic regimen is carried out by identifying a subject, e.g., a human patient suffering from (or at risk of developing) an immune-related disorder, using standard methods.

Antibodies of the invention, which are capable of inhibiting LPS-induced proinflammatory cytokine production, are useful therapeutic tools in the treatment of disorders, such as, for example, acute inflammation and sepsis induced by microbial products (e.g., LPS) and exacerbations arising from this acute inflammation, such as, for example, chronic obstructive pulmonary disease and asthma (see O'Neill, Curr. Opin. Pharmacol. 3: 396-403 (2003), hereby incorporated by reference in its entirety). Such antibodies are also useful in treating neurodegenerative autoimmune diseases. (Lehnardt et al., Proc. Natl. Acad. Sci. USA 100: 8514-8519 (2003), hereby incorporated by reference in its entirety).

In addition, the antibodies of the invention are also useful as therapeutic reagents in the treatment of diseases, such as, for example, osteoarthritis, which are caused by mechanical stress, which, in turn, induces endogenous soluble "stress" factors that trigger TLR4. Endogenous soluble stress factor include e.g., Hsp60 (see Ohashi et al., J. Immunol. 164: 558-561 (2000)) and fibronectin (see Okamura et al., J. Biol. Chem. 276: 10229-10233 (2001) and heparan sulphate, hyaluronan, gp96, β-Defensin-2 or surfactant protein A (see e.g., Johnson et al., Crit. Rev. Immunol., 23(1-2):15-44 (2003), each of which is hereby incorporated by reference in its entirety). The antibodies of the invention are also useful in the treatment of a variety of disorders associated with mechanical stress, such as for example, mechanical stress that is associated with subjects and patients placed on respirators, ventilators and other respiratory-assist devices. For example, the antibodies of the invention are useful in the treatment of ventilator-induced lung injury ("VILI"), also referred to as ventilation-associated lung injury ("VALI").

Other disease areas in which inhibiting TLR4/MD2, TLR4, MD2, TLR2 and/or CD14 function could be beneficial include, for example, chronic inflammation (e.g., chronic inflammation associated with allergic conditions and asthma), autoimmune diseases (e.g., inflammatory bowel disorder, rheumatoid arthritis, multiple sclerosis) and atherosclerosis (see O'Neill, Curr. Opin. Pharmacol. 3: 396-403 (2003), hereby incorporated by reference in its entirety).

Symptoms associated with these immune-related disorders include, for example, inflammation, fever, general malaise, fever, pain, often localized to the inflamed area, rapid pulse rate, joint pain or aches (arthralgia), rapid breathing or other abnormal breathing patterns, chills, confusion, disorientation, agitation, dizziness, cough, dyspnea, pulmonary infections, cardiac failure, respiratory failure, edema, weight gain, mucopurulent relapses, cachexia, wheezing, headache, and abdominal symptoms such as, for example, abdominal pain, diarrhea or constipation.

Efficaciousness of treatment is determined in association with any known method for diagnosing or treating the particular immune-related disorder. Alleviation of one or more symptoms of the immune-related disorder indicates that the antibody confers a clinical benefit.

Methods for the screening of antibodies that possess the desired specificity include, but are not limited to, enzyme linked immunosorbent assay (ELISA) and other immunologically mediated techniques known within the art.

Combinations of antibodies directed against the TLR4/MD-2 complex or to TLR4 when not complexed to MD-2 (or a fragment thereof), MD2 when not complexed to TLR4 (or a fragment thereof), TLR2 (or a fragment thereof), or CD14 (or a fragment thereof), or multispecific antibodies that recognize two or more targets selected from TLR4/MD2 complex, TLR4, MD2, TLR2 and CD14, may be used in methods known within the art relating to the localization and/or quantitation of these targets for use, e.g., in measuring levels of the targets within appropriate physiological samples, for use in diagnostic methods, for use in imaging the protein, and the like. In a given embodiment, combinations of antibodies specific to the TLR4/MD-2 complex, TLR4, MD2, TLR2 or CD14, or multispecific antibodies that recognize two or more of these targets, or a derivative, fragment, analog or homolog thereof, that contain the antibody derived antigen binding domain, are utilized as pharmacologically active compounds (referred to hereinafter as "Therapeutics").

Combinations of antibodies specific to the TLR4/MD2 complex, TLR4, MD2, TLR2 or CD14, or a multispecific antibody that recognizes at least two these targets, can be used to isolated TLR4/MD2 complex, TLR4, MD2, TLR2 and/or CD14 by standard techniques, such as immunoaffinity, chromatography or immunoprecipitation. Antibodies directed against TLR4/MD2 complex, TLR4, MD2, TLR2 and/or CD14 (or a fragment thereof) can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Antibodies described herein, including polyclonal, monoclonal, humanized and fully human antibodies, may be used in combinations as therapeutic agents. Such agents will generally be employed to treat or prevent a disease or pathology associated with aberrant TLR4, TLR2 or CD14-signaling in a subject. An antibody preparation, preferably one having high specificity and high affinity for its target antigen(s), is administered to the subject and will generally have an effect due to its binding with the target(s). Administration of the antibody or antibody combinations may abrogate or inhibit or interfere with the signaling function of the target (e.g., the TLR4/MD-2 complex, TLR2, CD14). Administration of the antibody may abrogate or inhibit or interfere with the binding of the target (e.g., TLR4) with an endogenous ligand (e.g., TLR4 or the MD-2 accessory protein) to which it naturally binds. For example, the antibody or antibody combination binds to the target and neutralizes LPS-induced or proinflammatory cytokine production.

A therapeutically effective amount of an antibody or antibody combination described herein relates generally to the amount needed to achieve a therapeutic objective. As noted above, this may be a binding interaction between the antibody and its target antigen(s) that, in certain cases, interferes with the functioning of the target(s). The amount required to be administered will furthermore depend on the binding affinity of the antibody for its specific antigen(s), and will also depend on the rate at which an administered antibody is depleted from the free volume of the subject to which it is administered. Common ranges for therapeutically effective dosing of an antibody, antibody combination or antibody fragment described herein may be, by way of nonlimiting example, from about 0.1 mg/kg body weight to about 50 mg/kg body weight. Common dosing frequencies may range, for example, from twice daily to once a week.

Antibodies specifically binding the TLR4/MD-2 complex, TLR4, MD2, TLR2 or CD14 or a fragment thereof can be administered for the treatment of disorders associated with aberrant LPS signaling in the form of pharmaceutical compositions. Principles and considerations involved in preparing such compositions, as well as guidance in the choice of components are provided, for example, in Remington: The Science And Practice Of Pharmacy 19th ed. (Alfonso R. Gennaro, et al., editors) Mack Pub. Co., Easton, Pa.: 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. (See, e.g., Marasco et al., Proc. Natl. Acad. Sci. USA, 90: 7889-7893 (1993)). The formulation can also contain more than one active compound as necessary for the particular indication being treated, preferably those with complementary activities that do not adversely affect each other. Alternatively, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions.

The formulations to be used for in vivo administration must be sterile. This is readily accomplished by filtration through sterile filtration membranes.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

Pharmaceutical Compositions

The antibodies or soluble chimeric polypeptides of the invention (also referred to herein as "active compounds"), and derivatives, fragments, analogs and homologs thereof, can be incorporated into pharmaceutical compositions suitable for administration. Such compositions typically comprise the antibody or soluble chimeric polypeptide and a pharmaceutically acceptable carrier. As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

The invention will be further described in the following examples, which do not limit the scope of the invention described in the claims.

EXAMPLES

Example 1

Materials and Methods

Reagents:

Both the α-human CD14 MAb 28C5 and the α-human TLR2MAb T2.5 have been previously described (See Weingarten et al., J Leukoc Biol. 53(5):518-24 (1993); Pugin et al., Blood, 104(13):4071-79 (2004); Meng et al., J. Clin. Invest., 113(10):1473-81 (2004); U.S. Pat. No. 6,444,206 and International Publication WO 2005/028509). T2.5 was purchased from eBioscience. The α-human TLR4MAb 15C1 (mouse IgG1 kappa) and the α-human MD-2 MAb 18H10 (mouse IgG2b) were generated in house using protocols previously described (See e.g., Pugin et al., Blood, vol. 104(13):4071-79 (2004)). All IgG isotype controls were purchased from BD biosciences (San Jose Calif.). In the experiments shown in FIGS. 1 and 2, ultrapure LPS Re595 (a TLR4 ligand) was purchased from List Biochemicals and $PAM_3CSK_4$ (a synthetic triacylated lipid that interacts with TLR2) was purchased from Invivogen. Bacterial strains *E. coli* wild 1 and K12 W3110 were obtained from Dr. J. Pugin, CMU, Geneva. In the remaining experiments, ultrapure LPS K12 and *Pseudomonas aeruginosa* 10 LPS were purchased from Sigma Aldrich. Purified flagellin and $PAM_3CSK_4$ were purchased from Invivogen. Bacterial strains *E. coli* wild type 1, *Pseudomonas aeruginosa*, *Klebsiella pnsumonia* and *Staphlococcus aureus* (SAUR2) were obtained from the HCG, Geneva; and K12 W3110 was obtained from Pierre Genevaux, CMU, Geneva. BEAS 2B and HEK 293 cells were obtained from the ATCC. *E. coli* was inactivated by heating for 30 minutes at 90° C. or by treatment with gentamycin at a concentration of 20 ug/ml. Inactivation was verified by plating on LB agar to check for the absence of colonies.

HEK 293, HUVEC, BEAS 2B Cell Assays:

For the results shown in FIGS. 1A-1B, stable transfected cells expressing either hTLR4/MD-2 or hTLR2 (referred to herein as the "HEK 293 hTLR4/MD2 transfectant" (FIG. 1A) and the "HEK 293 hTLR2 stable transfectant (FIG. 1B)) were generated using the methodology described previously (See e.g., Pugin et al., Blood 2004). Cells were plated at $6 \times 10^4$ cell/well in 200 μl DMEM 10% FCS medium the day before the experiment. The MAbs (15C1 (anti-TLR4) and T2.5 (anti-TLR2)) were diluted in 50 μl DMEM basal medium to a concentration of 150 μg/ml, added to the cells and incubated for 1 hour at 37° C. LPS Re595 (10 ng/ml final concentration) (FIG. 1A) or $PAM_3CSK_4$ (100 ng/ml final concentration) (FIG. 1B) were diluted in 100 μl RPMI 1640 containing 1%

FCS, added to the cells and left to incubate for 21 hours at 37° C. IL-8 secretion in the culture supernatant was monitored by ELISA (Endogen).

For the remaining cell-based experiments, cells were plated at $6 \times 10^4$ cell/well in 200 µl medium 10% FCS the day before the experiment. For HUVEC cells, plates were coated for 10 minutes with gelatin 2% (Sigma Aldrich) prior to plating. The medium was removed the day of the experiment and 30 µl of medium containing 6% heat inactivated human serum was added (final concentration 2%). Then, the appropriate MAbs were diluted in 30 µl basal medium to the appropriate concentration, and added to the cells for 1 hour at 37° C. Heat-inactivated bacteria (at the appropriate concentration) were diluted in 30 µl medium, added to the cells and left to incubate for 21 hours at 37° C. IL-6 (HUVEC and BEAS 2B) or IL-8 (HEK 293) secretion in the culture supernatant was monitored by ELISA (Endogen).

Flow Cytometry

To detect TLR2, TLR4, MD-2 and CD14 on the surface of HUVEC and BEAS 2B cells, $1 \times 10^7$ cells/ml were incubated in 1×PBS supplemented with 1% BSA and either 10 µg/ml of the appropriate antibody. Cells were washed once and then incubated in the same buffer with APC-conjugated goat anti-mouse IgG (H+L) antibody (1:250 dilution; Molecular Probes). Cells were analyzed using the FACScalibur™ in the FL-4 channel. For circulating leucocytes, the appropriate antibodies were added to human whole blood to a final concentration of 10 µg/ml. Following two wash steps in 1×PBS, 1% BSA, cells were incubated with secondary antibody (APC conjugated anti-mouse IgG (H+L) diluted 1:250) containing 100 µg/ml human IgG in order to prevent Fc mediated interactions (Sigma Aldrich). Red blood cells were removed by lysis using lysis buffer (Becton Dickinson) and remaining cells were washed twice. Cells were analyzed using the FACScalibur™ in the FL-4 channel. Different leukocyte populations were distinguished on the basis of forward and side scatter.

Figure 1:
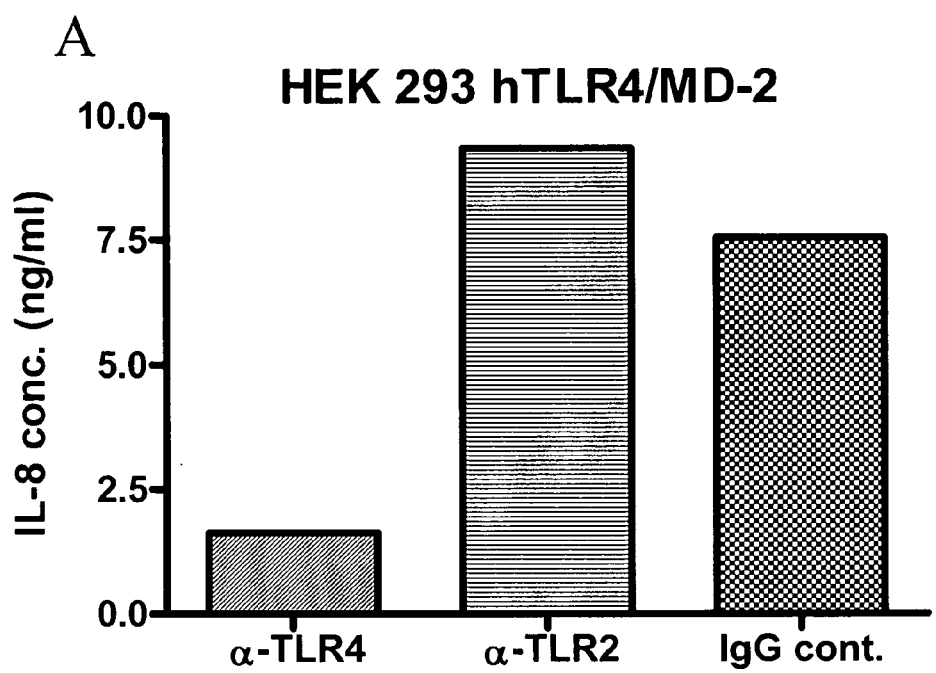
FIG. 1A is a graph depicting the effect of an anti-TLR4 monoclonal antibody (referred to as 15C1) and an anti-TLR2 monoclonal antibody (referred to herein as T2.5) on LPS-induced IL-8 production in either a HEK 293 hTLR4/MD2 transfectant (FIG. 1A).
FIG. 1B is a graph depicting the effect of the 15C1 anti-TLR4MAb and the T2.5 anti-TLR2MAb on $PAM_3CSK_4$-induced IL-8 production in a HEK 293 hTLR2 stable transfectant (FIG. 1B).
Figure 1:
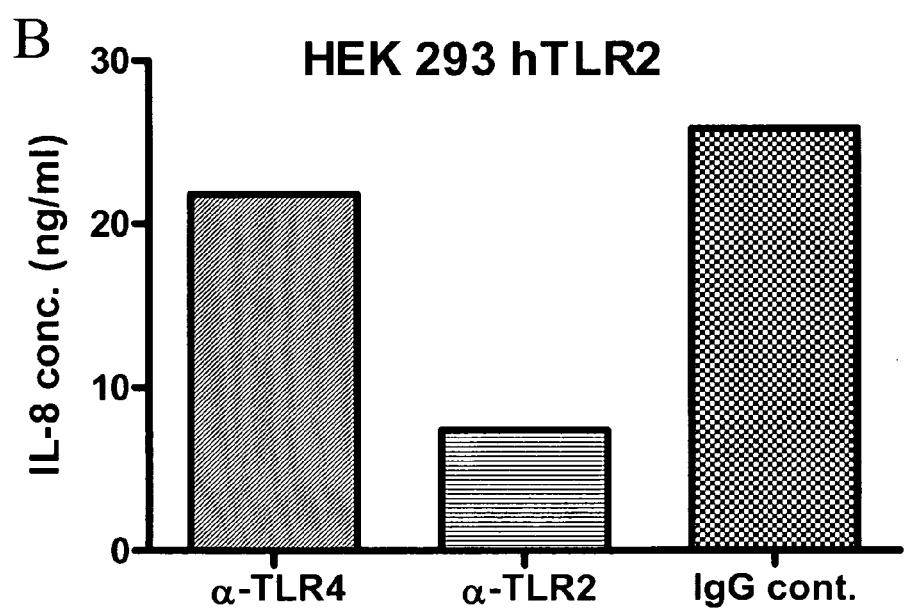

Whole Blood Assays:

In a first set of experiments shown in FIGS. 1 and 2, fresh blood from two healthy human volunteers (venipuncture in the arm vein) was mixed with heparin (10 µl/ml of blood), and diluted 1:2 with RPMI 1640 basal medium. Blood was plated at a volume of 100 µl/well and let to stand for 15 minutes at 37° C. The murine MAbs 15C1 (anti-TLR4), T2.5 (anti-TLR2) and 28C5 (anti-CD14) were prepared at the indicated concentrations diluted in RPMI 1640 basal medium (50 µl final volume) and added to the blood. In each case, the total amount of MAb prepared was normalized to the amount given in the triple MAb treatment using control IgG MAb. After incubation for 1 hour at 37° C., 50 µl of either heat-inactivated *E. coli* ($10^6$ CFU/ml final concentration), LPS Re595 (1 ng/ml final concentration) (FIG. 2A) or PAM$_3$CSK$_4$ (100 ng/ml final concentration) (FIG. 2B) was added to the blood and incubated for 6 hours. Plasma was then analyzed for IL-6 content by ELISA (Endogen).

Figure 3:
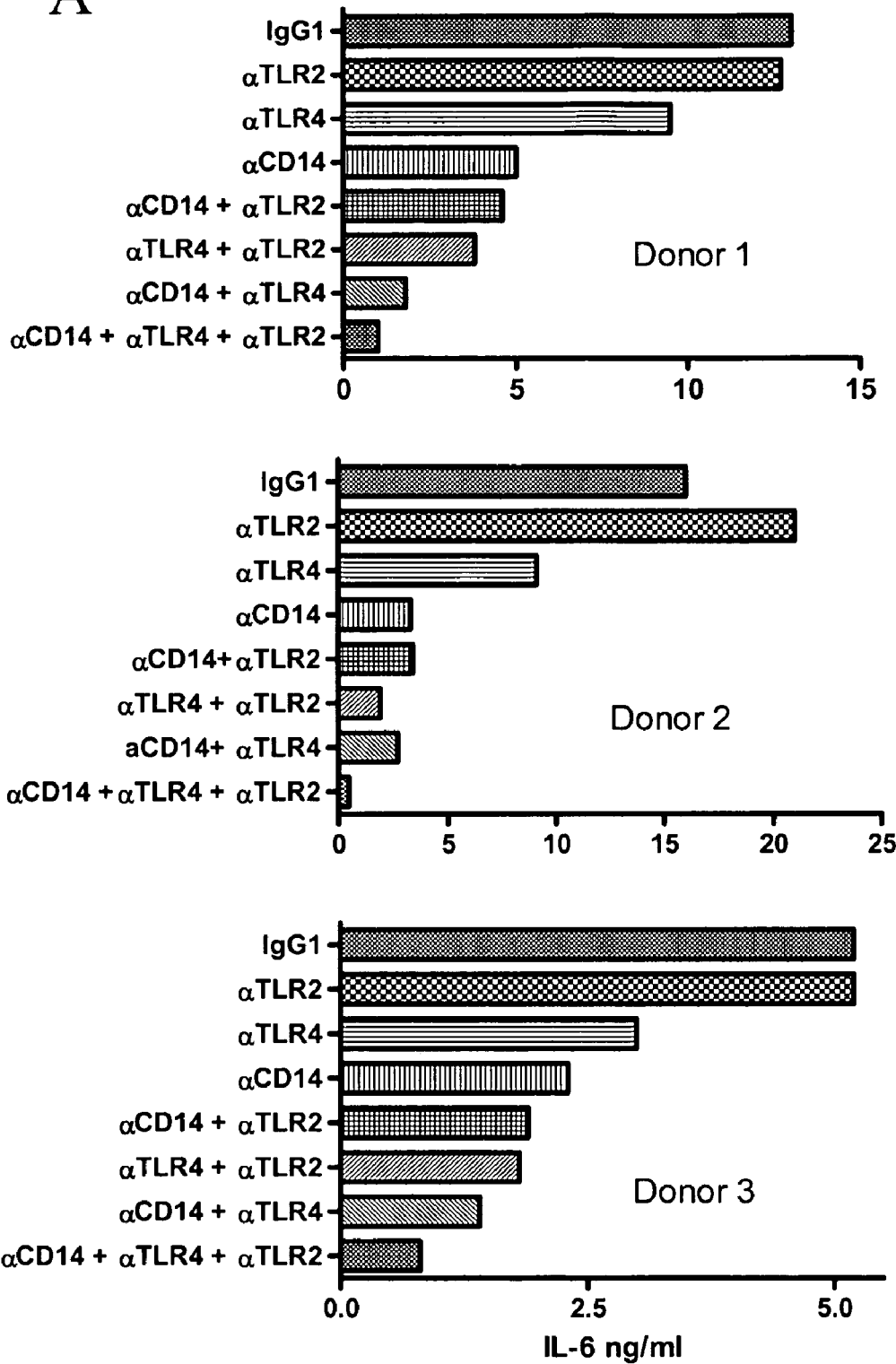
FIGS. 3A and 3B are a series of graphs depicting the effect of combinations of the 15C1 anti-TLR4MAb, the T2.5 anti- TLR2 MAb and the 28C5 anti-CD14 MAb on IL-6 production in whole blood stimulated by inactivated wild-type *E. coli*.
Figure 3:
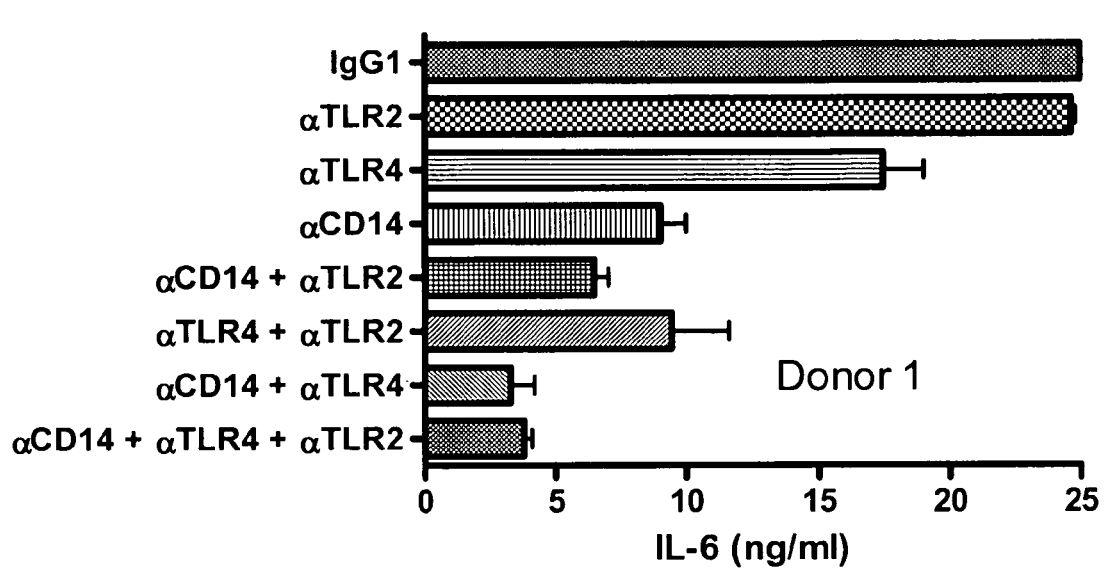

In a second set of experiments shown in FIGS. 3A and 3B, fresh blood from three healthy human volunteers was mixed with heparin (10 µl/ml of blood), diluted 1:2 with RPMI 1640 basal medium, and plated at a volume of 100 µl/well. The murine MAbs 15C1 (anti-TLR4), T2.5 (anti-TLR2) and 28C5 (anti-CD14), and combinations thereof, were prepared at the indicated concentrations diluted in RPMI 1640 basal medium (50 µl final volume), added to the blood and incubated for 1 hour on the cell. A volume of 50 ml of heat-inactivated *E. coli* at $10^6$ CFU/ml was added to the blood. The heat-inactivated *E. coli* was either a wild-type strain (FIG. 3A) or the common laboratory strain of *E Coli* known as K12 W3110 (FIG. 3B). Following an incubation of 6 hours, plasma IL-6 levels were measured by ELISA.

Figure 7:
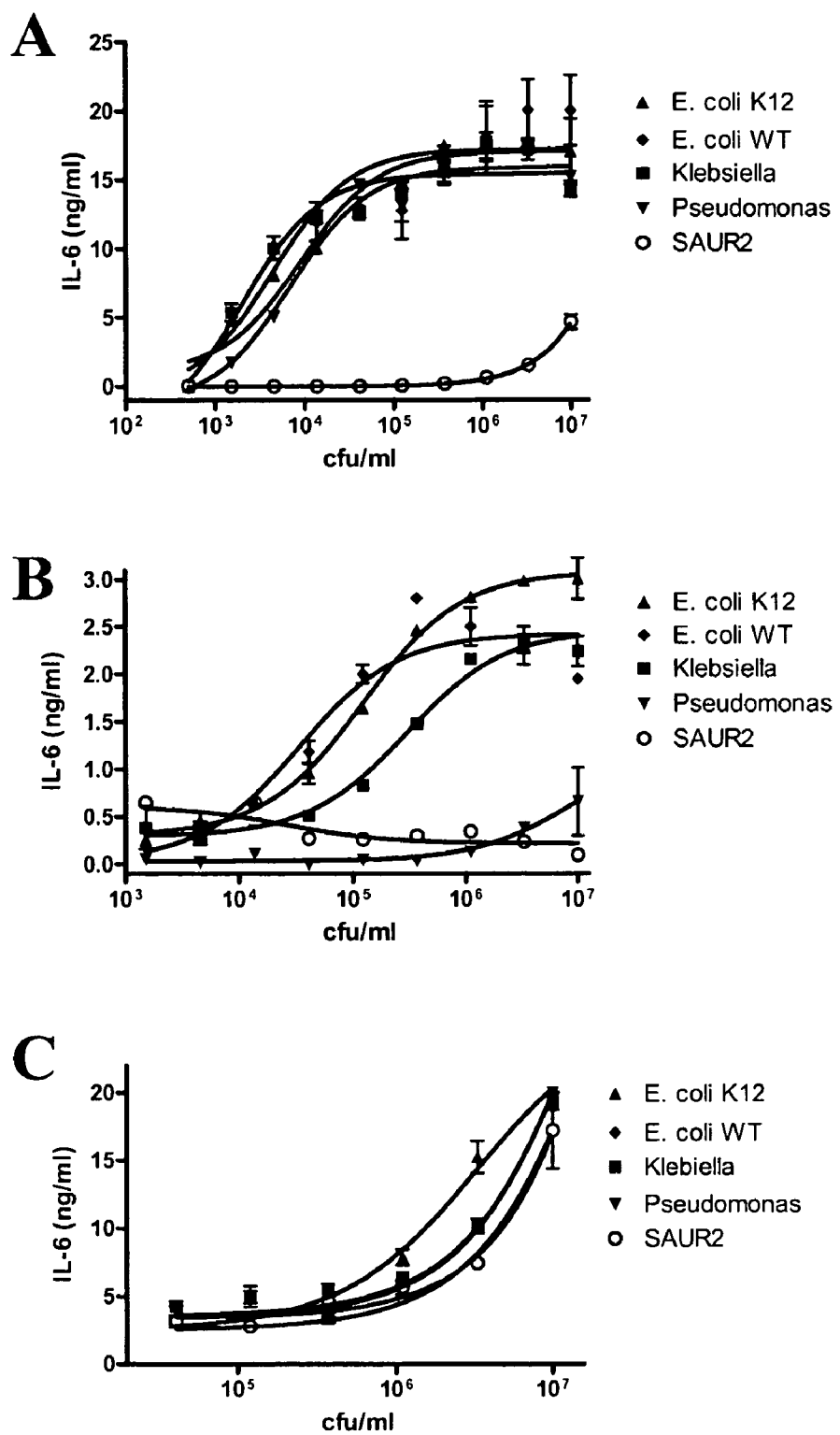
FIGS. 7A-7C are a series of graphs depicting induction of IL-6 production by heat-inactivated bacteria.
Figure 8:
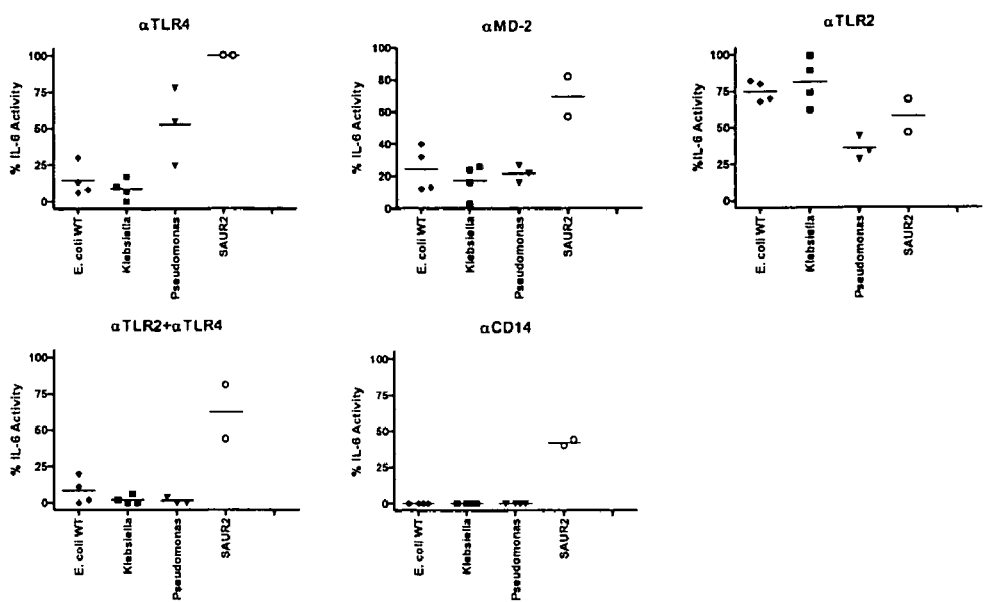
FIGS. 8A-8D are a series of graphs depicting inhibition of bacterial-induced IL-6 production by specific anti-TLR MAbs.
Figure 8:
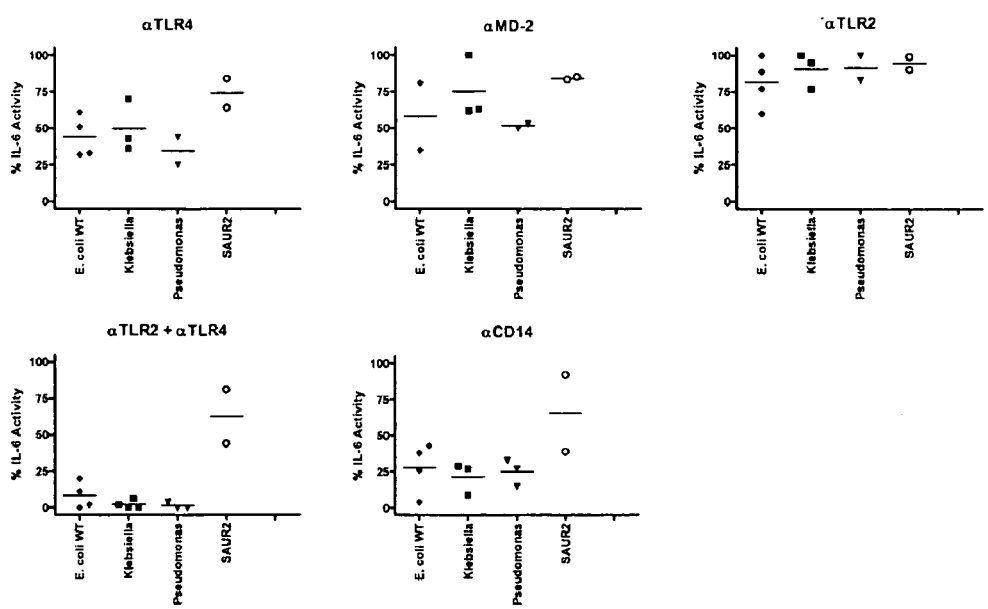

In a third set of experiments shown in FIGS. 5, 7 and 8, fresh blood from healthy human volunteers (venipuncture in the arm vein) was mixed with heparin (10 µl/ml of blood), and diluted 1:2 with RPMI 1640 basal medium. Blood was plated at a volume of 60 µl/well and let to stand for 15 minutes at 37° C. Where appropriate, MAbs were prepared at the indicated concentrations diluted in RPMI 1640 basal medium (30 µl final volume) and added to the blood. After 1 hour, 30 µl of either heat-inactivated bacteria (at the appropriate concentration), LPS K12 (4 ng/ml final concentration), PAM$_3$CSK$_4$ (100 ng/ml final concentration) or flagellin (300 ng/ml final concentration) was added to the blood and incubated for 6 hours. Plasma was subsequently analyzed for IL-6 content by ELISA (Endogen).

Example 2

TLR2, TLR4, MD-2 and CD14 Expression on Blood Leukocytes, HUVEC and BEAS 2B Cells In order to predict the responsiveness of the cell populations in this study to different TLR ligands, cell surface expression of TLR2, TLR4 and the TLR accessory molecules MD-2 and CD14 was examined by FACS analysis using specific MAbs.

Figure 4:
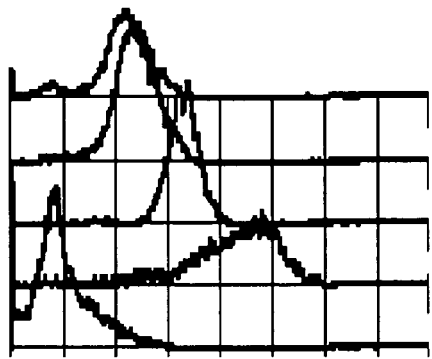
FIGS. 4A-4B are a series of graphs depicting surface expression of TLR2, TLR4, MD-2 and CD14 on blood leukocytes, HUVEC and BEAS 2B cells.
Figure 4:
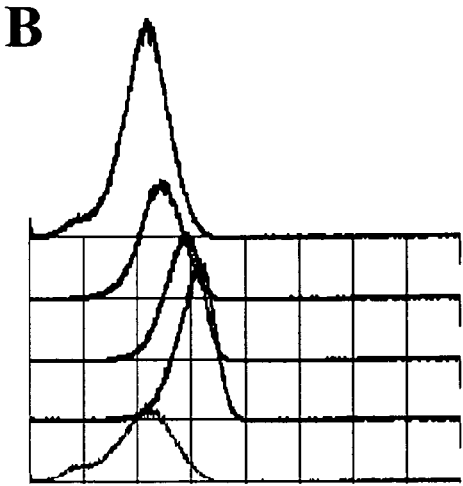
Figure 4:
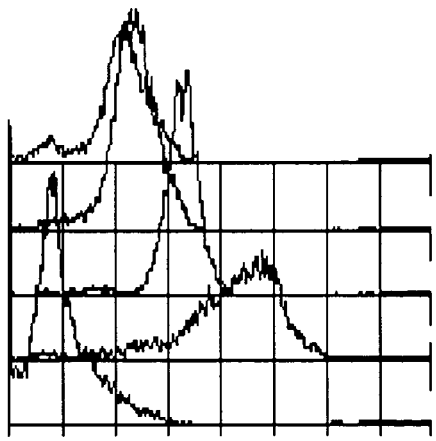
Figure 4:
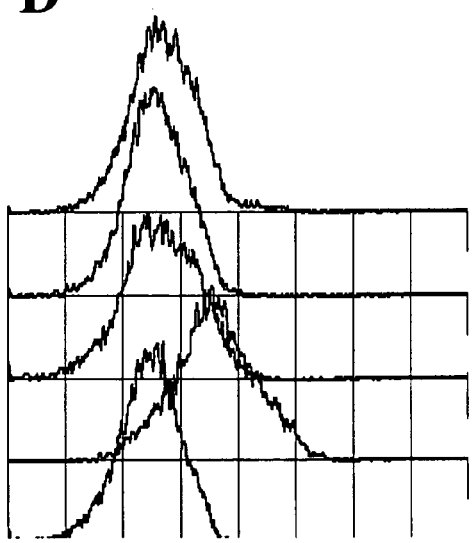

In human whole blood cell populations distinguished by size and granularity, significant surface levels of TLR4, MD-2 and TLR2 was observed, with high surface levels of CD14. Granulocytes were positive for CD14 and expressed weak but detectable levels of TLR2, TLR4 and MD-2 (FIG. 4, A-B). Lymphocytes did not express detectable levels of any of the proteins tested.

HUVEC were positive for TLR4 and MD-2 expression but negative for TLR2 and CD14 whereas BEAS 2B cells expressed weak but detectable levels of TLR2, TLR4 and MD-2, with a significant level of CD14 (FIG. 4, C-D).

Example 3

Inhibition of TLR Agonist-Induced Pro-Inflammatory Cytokine Production in Human Whole Blood with Blocking TLR2, TLR4, MD-2 and CD14 MAbs In FIGS. 1A-1B, the specificity of each MAb was investigated using the TLR4 and TLR2 specific ligands LPS and PAM$_3$CSK$_4$ respectively. FIG. 1A shows that the α-TLR4 blocking MAb, 15C1, efficiently inhibited LPS-dependent IL-8 production in human TLR4/MD-2 transfected HEK 293 cells. The anti-TLR2 specific MAb, T2.5, like the control MAb, had no effect on IL-8 production. Conversely, T2.5 blocked IL-8 production induced by PAM$_3$CSK$_4$ whereas 15C1 and the control MAb had no effect (FIG. 1B).

In human whole blood, both 15C1 and the anti-CD14 blocking MAb 28C5 blocked LPS-induced IL-6 production in a dose-dependent manner whilst T2.5 and the control MAb had no effect (FIG. 2a). Both T2.5 and 28C5 blocked PAM$_3$CSK$_4$-induced IL-6 production in a dose-dependent fashion, whilst 15C1 and the control MAb had no effect (FIG. 2b).

In FIG. 5, the specificity and potency of the neutralizing TLR2, TLR4, MD-2 and CD14 MAbs on human whole blood stimulated with *E. coli* K12 LPS (TLR4 agonist), and PAM$_3$CSK$_4$ (TLR2 agonist) were examined.

E. coli K12 LPS potently induced IL-6 production. This production was strongly inhibited by anti-TLR4 and CD14 MAbs. The anti-MD-2 MAb inhibited IL-6 levels to a lesser but significant effect, whereas the anti-TLR2MAb showed no significant neutralizing capacity. These results are in accordance with a role for TLR4, MD-2 and CD14 in the recognition of E. coli LPS.

IL-6 production induced by pseudomonas LPS could by partially (~50%) inhibited by anti-TLR2, TLR4, MD-2, and CD14 MAbs. A combination of TLR2 and TLR4 MAbs completely inhibited IL-6 production, suggesting that this particular strain of LPS can be recognized by TLR2 and TLR4.

$Pam_3CSK_4$ is a synthetic tripalmitoylated lipopeptide that mimics the acylated amino terminus of bacterial lipoproteins and signals through TLR2. In human whole blood, a low but significant level of IL-6 could be detected following treatment with this purified agonist. The induction of IL-6 was greatly diminished with TLR2MAbs. In addition, anti-CD14 treatment also strongly inhibited this effect, suggesting a role for this adaptor protein in the recognition of the molecule by TLR2. Anti-TLR4 and MD-2 MAbs had no significant effect on IL-6 levels.

Flagellin is the major component of the bacterial flagellar filament, which confers motility on a wide range of bacterial species. It has been shown to signal via TLR5, possibly as a heterodimer with TLR4 (Mizel et al., J. Immunol., vol. 170: 6217-6223 (2003)). In human whole blood, flagellin strongly induced the production of IL-6. Anti-TLR2MAb treatment had no effect on this induction. In contrast, anti-TLR4, MD-2 and CD14 MAbs could significantly inhibit this response, suggesting a role for these proteins in the innate immune response to flagellin, as previously reported ((Mizel et al., J. Immunol., vol. 170:6217-6223 (2003))).

Together, these results confirm the specificity and demonstrate the potency of the anti-TLR2, TLR4, MD-2 and anti-CD14 blocking MAbs used in this study.

Example 4

Inhibition of Heat-Inactivated E. coli in Human Whole Blood with α-TLR2, α-TLR4 and α-CD14 MAbs To test the hypothesis that microbes are capable of stimulating more that one TLR receptor in parallel, the effect of α-TLR4, TLR2 and CD14 blocking MAbs in inhibiting the innate immune reaction against heat-inactivated E. coli in human whole blood was investigated. Two strains of E. coli (WT and K12) with different combinations of MAb and either single, double or triple antibody treatment were used to determine the dominant TLR in activating immune responses and the effect of blocking more than one TLR receptor in inhibiting these immune responses.

FIG. 3a shows the ability of different MAb combinations to inhibit IL-6 production in whole blood stimulated by heat inactivated WT E. coli. Blood from 3 different healthy donors responded strongly to the E. coli preparation ($10^6$ cfu/ml). This response was slightly diminished by the addition of the αTLR4 blocking MAb, but not by the αTLR2 blocking MAb. A combination of both MAbs strongly inhibited the response of whole blood to E. coli. The αCD14 MAb treatment alone was also very potent. A combination of either αCD14 and αTLR4 or αCD14 and αTLR2 showed more efficient blocking than αCD14 alone. This indicates that some E. coli derived TLR4 and TLR2 ligands are working through a CD14 independent mechanism. Blockade of CD14, TLR4 and TLR2 was the most potent treatment in inhibiting IL-6 production. Similar results were found using a common laboratory strain of E coli (K12 W3110; see FIG. 3b).

Example 5

Induction of Pro-Inflammatory Cytokine Production in Transfected HEK 293 Cells, Human Whole Blood, HUVEC and BEAS 2B Cells by Different Bacterial Strains In order to demonstrate the ability of different bacterial strains to stimulate pro-inflammatory cytokine production, the above cell types were treated with increasing doses of heat-inactivated E. coli WT and K12 strains, Pseudomonas aeruginosa, Klebsiella pneumonia and staphylococcus aureas.

The ability of each bacterial strain to stimulate HEK 293 cells transfected either with TLR2 or the TLR4/MD-2 complex was tested. On TLR2-transfected HEK 293 cells, all gram-negative strains tested induced a detectable response from $5\times10^5$ cfu/ml upwards with a maximum IL-8 response at the highest dose tested ($10^7$ cfu/ml). Pseudomonas produced the highest response of all strains tested. These results confirm, as previously reported, the presence of PAMPs such as lipoproteins capable of stimulating TLR2 within the gram-negative bacterial strains tested in this study. Interestingly, the gram-positive S. aureas failed to induce any IL-8 response, suggesting that TLR2 alone is insufficient to recognize PAMPs from this bacterial strain (such as LTA), and that other TLRs in combination with TLR2 but absent on the TLR2 transfected HEK 293 cells (i.e. TLR1 and TLR6) are probably required to induce a response. HEK 293 cells transfected with TLR4 and MD-2 also responded robustly to both E. coli strains and to Klebsiella. $5\times10^4$ cfu/ml was the lowest dose capable of inducing a response. The cells responded poorly to pseudomonas, with a weak but significant response seen at $5\times10^6$ and $1\times10^7$ cfu/ml. The cells were unresponsive to S. aureas at all concentrations tested. Non-transfected HEK 293 cells were unresponsive to all bacteria (data not shown).

Figure 6:
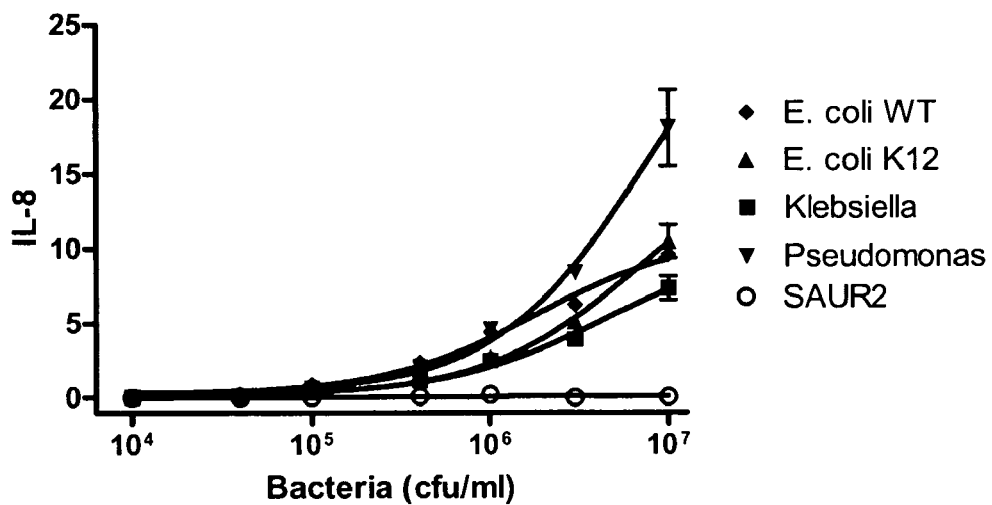
FIGS. 6A and 6B are a series of graphs depicting the induction of IL-8 production in transfected HEK 293 cells by heat-inactivated bacteria.
Figure 6:
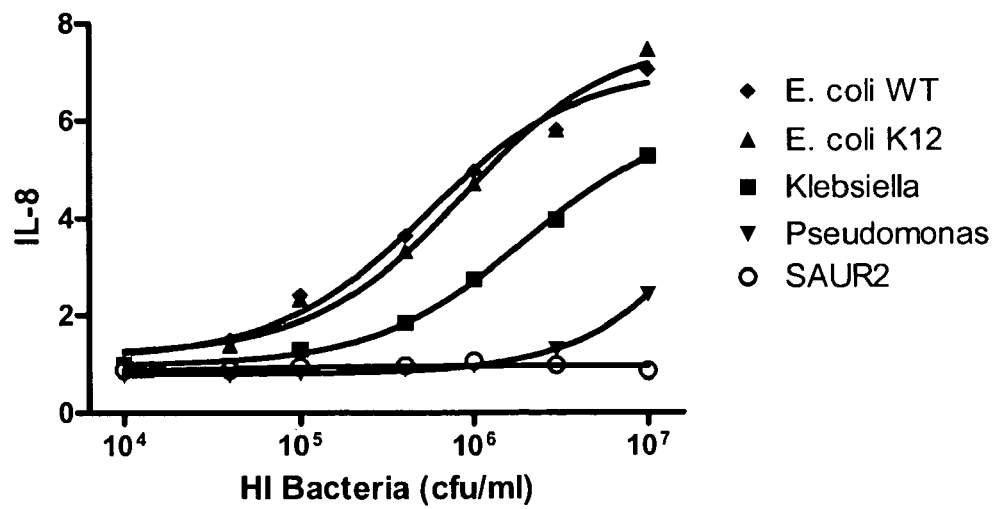

In human whole blood, a robust response to all gram-negative bacterial strains was observed (FIG. 7A). Induction of IL-6 production could be observed with as little as $2\times10^3$ cfu/ml, with a response-plateau at around $5\times10^5$ cfu/ml. In general, the gram-positive bacterial strain S. aureas was inefficient at inducing a response in whole blood. With the particular donor represented in FIG. 7A, a small but significant response was seen only at doses of bacteria above $10^6$ cfu/ml (FIG. 7A). In other donors tested, low-level IL-6 responses could be detected with as little as $10^4$ cfu/ml of bacteria. This response typically increased slightly up to the highest dose tested ($10^7$ cfu/ml). In HUVEC (FIG. 7B), IL-6 production was induced by doses above $10^4$ cfu/ml for E. coli and Klebsiella bacterial strains. The response plateau was seen at above $10^6$ cfu/ml. Pseudomonas was a poor inducer of IL-6 production, with a very weak response seen only at the highest dose tested ($10^7$ cfu/ml). Staphlococcus was ineffective on HUVEC at all doses tested. BEAS 2B cells responded to all bacterial strains tested above $10^6$ cfu/ml. The maximal response for each strain was observed at $10^7$ cfu/ml, the highest dose tested (FIG. 6C).

Based on these results $10^4$ and $10^6$ cfu/ml of bacteria was chosen to stimulate human whole blood, with $10^7$ chosen as the bacterial dose for HUVEC and BEAS 2B.

Example 6

Inhibition of IL-6 Responses to Whole Bacteria with Anti-TLR2, TLR4, MD-2 and CD14 MAbs To understand the contribution made by different TLRs to the cellular response to whole bacteria, the different cell types included in this study were exposed to heat-inactivated bacteria following a pre-incubation with the blocking MAbs outlined above.

At $10^4$ cfu/ml in human whole blood (FIG. 8A), TLR4 blockade strongly reduced the IL-6 production induced by *E. coli* and *Klebsiella* strains and partially reduced the levels seen with pseudomonas. Anti-TLR4MAbs had no effect on *Staphlococcus* induction of IL-6. MD-2 blockade largely mirrored TLR4 blockade, with the exception that pseudomonas-induced IL-6 production was more potently inhibited. TLR2 blockade had no significant effect on *E. coli* and *Klebsiella*-induced IL-6 production, and partially inhibited both pseudomonas and *staphylococcus*. A combination of TLR2 and TLR4 blockade strongly inhibited responses to all gram-negative strains tested whilst only partially inhibiting *Staphlococcus*. Anti-CD14 treatment largely resembled TLR2/TLR4 cotreatment. Together, these results suggest that at this chosen dose of bacteria, PAMPs signaling via TLR4/MD-2 are largely dominant in inducing an immune response to *E. coli* and *Klebsiella*. *Pseudomonas* appears to signal exclusively via TLR4/MD-2 and TLR2-containing receptor complexes, whereas *Staphlococcus*-induced IL-6 production is partially-dependent on TLR2 and independent of TLR4/MD-2. This result suggests that other TLRs or related proteins must be implicated in *Staphlococcus*-induced IL-6 production. The inhibition pattern seen with the anti-CD14 MAb implies a role for this protein in the recognition of ligands signaling via both TLR2 and TLR4.

At $10^6$ cfu/ml in human whole blood (FIG. 8B), TLR4 and MD-2 blockade resulted in partial inhibition of IL-6 induction by *E. coli, Klebsiella* and *Pseudomonas*. TLR2 blockade was ineffective with all bacterial strains tested. Interestingly, TLR2 and TLR4 combination treatment resulted in a complete inhibition of *E. coli* and *Klebsiella*-induced IL-6 production. This suggests that at higher doses of bacteria, TLR2 ligands can stimulate IL-6 production in the absence of TLR4 signaling. Induction of IL-6 by $10^6$ cfu/ml pseudomonas was partially inhibited either by TLR4/MD-2 or TLR2 blockade, with a strong inhibition seen following co-treatment of TLR2 and TLR4, reflecting what was observed at $10^4$ cfu/ml. The pattern of CD14 blockade at $10^6$ cfu/ml bacteria also mirrored that seen with $10^4$ cfu/ml, also inhibition was generally slightly less potent.

The effects of blocking TLR2 and TLR4 signaling on IL-6 production in HUVEC treated with either *E. coli* or *Klebsiella* at $10^7$ cfu/ml was tested. As expected from the expression profile of TLRs on the surface of HUVECs (TLR2-, TLR4/MD-2+), the activity of both *E. coli* and *Klebsiella* was inhibited by anti-TLR4, MD-2 and CD14 blocking MAbs, whereas anti-TLR2 MAbs had no effect (FIG. 8C).

TLR blockade on bacterial stimulation of BEAS-2B at $10^7$ cfu/ml was tested. Although surface staining revealed low level expression of TLRs 2 and 4 (FIG. 4D), cells responded in a relatively robust fashion to stimulation with high concentrations of both gram-negative and positive bacterial strains (FIG. 7C). Blockade of either TLR4 or MD-2 resulted in a minimal inhibitory effect on IL-6 production. In contrast, TLR2 blockade strongly diminished IL-6 production, suggesting that TLR2 rather than TLR4 is functionally responsible for bacterial stimulation of this epithelial cell line. This was the case for all bacteria tested, including the gram-positive strain *S. aureas*. The contribution of CD14 in the recognition of all four bacterial strains tested was also demonstrated using the anti-CD14 blocking MAb (FIG. 8D).

Example 7

Figure 9:
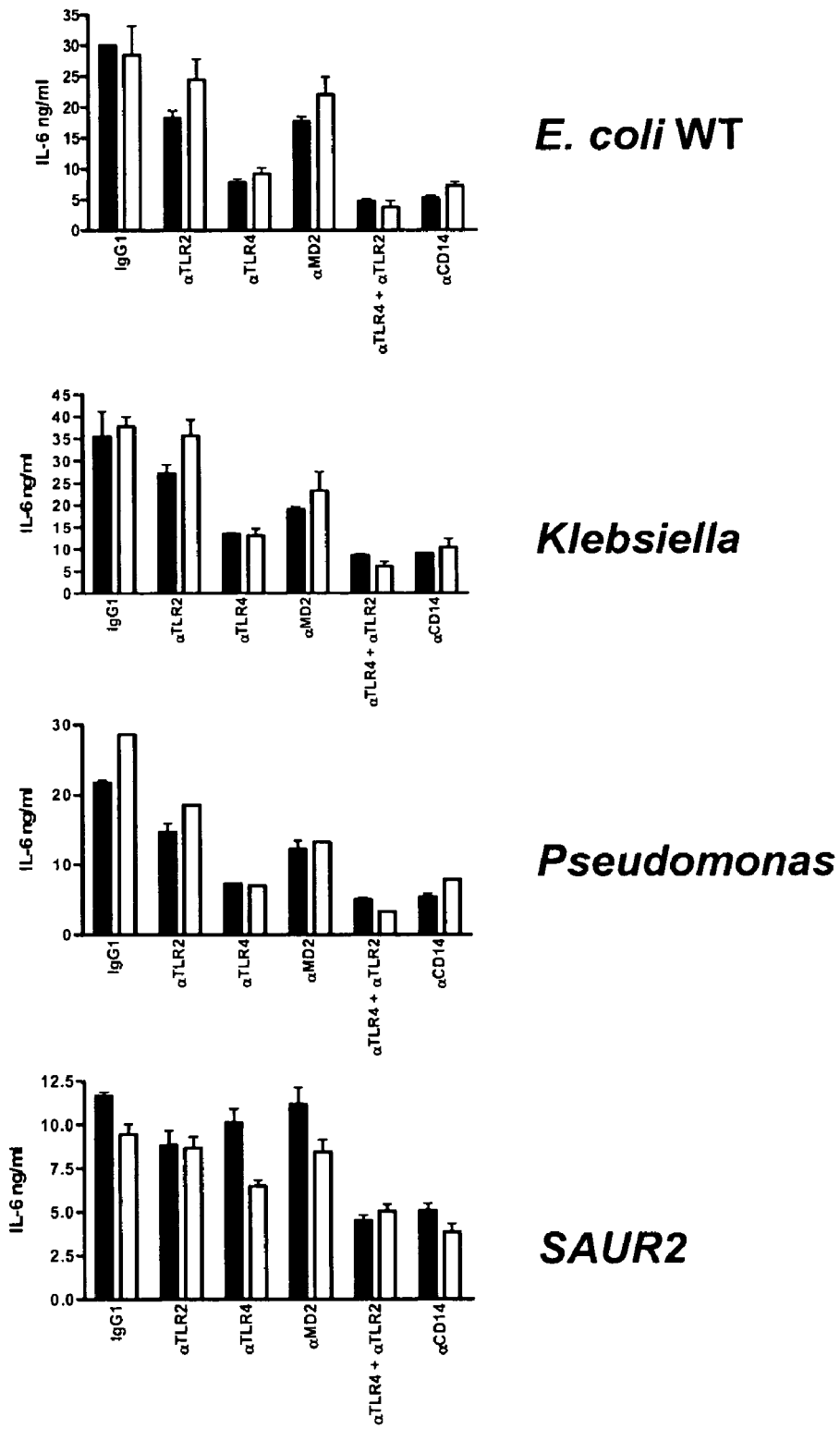
FIG. 9 is a series of graphs depicting comparison of IL-6 production induced in human whole blood by heat-inactivated and antibiotic-inactivated bacteria.

Evaluation of Heat-Inactivation Versus Antibiotic Inactivation on Bacterial Stimulation of Whole Blood The effect of heat-inactivation on the integrity of PAMPs and the subsequent ability of the bacterial strains tested to stimulate innate immune responses were evaluated. The IL-6 production induced by heat-inactivated bacteria was compared with that of bacteria inactivated by antibiotic treatment (gentamycin). Gentamycin was chosen as this antibiotic acts at the level of the bacterial DNA and therefore structural PAMPs remain intact with this method of inactivation. As shown in FIG. 9, bacteria inactivated by both methods retained an equivalent capacity, at a dose of $10^6$ cfu/ml ($10^7$ cfu/ml for *Staphlococcus aureus*), to stimulate circulating monocytes to produce IL-6. Levels of inhibition of cytokine production using anti-TLR2, TLR4, MD-2 and CD14 were also comparable, suggesting that the relevant TLR ligands retained their potency no matter what the method of inactivation used. These results suggest that heat-inactivation of bacteria is a valid method to study the stimulation of the innate immune system by TLR-agonists derived from bacteria.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

SEQUENCE LISTING

```
<160> NUMBER OF SEQ ID NOS: 61

<210> SEQ ID NO 1
<211> LENGTH: 360
<212> TYPE: DNA
<213> ORGANISM: Artificial Sequence
<220> FEATURE:
<223> OTHER INFORMATION: Variable heavy chain sequence of murine 18H10
      antibody

<400> SEQUENCE: 1
caggtgcaac tgcagcagtc tggggctgat cttgtgaggc caggggcctt agtcaagttg      60
```

```
tcctgcacag cttctggctt caacattaaa gactcctata tacactgggt gaagaagagg      120
cctgaatggg gcctggagtg gattggatgg actgatcctg agaatgttaa ttctatatat      180
gacccgaggt ttcagggcaa ggccagtata acagcagaca catcctccaa cacagccttc      240
cttcagctca ccagcctgac atctgaggac actgccgtct attactgtgc tagggggttat     300 aacggtgttt actatgctat ggactactgg ggccaaggga cctcagtcac cgtctcctca      360
```

<210> SEQ ID NO 2
<211> LENGTH: 120
<212> TYPE: PRT
<213> ORGANISM: Artificial Sequence
<220> FEATURE:
<223> OTHER INFORMATION: Variable heavy chain sequence of murine 18H10
      antibody

<400> SEQUENCE: 2

```
Gln Val Gln Leu Gln Gln Ser Gly Ala Asp Leu Val Arg Pro Gly Ala
1               5                   10                  15

Leu Val Lys Leu Ser Cys Thr Ala Ser Gly Phe Asn Ile Lys Asp Ser
            20                  25                  30

Tyr Ile His Trp Val Lys Lys Arg Pro Glu Trp Gly Leu Glu Trp Ile
        35                  40                  45

Gly Trp Thr Asp Pro Glu Asn Val Asn Ser Ile Tyr Asp Pro Arg Phe
    50                  55                  60

Gln Gly Lys Ala Ser Ile Thr Ala Asp Thr Ser Ser Asn Thr Ala Phe
65                  70                  75                  80

Leu Gln Leu Thr Ser Leu Thr Ser Glu Asp Thr Ala Val Tyr Tyr Cys
                85                  90                  95

Ala Arg Gly Tyr Asn Gly Val Tyr Tyr Ala Met Asp Tyr Trp Gly Gln
            100                 105                 110

Gly Thr Ser Val Thr Val Ser Ser
        115                 120
```

<210> SEQ ID NO 3
<211> LENGTH: 5
<212> TYPE: PRT
<213> ORGANISM: Artificial Sequence
<220> FEATURE:
<223> OTHER INFORMATION: Variable heavy chain CDR1 sequence of murine
      18H10 antibody

<400> SEQUENCE: 3

```
Asp Ser Tyr Ile His
1               5
```

<210> SEQ ID NO 4
<211> LENGTH: 17
<212> TYPE: PRT
<213> ORGANISM: Artificial Sequence
<220> FEATURE:
<223> OTHER INFORMATION: Variable heavy chain CDR2 sequence of murine
      18H10 antibody

<400> SEQUENCE: 4

```
Trp Thr Asp Pro Glu Asn Val Asn Ser Ile Tyr Asp Pro Arg Phe Gln
1               5                   10                  15

Gly
```

<210> SEQ ID NO 5
<211> LENGTH: 11
<212> TYPE: PRT
<213> ORGANISM: Artificial Sequence

```
<220> FEATURE:
<223> OTHER INFORMATION: Variable heavy chain CDR3 sequence of murine
      18H10 antibody

<400> SEQUENCE: 5

Gly Tyr Asn Gly Val Tyr Tyr Ala Met Asp Tyr
1               5                   10

<210> SEQ ID NO 6
<211> LENGTH: 321
<212> TYPE: DNA
<213> ORGANISM: Artificial Sequence
<220> FEATURE:
<223> OTHER INFORMATION: Variable light chain sequence of murine 18H10
      antibody

<400> SEQUENCE: 6
caaattgttc tcacccagtc tccatcaatc atgtctgcgt ctctagggga ggagatcacc      60
ctaacctgca gtgccagctc gagtgtaatt tacatgcact ggtaccagca gaagtcaggc     120
acttctccca aactcttgat ttataggaca tacaacctgg cttctggagt cccttctcgc     180
ttcagtggca gtgggtctgg gacctttat tctctcacaa tcagcagtgt ggaggctgaa     240
gatgctgccg attattactg ccatcagtgg agtagttttc cgtacacgtt cggagggggg     300
accaagctgg aaatcaaacg g                                              321

<210> SEQ ID NO 7
<211> LENGTH: 107
<212> TYPE: PRT
<213> ORGANISM: Artificial Sequence
<220> FEATURE:
<223> OTHER INFORMATION: Variable light chain sequence of murine 18H10
      antibody

<400> SEQUENCE: 7

Gln Ile Val Leu Thr Gln Ser Pro Ser Ile Met Ser Ala Ser Leu Gly
1               5                   10                  15

Glu Glu Ile Thr Leu Thr Cys Ser Ala Ser Ser Ser Val Ile Tyr Met
                20                  25                  30

His Trp Tyr Gln Gln Lys Ser Gly Thr Ser Pro Lys Leu Leu Ile Tyr
            35                  40                  45

Arg Thr Tyr Asn Leu Ala Ser Gly Val Pro Ser Arg Phe Ser Gly Ser
        50                  55                  60

Gly Ser Gly Thr Phe Tyr Ser Leu Thr Ile Ser Ser Val Glu Ala Glu
65                  70                  75                  80

Asp Ala Ala Asp Tyr Tyr Cys His Gln Trp Ser Ser Phe Pro Tyr Thr
                85                  90                  95

Phe Gly Gly Gly Thr Lys Leu Glu Ile Lys Arg
            100                 105

<210> SEQ ID NO 8
<211> LENGTH: 10
<212> TYPE: PRT
<213> ORGANISM: Artificial Sequence
<220> FEATURE:
<223> OTHER INFORMATION: Variable light chain CDR1 sequence of murine
      18H10 antibody

<400> SEQUENCE: 8

Ser Ala Ser Ser Ser Val Ile Tyr Met His
1               5                   10

<210> SEQ ID NO 9
```

```
<211> LENGTH: 7
<212> TYPE: PRT
<213> ORGANISM: Artificial Sequence
<220> FEATURE:
<223> OTHER INFORMATION: Variable light chain CDR2 sequence of murine
      18H10 antibody

<400> SEQUENCE: 9

Arg Thr Tyr Asn Leu Ala Ser
1               5

<210> SEQ ID NO 10
<211> LENGTH: 9
<212> TYPE: PRT
<213> ORGANISM: Artificial Sequence
<220> FEATURE:
<223> OTHER INFORMATION: Variable light chain CDR3 sequence of murine
      18H10 antibody

<400> SEQUENCE: 10

His Gln Trp Ser Ser Phe Pro Tyr Thr
1               5

<210> SEQ ID NO 11
<211> LENGTH: 353
<212> TYPE: DNA
<213> ORGANISM: Artificial Sequence
<220> FEATURE:
<223> OTHER INFORMATION: Variable heavy chain sequence of murine 16G7
      antibody

<400> SEQUENCE: 11
aggtgaaact gcaggagtct ggagctgagc tgatgaagcc tggggcctca gtgaagatat      60
cctgcaaggc tactggctac aaattcagtg actactggat agagtggata aacagaggc     120 ctggacatgg ccttgagtgg attggagaga ttttgcctgg aagtggtagt actaactaca    180
atgaggactt caaggacaag gccacattca cttcagatac atcctccaac acagcctaca    240
tgcaactcag cagcctgaca tctgaagact ctgccgtcta ttactgtgca aagaggaga    300 gggcgtacta ctttggctat tggggccaag ggaccacggt caccgtctcc tca           353

<210> SEQ ID NO 12
<211> LENGTH: 117
<212> TYPE: PRT
<213> ORGANISM: Artificial Sequence
<220> FEATURE:
<223> OTHER INFORMATION: Variable heavy chain sequence of murine 16G7
      antibody

<400> SEQUENCE: 12

Val Lys Leu Gln Glu Ser Gly Ala Glu Leu Met Lys Pro Gly Ala Ser
1               5                   10                  15

Val Lys Ile Ser Cys Lys Ala Thr Gly Tyr Lys Phe Ser Asp Tyr Trp
            20                  25                  30

Ile Glu Trp Ile Lys Gln Arg Pro Gly His Gly Leu Glu Trp Ile Gly
        35                  40                  45

Glu Ile Leu Pro Gly Ser Gly Ser Thr Asn Tyr Asn Glu Asp Phe Lys
    50                  55                  60

Asp Lys Ala Thr Phe Thr Ser Asp Thr Ser Ser Asn Thr Ala Tyr Met
65                  70                  75                  80

Gln Leu Ser Ser Leu Thr Ser Glu Asp Ser Ala Val Tyr Tyr Cys Ala
                85                  90                  95

Lys Glu Glu Arg Ala Tyr Tyr Phe Gly Tyr Trp Gly Gln Gly Thr Thr
            100                 105                 110
```

Val Thr Val Ser Ser
        115

<210> SEQ ID NO 13
<211> LENGTH: 5
<212> TYPE: PRT
<213> ORGANISM: Artificial Sequence
<220> FEATURE:
<223> OTHER INFORMATION: Variable heavy chain CDR1 sequence of murine
      16G7 antibody

<400> SEQUENCE: 13

Asp Tyr Trp Ile Glu
1               5

<210> SEQ ID NO 14
<211> LENGTH: 17
<212> TYPE: PRT
<213> ORGANISM: Artificial Sequence
<220> FEATURE:
<223> OTHER INFORMATION: Variable heavy chain CDR2 sequence of murine
      16G7 antibody

<400> SEQUENCE: 14

Glu Ile Leu Pro Gly Ser Gly Ser Thr Asn Tyr Asn Glu Asp Phe Lys
1               5                   10                  15

Asp

<210> SEQ ID NO 15
<211> LENGTH: 9
<212> TYPE: PRT
<213> ORGANISM: Artificial Sequence
<220> FEATURE:
<223> OTHER INFORMATION: Variable heavy chain CDR3 sequence of murine
      16G7 antibody

<400> SEQUENCE: 15

Glu Glu Arg Ala Tyr Tyr Phe Gly Tyr
1               5

<210> SEQ ID NO 16
<211> LENGTH: 339
<212> TYPE: DNA
<213> ORGANISM: Artificial Sequence
<220> FEATURE:
<223> OTHER INFORMATION: Variable light chain sequence of murine 16G7
      antibody

<400> SEQUENCE: 16
gatgttttga tgacccaaac tccactctcc ctgcctgtca gtcttggaga tcaagcctcc      60
atctcttgca ggtctagtca gagccttgaa aacagtaatg gaaacaccta tttgaactgg     120
tacctccaga aaccaggcca gtctccacag ctcctgatct acagggtttc caaccgattt     180
tctggggtcc tagacaggtt cagtggtagt ggatcaggga cagatttcac actgaaaatc     240
agcagagtgg aggctgagga tttgggagtt tatttctgcc tccaagttac acatgtccct     300
cccacgttcg gtgctgggac caagctggaa ctgaaacgg                            339

<210> SEQ ID NO 17
<211> LENGTH: 113
<212> TYPE: PRT
<213> ORGANISM: Artificial Sequence
<220> FEATURE:
<223> OTHER INFORMATION: Variable light chain sequence of murine 16G7
      antibody

```
<400> SEQUENCE: 17

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Leu Glu Asn Ser
            20                  25                  30

Asn Gly Asn Thr Tyr Leu Asn Trp Tyr Leu Gln Lys Pro Gly Gln Ser
        35                  40                  45

Pro Gln Leu Leu Ile Tyr Arg Val Ser Asn Arg Phe Ser Gly Val Leu
    50                  55                  60

Asp Arg Phe Ser Gly Ser Gly Ser Gly Thr Asp Phe Thr Leu Lys Ile
65              70                  75                  80

Ser Arg Val Glu Ala Glu Asp Leu Gly Val Tyr Phe Cys Leu Gln Val
                85                  90                  95

Thr His Val Pro Pro Thr Phe Gly Ala Gly Thr Lys Leu Glu Leu Lys
            100                 105                 110

Arg

<210> SEQ ID NO 18
<211> LENGTH: 16
<212> TYPE: PRT
<213> ORGANISM: Artificial Sequence
<220> FEATURE:
<223> OTHER INFORMATION: Variable light chain CDR1 sequence of murine
      16G7 antibody

<400> SEQUENCE: 18

Arg Ser Ser Gln Ser Leu Glu Asn Ser Asn Gly Asn Thr Tyr Leu Asn
1               5                   10                  15

<210> SEQ ID NO 19
<211> LENGTH: 7
<212> TYPE: PRT
<213> ORGANISM: Artificial Sequence
<220> FEATURE:
<223> OTHER INFORMATION: Variable light chain CDR2 sequence of murine
      16G7 antibody

<400> SEQUENCE: 19

Arg Val Ser Asn Arg Phe Ser
1               5

<210> SEQ ID NO 20
<211> LENGTH: 9
<212> TYPE: PRT
<213> ORGANISM: Artificial Sequence
<220> FEATURE:
<223> OTHER INFORMATION: Variable light chain CDR3 sequence of murine
      16G7 antibody

<400> SEQUENCE: 20

Leu Gln Val Thr His Val Pro Pro Thr
1               5

<210> SEQ ID NO 21
<211> LENGTH: 354
<212> TYPE: DNA
<213> ORGANISM: Artificial Sequence
<220> FEATURE:
<223> OTHER INFORMATION: Variable heavy chain sequence of murine 15C1
      antibody

<400> SEQUENCE: 21
gatgtgcagc ttcaggagtc aggacctgac ctaatacaac cttctcagtc actttcactc      60
```

-continued

```
acctgcactg tcactggcta ctccatcacc ggtggttata gctggcactg gatccggcag    120
tttccaggaa acaaactgga atggatgggc tacatccact acagtggtta cactgacttc    180
aacccctctc tcaaaactcg aatctctatc actcgagaca catccaagaa ccagttcttc    240
ctgcagttga attctgtgac tactgaagac acagccacat attactgtgc aagaaaagat    300
ccgtccgacg gatttcctta ctggggccaa gggactctgg tcactgtctc tgca          354
```

<210> SEQ ID NO 22
<211> LENGTH: 118
<212> TYPE: PRT
<213> ORGANISM: Artificial Sequence
<220> FEATURE:
<223> OTHER INFORMATION: Variable heavy chain sequence of murine 15C1
      antibody

<400> SEQUENCE: 22

Asp Val Gln Leu Gln Glu Ser Gly Pro Asp Leu Ile Gln Pro Ser Gln
1               5                   10                  15

Ser Leu Ser Leu Thr Cys Thr Val Thr Gly Tyr Ser Ile Thr Gly Gly
            20                  25                  30

Tyr Ser Trp His Trp Ile Arg Gln Phe Pro Gly Asn Lys Leu Glu Trp
        35                  40                  45

Met Gly Tyr Ile His Tyr Ser Gly Tyr Thr Asp Phe Asn Pro Ser Leu
    50                  55                  60

Lys Thr Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Arg Lys Asp Pro Ser Asp Gly Phe Pro Tyr Trp Gly Gln Gly Thr
            100                 105                 110

Leu Val Thr Val Ser Ala
        115

<210> SEQ ID NO 23
<211> LENGTH: 6
<212> TYPE: PRT
<213> ORGANISM: Artificial Sequence
<220> FEATURE:
<223> OTHER INFORMATION: Variable heavy chain CDR1 sequence of murine
      15C1 antibody

<400> SEQUENCE: 23

Gly Gly Tyr Ser Trp His
1               5

<210> SEQ ID NO 24
<211> LENGTH: 16
<212> TYPE: PRT
<213> ORGANISM: Artificial Sequence
<220> FEATURE:
<223> OTHER INFORMATION: Variable heavy chain CDR2 sequence of murine
      15C1 antibody

<400> SEQUENCE: 24

Tyr Ile His Tyr Ser Gly Tyr Thr Asp Phe Asn Pro Ser Leu Lys Thr
1               5                   10                  15

<210> SEQ ID NO 25
<211> LENGTH: 9
<212> TYPE: PRT
<213> ORGANISM: Artificial Sequence
<220> FEATURE:
<223> OTHER INFORMATION: Variable heavy chain CDR3 sequence of murine 15C1 antibody

<400> SEQUENCE: 25

Lys Asp Pro Ser Asp Gly Phe Pro Tyr
1               5

<210> SEQ ID NO 26
<211> LENGTH: 321
<212> TYPE: DNA
<213> ORGANISM: Artificial Sequence
<220> FEATURE:
<223> OTHER INFORMATION: Variable light chain sequence of murine 15C1
      antibody

<400> SEQUENCE: 26
gacattgtga tgacccagtc tccagccacc ctgtctgtga ctccaggtga tagagtctct      60
ctttcctgca gggccagcca gagtatcagc gaccacttac actggtatca acaaaaatca     120
catgagtctc cacggcttct catcaaatat gcttcccatg ccatttctgg gatcccctcc     180
aggttcagtg gcagtggatc aggacagat ttcactctca gcatcaaaag tgtggaacct      240
gaagatattg gggtgtatta ctgtcaaaat ggtcacagtt ttccgctcac gttcggtgct     300
gggaccaagc tggagctgaa a                                               321

<210> SEQ ID NO 27
<211> LENGTH: 107
<212> TYPE: PRT
<213> ORGANISM: Artificial Sequence
<220> FEATURE:
<223> OTHER INFORMATION: Variable light chain sequence of murine 15C1
      antibody

<400> SEQUENCE: 27

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp His
                20                  25                  30

Leu His Trp Tyr Gln Gln Lys Ser His Glu Ser Pro Arg Leu Leu Ile
            35                  40                  45

Lys Tyr Ala Ser His Ala Ile Ser Gly Ile Pro Ser Arg Phe Ser Gly
    50                  55                  60

Ser Gly Ser Gly Thr Asp Phe Thr Leu Ser Ile Lys Ser Val Glu Pro
65                  70                  75                  80

Glu Asp Ile Gly Val Tyr Tyr Cys Gln Asn Gly His Ser Phe Pro Leu
                85                  90                  95

Thr Phe Gly Ala Gly Thr Lys Leu Glu Leu Lys
            100                 105

<210> SEQ ID NO 28
<211> LENGTH: 11
<212> TYPE: PRT
<213> ORGANISM: Artificial Sequence
<220> FEATURE:
<223> OTHER INFORMATION: Variable light chain CDR1 sequence of murine
      15C1 antibody

<400> SEQUENCE: 28

Arg Ala Ser Gln Ser Ile Ser Asp His Leu His
1               5                   10

<210> SEQ ID NO 29
<211> LENGTH: 7
<212> TYPE: PRT

```
<213> ORGANISM: Artificial Sequence
<220> FEATURE:
<223> OTHER INFORMATION: Variable light chain CDR2 sequence of murine
      15C1 antibody

<400> SEQUENCE: 29

Tyr Ala Ser His Ala Ile Ser
1               5

<210> SEQ ID NO 30
<211> LENGTH: 9
<212> TYPE: PRT
<213> ORGANISM: Artificial Sequence
<220> FEATURE:
<223> OTHER INFORMATION: Variable light chain CDR3 sequence of murine
      15C1 antibody

<400> SEQUENCE: 30

Gln Asn Gly His Ser Phe Pro Leu Thr
1               5

<210> SEQ ID NO 31
<211> LENGTH: 363
<212> TYPE: DNA
<213> ORGANISM: Artificial Sequence
<220> FEATURE:
<223> OTHER INFORMATION: Variable heavy chain sequence of murine 7E3
      antibody

<400> SEQUENCE: 31
caggttactc tgaaagagtc tggccctggg atattgcagc cctcccagac cctcagtctg      60
acttgttctt tctctgggtt ttcactgacc acttataata taggagtagg ctggattcgt     120
cagccttcag ggaagggtct ggagtggctg gcacacattt ggtggaatga ataatttac      180 tataatacag tccttaagag ccgactcaca ttctccaagg atacctccaa caaccaggtt     240
ttcctcaaga tcgccagtgt ggacattgca gatactgcca catattactg tattcgaatg     300
gctgagggaa ggtacgacgc tatggactac tggggtcaag aacctcagt caccgtctcc     360 tca                                                                   363

<210> SEQ ID NO 32
<211> LENGTH: 121
<212> TYPE: PRT
<213> ORGANISM: Artificial Sequence
<220> FEATURE:
<223> OTHER INFORMATION: Variable heavy chain sequence of murine 7E3
      antibody

<400> SEQUENCE: 32

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Thr Thr Tyr
                20                  25                  30

Asn Ile Gly Val Gly Trp Ile Arg Gln Pro Ser Gly Lys Gly Leu Glu
            35                  40                  45

Trp Leu Ala His Ile Trp Trp Asn Asp Asn Ile Tyr Tyr Asn Thr Val
        50                  55                  60

Leu Lys Ser Arg Leu Thr Phe Ser Lys Asp Thr Ser Asn Asn Gln Val
65                  70                  75                  80

Phe Leu Lys Ile Ala Ser Val Asp Ile Ala Asp Thr Ala Thr Tyr Tyr
                85                  90                  95

Cys Ile Arg Met Ala Glu Gly Arg Tyr Asp Ala Met Asp Tyr Trp Gly
            100                 105                 110
```

Gln Gly Thr Ser Val Thr Val Ser Ser
        115                 120

<210> SEQ ID NO 33
<211> LENGTH: 7
<212> TYPE: PRT
<213> ORGANISM: Artificial Sequence
<220> FEATURE:
<223> OTHER INFORMATION: Variable heavy chain CDR1 sequence of murine
      7E3 antibody

<400> SEQUENCE: 33

Thr Tyr Asn Ile Gly Val Gly
1               5

<210> SEQ ID NO 34
<211> LENGTH: 16
<212> TYPE: PRT
<213> ORGANISM: Artificial Sequence
<220> FEATURE:
<223> OTHER INFORMATION: Variable heavy chain CDR2 sequence of murine
      7E3 antibody

<400> SEQUENCE: 34

His Ile Trp Trp Asn Asp Asn Ile Tyr Tyr Asn Thr Val Leu Lys Ser
1               5                   10                  15

<210> SEQ ID NO 35
<211> LENGTH: 11
<212> TYPE: PRT
<213> ORGANISM: Artificial Sequence
<220> FEATURE:
<223> OTHER INFORMATION: Variable heavy chain CDR3 sequence of murine
      7E3 antibody

<400> SEQUENCE: 35

Met Ala Glu Gly Arg Tyr Asp Ala Met Asp Tyr
1               5                   10

<210> SEQ ID NO 36
<211> LENGTH: 324
<212> TYPE: DNA
<213> ORGANISM: Artificial Sequence
<220> FEATURE:
<223> OTHER INFORMATION: Variable light chain sequence of murine 7E3
      antibody

<400> SEQUENCE: 36
gctatccaga tgacacagag tacatcctcc ctgtctgcct ctctgggaga cagagtcacc        60
atcaattgca gggcaagtca ggacatcacc aattatttaa attggtatca gcagaaacca      120
gatggaactg tcagactcct gatctattat acatcaaaat tacactcagg agccccatca      180
aggttcagtg gccgtgggtc tggaacagat tattctctca ccattagtaa cctggagcaa      240
gaggatattg ccacttactt tgccaacag ggtaatacgt ttccgtggac gttcggtgga      300
ggcaccaaac tggaaatcaa acgt                                              324

<210> SEQ ID NO 37
<211> LENGTH: 108
<212> TYPE: PRT
<213> ORGANISM: Artificial Sequence
<220> FEATURE:
<223> OTHER INFORMATION: Variable light chain sequence of murine 7E3
      antibody

<400> SEQUENCE: 37

```
Ala Ile Gln Met Thr Gln Ser Thr Ser Ser Leu Ser Ala Ser Leu Gly
1               5                   10                  15

Asp Arg Val Thr Ile Asn Cys Arg Ala Ser Gln Asp Ile Thr Asn Tyr
            20                  25                  30

Leu Asn Trp Tyr Gln Lys Pro Asp Gly Thr Val Arg Leu Leu Ile
        35                  40                  45

Tyr Tyr Thr Ser Lys Leu His Ser Gly Ala Pro Ser Arg Phe Ser Gly
    50                  55                  60

Arg Gly Ser Gly Thr Asp Tyr Ser Leu Thr Ile Ser Asn Leu Glu Gln
65              70                  75                  80

Glu Asp Ile Ala Thr Tyr Phe Cys Gln Gln Gly Asn Thr Phe Pro Trp
                85                  90                  95

Thr Phe Gly Gly Gly Thr Lys Leu Glu Ile Lys Arg
            100                 105
```

<210> SEQ ID NO 38
<211> LENGTH: 11
<212> TYPE: PRT
<213> ORGANISM: Artificial Sequence
<220> FEATURE:
<223> OTHER INFORMATION: Variable light chain CDR1 sequence of murine
      7E3 antibody

<400> SEQUENCE: 38

```
Arg Ala Ser Gln Asp Ile Thr Asn Tyr Leu Asn
1               5                   10
```

<210> SEQ ID NO 39
<211> LENGTH: 7
<212> TYPE: PRT
<213> ORGANISM: Artificial Sequence
<220> FEATURE:
<223> OTHER INFORMATION: Variable light chain CDR2 sequence of murine
      7E3 antibody

<400> SEQUENCE: 39

```
Tyr Thr Ser Lys Leu His Ser
1               5
```

<210> SEQ ID NO 40
<211> LENGTH: 9
<212> TYPE: PRT
<213> ORGANISM: Artificial Sequence
<220> FEATURE:
<223> OTHER INFORMATION: Variable light chain CDR3 sequence of murine
      7E3 antibody

<400> SEQUENCE: 40

```
Gln Gln Gly Asn Thr Phe Pro Trp Thr
1               5
```

<210> SEQ ID NO 41
<211> LENGTH: 118
<212> TYPE: PRT
<213> ORGANISM: Artificial Sequence
<220> FEATURE:
<223> OTHER INFORMATION: Variable heavy chain sequence of human 15C1
      antibody (version 4-28)
<220> FEATURE:
<221> NAME/KEY: MISC_FEATURE
<222> LOCATION: (30)..(30)
<223> OTHER INFORMATION: wherein Xaa is Thr or Ser
<220> FEATURE:
<221> NAME/KEY: MISC_FEATURE
<222> LOCATION: (49)..(49)
<223> OTHER INFORMATION: wherein Xaa is Ile or Met
<220> FEATURE:

```
<221> NAME/KEY: MISC_FEATURE
<222> LOCATION: (68)..(68)
<223> OTHER INFORMATION: wherein Xaa is Val or Ile
<220> FEATURE:
<221> NAME/KEY: MISC_FEATURE
<222> LOCATION: (70)..(70)
<223> OTHER INFORMATION: wherein Xaa is Met or Ile

<400> SEQUENCE: 41
```

| Gln | Val | Gln | Leu | Gln | Glu | Ser | Gly | Pro | Gly | Leu | Val | Lys | Pro | Ser | Asp |
|---|---|---|---|---|---|---|---|---|---|---|---|---|---|---|---|
| 1 | | | | 5 | | | | | 10 | | | | | 15 | |

| Thr | Leu | Ser | Leu | Thr | Cys | Ala | Val | Ser | Gly | Tyr | Ser | Ile | Xaa | Gly | Gly |
|---|---|---|---|---|---|---|---|---|---|---|---|---|---|---|---|
| | | | 20 | | | | | 25 | | | | | 30 | | |

| Tyr | Ser | Trp | His | Trp | Ile | Arg | Gln | Pro | Pro | Gly | Lys | Gly | Leu | Glu | Trp |
|---|---|---|---|---|---|---|---|---|---|---|---|---|---|---|---|
| | | | 35 | | | | | 40 | | | | | 45 | | |

| Xaa | Gly | Tyr | Ile | His | Tyr | Ser | Gly | Tyr | Thr | Asp | Phe | Asn | Pro | Ser | Leu |
|---|---|---|---|---|---|---|---|---|---|---|---|---|---|---|---|
| | 50 | | | | | 55 | | | | | 60 | | | | |

| Lys | Thr | Arg | Xaa | Thr | Xaa | Ser | Arg | Asp | Thr | Ser | Lys | Asn | Gln | Phe | Ser |
|---|---|---|---|---|---|---|---|---|---|---|---|---|---|---|---|
| 65 | | | | | 70 | | | | | 75 | | | | | 80 |

| Leu | Lys | Leu | Ser | Ser | Val | Thr | Ala | Val | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

| Ala | Arg | Lys | Asp | Pro | Ser | Asp | Gly | Phe | Pro | Tyr | Trp | Gly | Gln | Gly | Thr |
|---|---|---|---|---|---|---|---|---|---|---|---|---|---|---|---|
| | | | 100 | | | | | 105 | | | | | 110 | | |

| Leu | Val | Thr | Val | Ser | Ser |
|---|---|---|---|---|---|
| | | | 115 | | |

```
<210> SEQ ID NO 42
<211> LENGTH: 118
<212> TYPE: PRT
<213> ORGANISM: Artificial Sequence
<220> FEATURE:
<223> OTHER INFORMATION: Variable heavy chain sequence of human 15C1
      antibody (version 3-66)
<220> FEATURE:
<221> NAME/KEY: MISC_FEATURE
<222> LOCATION: (24)..(24)
<223> OTHER INFORMATION: wherein Xaa is Ala or Val
<220> FEATURE:
<221> NAME/KEY: MISC_FEATURE
<222> LOCATION: (49)..(49)
<223> OTHER INFORMATION: wherein Xaa is Val or Met
<220> FEATURE:
<221> NAME/KEY: MISC_FEATURE
<222> LOCATION: (79)..(79)
<223> OTHER INFORMATION: wherein Xaa is Leu or Phe

<400> SEQUENCE: 42
```

| Glu | Val | Gln | Leu | Val | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Xaa | Ser | Gly | Tyr | Ser | Ile | Thr | Gly | Gly |
|---|---|---|---|---|---|---|---|---|---|---|---|---|---|---|---|
| | | | 20 | | | | | 25 | | | | | 30 | | |

| Tyr | Ser | Trp | His | Trp | Val | Arg | Gln | Ala | Pro | Gly | Lys | Gly | Leu | Glu | Trp |
|---|---|---|---|---|---|---|---|---|---|---|---|---|---|---|---|
| | | | 35 | | | | | 40 | | | | | 45 | | |

| Xaa | Ser | Tyr | Ile | His | Tyr | Ser | Gly | Tyr | Thr | Asp | Phe | Asn | Pro | Ser | Leu |
|---|---|---|---|---|---|---|---|---|---|---|---|---|---|---|---|
| | 50 | | | | | 55 | | | | | 60 | | | | |

| Lys | Thr | Arg | Phe | Thr | Ile | Ser | Arg | Asp | Asn | Ser | Lys | Asn | Thr | Xaa | Tyr |
|---|---|---|---|---|---|---|---|---|---|---|---|---|---|---|---|
| 65 | | | | | 70 | | | | | 75 | | | | | 80 |

| Leu | Gln | Met | Asn | Ser | Leu | Arg | Ala | Glu | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

| Ala | Arg | Lys | Asp | Pro | Ser | Asp | Gly | Phe | Pro | Tyr | Trp | Gly | Gln | Gly | Thr |
|---|---|---|---|---|---|---|---|---|---|---|---|---|---|---|---|
| | | | 100 | | | | | 105 | | | | | 110 | | |

| Leu | Val | Thr | Val | Ser | Ser |
|---|---|---|---|---|---|
| | | | 115 | | |

```
<210> SEQ ID NO 43
<211> LENGTH: 107
<212> TYPE: PRT
<213> ORGANISM: Artificial Sequence
<220> FEATURE:
<223> OTHER INFORMATION: Variable light chain sequence of human 15C1
      antibody (version L6)
<220> FEATURE:
<221> NAME/KEY: MISC_FEATURE
<222> LOCATION: (49)..(49)
<223> OTHER INFORMATION: wherein Xaa is Lys or Tyr

<400> SEQUENCE: 43

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Asp His
            20                  25                  30

Leu His Trp Tyr Gln Gln Lys Pro Gly Gln Ala Pro Arg Leu Leu Ile
        35                  40                  45

Xaa Tyr Ala Ser His Ala Ile Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Asn Gly His Ser Phe Pro Leu
                85                  90                  95

Thr Phe Gly Gly Gly Thr Lys Val Glu Ile Lys
            100                 105

<210> SEQ ID NO 44
<211> LENGTH: 107
<212> TYPE: PRT
<213> ORGANISM: Artificial Sequence
<220> FEATURE:
<223> OTHER INFORMATION: Variable light chain sequence of human 15C1
      antibody (version A26)

<400> SEQUENCE: 44

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Ser Asp His
            20                  25                  30

Leu His Trp Tyr Gln Gln Lys Pro Asp Gln Ser Pro Lys Leu Leu Ile
        35                  40                  45

Lys Tyr Ala Ser His Ala Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Asn Gly His Ser Phe Pro Leu
                85                  90                  95

Thr Phe Gly Gly Gly Thr Lys Val Glu Ile Lys
            100                 105

<210> SEQ ID NO 45
<211> LENGTH: 120
<212> TYPE: PRT
<213> ORGANISM: Artificial Sequence
<220> FEATURE:
<223> OTHER INFORMATION: Variable heavy chain sequence of human 18H10
      antibody (version 1-69)
<220> FEATURE:
<221> NAME/KEY: MISC_FEATURE
<222> LOCATION: (48)..(48)
```

```
<223> OTHER INFORMATION: wherein Xaa is Met or Ile
<220> FEATURE:
<221> NAME/KEY: MISC_FEATURE
<222> LOCATION: (74)..(74)
<223> OTHER INFORMATION: wherein Xaa is Lys or Thr
<220> FEATURE:
<221> NAME/KEY: MISC_FEATURE
<222> LOCATION: (81)..(81)
<223> OTHER INFORMATION: wherein Xaa is Met or Leu

<400> SEQUENCE: 45

Gln Val Gln Leu Val Gln Ser Gly Ala Glu Val Lys Lys Pro Gly Ser
1               5                   10                  15

Ser Val Lys Val Ser Cys Lys Ala Ser Gly Phe Asn Ile Lys Asp Ser
            20                  25                  30

Tyr Ile His Trp Val Arg Gln Ala Pro Gly Gln Gly Leu Glu Trp Xaa
        35                  40                  45

Gly Trp Thr Asp Pro Glu Asn Val Asn Ser Ile Tyr Asp Pro Arg Phe
    50                  55                  60

Gln Gly Arg Val Thr Ile Thr Ala Asp Xaa Ser Thr Ser Thr Ala Tyr
65                  70                  75                  80

Xaa Glu Leu Ser Ser Leu Arg Ser Glu Asp Thr Ala Val Tyr Tyr Cys
                85                  90                  95

Ala Arg Gly Tyr Asn Gly Val Tyr Tyr Ala Met Asp Tyr Trp Gly Gln
            100                 105                 110

Gly Thr Thr Val Thr Val Ser Ser
        115                 120

<210> SEQ ID NO 46
<211> LENGTH: 106
<212> TYPE: PRT
<213> ORGANISM: Artificial Sequence
<220> FEATURE:
<223> OTHER INFORMATION: Variable light chain sequence of human 18H10
      antibody (version L6)
<220> FEATURE:
<221> NAME/KEY: MISC_FEATURE
<222> LOCATION: (70)..(70)
<223> OTHER INFORMATION: wherein Xaa is Phe or Tyr

<400> SEQUENCE: 46

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ile Tyr Met
            20                  25                  30

His Trp Tyr Gln Gln Lys Pro Gly Gln Ala Pro Arg Leu Leu Ile Tyr
        35                  40                  45

Arg Thr Tyr Asn Leu Ala Ser Gly Ile Pro Ala Arg Phe Ser Gly Ser
    50                  55                  60

Gly Ser Gly Thr Asp Xaa Thr Leu Thr Ile Ser Ser Leu Glu Pro Glu
65                  70                  75                  80

Asp Phe Ala Val Tyr Tyr Cys His Gln Trp Ser Ser Phe Pro Tyr Thr
                85                  90                  95

Phe Gly Gln Gly Thr Lys Val Glu Ile Lys
            100                 105

<210> SEQ ID NO 47
<211> LENGTH: 121
<212> TYPE: PRT
<213> ORGANISM: Artificial Sequence
<220> FEATURE:
<223> OTHER INFORMATION: Variable heavy chain sequence of human 7E3
      antibody (version 2-70)
```

```
<220> FEATURE:
<221> NAME/KEY: MISC_FEATURE
<222> LOCATION: (30)..(30)
<223> OTHER INFORMATION: wherein Xaa is Ser or Thr
<220> FEATURE:
<221> NAME/KEY: MISC_FEATURE
<222> LOCATION: (71)..(71)
<223> OTHER INFORMATION: wherein Xaa is Ile or Phe
<220> FEATURE:
<221> NAME/KEY: MISC_FEATURE
<222> LOCATION: (98)..(98)
<223> OTHER INFORMATION: wherein Xaa is Ile or Ala

<400> SEQUENCE: 47

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Xaa Thr Tyr
            20                  25                  30

Asn Ile Gly Val Gly Trp Ile Arg Gln Pro Pro Gly Lys Ala Leu Glu
        35                  40                  45

Trp Leu Ala His Ile Trp Trp Asn Asp Asn Ile Tyr Tyr Asn Thr Val
    50                  55                  60

Leu Lys Ser Arg Leu Thr Xaa Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Xaa Arg Met Ala Glu Gly Arg Tyr Asp Ala Met Asp Tyr Trp Gly
            100                 105                 110

Gln Gly Thr Leu Val Thr Val Ser Ser
        115                 120

<210> SEQ ID NO 48
<211> LENGTH: 121
<212> TYPE: PRT
<213> ORGANISM: Artificial Sequence
<220> FEATURE:
<223> OTHER INFORMATION: Variable heavy chain sequence of human 7E3
      antibody (version 3-66)
<220> FEATURE:
<221> NAME/KEY: MISC_FEATURE
<222> LOCATION: (24)..(24)
<223> OTHER INFORMATION: wherein Xaa is Phe or Ala
<220> FEATURE:
<221> NAME/KEY: MISC_FEATURE
<222> LOCATION: (50)..(50)
<223> OTHER INFORMATION: wherein Xaa is Val or Leu
<220> FEATURE:
<221> NAME/KEY: MISC_FEATURE
<222> LOCATION: (71)..(71)
<223> OTHER INFORMATION: wherein Xaa is Ile or Phe
<220> FEATURE:
<221> NAME/KEY: MISC_FEATURE
<222> LOCATION: (73)..(73)
<223> OTHER INFORMATION: wherein Xaa is Lys or Arg
<220> FEATURE:
<221> NAME/KEY: MISC_FEATURE
<222> LOCATION: (80)..(80)
<223> OTHER INFORMATION: wherein Xaa is Leu or Val
<220> FEATURE:
<221> NAME/KEY: MISC_FEATURE
<222> LOCATION: (98)..(98)
<223> OTHER INFORMATION: wherein Xaa is Ile or Ala

<400> SEQUENCE: 48

Glu Val Gln Leu Val Glu Ser Gly Gly Gly Leu Val Gln Pro Gly Gly
1               5                   10                  15

Ser Leu Arg Leu Ser Cys Ala Xaa Ser Gly Phe Ser Leu Thr Thr Tyr
            20                  25                  30
```

```
Asn Ile Gly Val Gly Trp Val Arg Gln Ala Pro Gly Lys Gly Leu Glu
             35                  40                  45

Trp Xaa Ser His Ile Trp Trp Asn Asp Asn Ile Tyr Tyr Asn Thr Val
     50                  55                  60

Leu Lys Ser Arg Leu Thr Xaa Ser Xaa Asp Asn Ser Lys Asn Thr Xaa
 65                  70                  75                  80

Tyr Leu Gln Met Asn Ser Leu Arg Ala Glu Asp Thr Ala Val Tyr Tyr
                 85                  90                  95

Cys Xaa Arg Met Ala Glu Gly Arg Tyr Asp Ala Met Asp Tyr Trp Gly
        100                 105                 110

Gln Gly Thr Leu Val Thr Val Ser Ser
        115                 120

<210> SEQ ID NO 49
<211> LENGTH: 107
<212> TYPE: PRT
<213> ORGANISM: Artificial Sequence
<220> FEATURE:
<223> OTHER INFORMATION: Variable light chain sequence of human 7E3
      antibody (version L19)
<220> FEATURE:
<221> NAME/KEY: MISC_FEATURE
<222> LOCATION: (71)..(71)
<223> OTHER INFORMATION: wherein Xaa is Phe or Tyr
<220> FEATURE:
<221> NAME/KEY: MISC_FEATURE
<222> LOCATION: (87)..(87)
<223> OTHER INFORMATION: wherein Xaa is Tyr or Phe

<400> SEQUENCE: 49

Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Asp Ile Thr Asn Tyr
             20                  25                  30

Leu Asn Trp Tyr Gln Gln Lys Pro Gly Lys Ala Pro Lys Leu Leu Ile
         35                  40                  45

Tyr Tyr Thr Ser Lys Leu His Ser Gly Val Pro Ser Arg Phe Ser Gly
     50                  55                  60

Ser Gly Ser Gly Thr Asp Xaa Thr Leu Thr Ile Ser Ser Leu Gln Pro
 65                  70                  75                  80

Glu Asp Phe Ala Thr Tyr Xaa Cys Gln Gln Gly Asn Thr Phe Pro Trp
                 85                  90                  95

Thr Phe Gly Gly Gly Thr Lys Val Glu Ile Lys
            100                 105

<210> SEQ ID NO 50
<211> LENGTH: 639
<212> TYPE: DNA
<213> ORGANISM: Artificial Sequence
<220> FEATURE:
<223> OTHER INFORMATION: Variable heavy chain sequence of murine 28C5
      antibody

<400> SEQUENCE: 50 cccccctcg agcttcagca gtcaggacct ggcctggtga aaccttctca gtctctgtcc     60
ctcacctgca ctgtcactgg ctactcaatc accagtgatt ctgcctggaa ctggatccgg   120
cagtttccag gaaacagact ggagtggatg ggctacataa gctacagtgg tagcactagc   180
tacaacccat ctctcaaaag tcgaatctct atcactcgag acacatccaa gaaccagttc   240
ttcctgcagt tgaattcggt gactactgag gacacagcca catattactg tgtaagaggg   300
ctccggtttg cttactgggg aaggggact ctggtcactg tctctgcagc aaaaacaacc   360
```

```
cccccctctg tctatccact gcccctgga tctgctgccc aaactaactc catggtgacc      420
ctgggatgcc tggtcaaggc ctatttccct gagccagtga cagtgacctg gaactctgga     480
tccctgtcca gcggttggca caccttccca gctgtcctgc agtctgacct ctacactctg     540
agcagctcag tgactgtccc ctccagcacc tggcccagcg agaccgtcac ctgcaacgtt     600
gcccacccgg ccagcagcac caaggtggac aagaaaatt                            639
```

```
<210> SEQ ID NO 51
<211> LENGTH: 213
<212> TYPE: PRT
<213> ORGANISM: Artificial Sequence
<220> FEATURE:
<223> OTHER INFORMATION: Variable heavy chain sequence of murine 28C5
      antibody

<400> SEQUENCE: 51
```

```
Pro Pro Leu Glu Leu Gln Gln Ser Gly Pro Gly Leu Val Lys Pro Ser
1               5                   10                  15

Gln Ser Leu Ser Leu Thr Cys Thr Val Thr Gly Tyr Ser Ile Thr Ser
            20                  25                  30

Asp Ser Ala Trp Asn Trp Ile Arg Gln Phe Pro Gly Asn Arg Leu Glu
        35                  40                  45

Trp Met Gly Tyr Ile Ser Tyr Ser Gly Ser Thr Ser Tyr Asn Pro Ser
    50                  55                  60

Leu Lys Ser Arg Ile Ser Ile Thr Arg Asp Thr Ser Lys Asn Gln Phe
65                  70                  75                  80

Phe Leu Gln Leu Asn Ser Val Thr Thr Glu Asp Thr Ala Thr Tyr Tyr
                85                  90                  95

Cys Val Arg Gly Leu Arg Phe Ala Tyr Trp Gly Lys Gly Thr Leu Val
            100                 105                 110

Thr Val Ser Ala Ala Lys Thr Thr Pro Pro Ser Val Tyr Pro Leu Pro
        115                 120                 125

Pro Gly Ser Ala Ala Gln Thr Asn Ser Met Val Thr Leu Gly Cys Leu
    130                 135                 140

Val Lys Ala Tyr Phe Pro Glu Pro Val Thr Val Thr Trp Asn Ser Gly
145                 150                 155                 160

Ser Leu Ser Ser Gly Trp His Thr Phe Pro Ala Val Leu Gln Ser Asp
                165                 170                 175

Leu Tyr Thr Leu Ser Ser Ser Val Thr Val Pro Ser Ser Thr Trp Pro
            180                 185                 190

Ser Glu Thr Val Thr Cys Asn Val Ala His Pro Ala Ser Ser Thr Lys
        195                 200                 205

Val Asp Lys Lys Ile
    210
```

```
<210> SEQ ID NO 52
<211> LENGTH: 645
<212> TYPE: DNA
<213> ORGANISM: Artificial Sequence
<220> FEATURE:
<223> OTHER INFORMATION: Variable light chain sequence of murine 28C5
      antibody

<400> SEQUENCE: 52
```

```
atgacacagt ctccagcttc tttggctgtg tctctagggc agagggcccc atatccttgc      60
agagccagtg aaagtgttga tagttatgtc aatagttttc tccactggta ccagcagaaa     120
ccaggacagc cacccaaact cctcatctat cgtgcatcca acctacaatc tgggatccct     180
```

```
gccaggttca gtggcagtgg gtctaggaca gacttcaccc tcaccattaa tcctgtggag    240
gctgatgatg ttgcaaccta ttactgtcag caaagtaatg aggatccgac gacgtcggga    300
gggggcacca agctggaaat aaaacgggct gatgctgcac cccttgtatc catcttcccc    360
ccatccagtg agcagttaac atctggaggt gcctcagttg tgtgcttctt gaacaacttc    420 tacccc aaag acatcaatgt caagtggaag attgatgtca gtgaacgaca aaatggcgtc    480
ctgaacagtt ggactgatca ggacagcaaa gacagcacct acagcatgag cagcaccctc    540
acgttgacca aggacgagta tgaacgacat aacagctata cctgtgaggc cactcacaag    600
acatcaactt cacccattgt caagagcttc aacaggaatg agtgt              645
```

<210> SEQ ID NO 53
<211> LENGTH: 215
<212> TYPE: PRT
<213> ORGANISM: Artificial Sequence
<220> FEATURE:
<223> OTHER INFORMATION: Variable light chain sequence of murine 28C5
      antibody

<400> SEQUENCE: 53

```
Met Thr Gln Ser Pro Ala Ser Leu Ala Val Ser Leu Gly Gln Arg Ala
1               5                   10                  15

Pro Tyr Pro Cys Arg Ala Ser Glu Ser Val Asp Ser Tyr Val Asn Ser
            20                  25                  30

Phe Leu His Trp Tyr Gln Gln Lys Pro Gly Gln Pro Pro Lys Leu Leu
        35                  40                  45

Ile Tyr Arg Ala Ser Asn Leu Gln Ser Gly Ile Pro Ala Arg Phe Ser
    50                  55                  60

Gly Ser Gly Ser Arg Thr Asp Phe Thr Leu Thr Ile Asn Pro Val Glu
65                  70                  75                  80

Ala Asp Asp Val Ala Thr Tyr Tyr Cys Gln Gln Ser Asn Glu Asp Pro
                85                  90                  95

Thr Thr Ser Gly Gly Gly Thr Lys Leu Glu Ile Lys Arg Ala Asp Ala
            100                 105                 110

Ala Pro Leu Val Ser Ile Phe Pro Pro Ser Ser Glu Gln Leu Thr Ser
        115                 120                 125

Gly Gly Ala Ser Val Val Cys Phe Leu Asn Asn Phe Tyr Pro Lys Asp
    130                 135                 140

Ile Asn Val Lys Trp Lys Ile Asp Val Ser Glu Arg Gln Asn Gly Val
145                 150                 155                 160

Leu Asn Ser Trp Thr Asp Gln Asp Ser Lys Asp Ser Thr Tyr Ser Met
                165                 170                 175

Ser Ser Thr Leu Thr Leu Thr Lys Asp Glu Tyr Glu Arg His Asn Ser
            180                 185                 190

Tyr Thr Cys Glu Ala Thr His Lys Thr Ser Thr Ser Pro Ile Val Lys
        195                 200                 205

Ser Phe Asn Arg Asn Glu Cys
    210                 215
```

<210> SEQ ID NO 54
<211> LENGTH: 499
<212> TYPE: DNA
<213> ORGANISM: Artificial Sequence
<220> FEATURE:
<223> OTHER INFORMATION: Variable heavy chain sequence of murine T2.5
      antibody

<400> SEQUENCE: 54

```
atgtcctctc cacagtccct gaagacactg attctaacca tgggatggag ctggatcttt      60
ctcttcctcc tgtcaggaac tgcaggtgtc cactcccagg ttcagctgca gcagtctgga     120
cctgagctgg tgaaccctgg ggcgtcagtg aagttgtcct gcaaggcttc tggcttcacc     180
ttcacaacct acggtataaa ctgggtgaag caggggcctg acagggact tgagtggatt      240 ggatggattt atcctagaga tggtagtact acttcaatga aatttcaag acaaggccg       300 cattgactgt agacacatcc tccagcacag cgtacatgga actccacagc ctgacatctg     360
aagactctgc ggtctatttc tgtgcaagac tgactggtgg acattcctt gactattggg      420 gccagggcac cactctcaca gtctcctcag ccaaacgaca cccccatctg tctatccact     480
ggcccctgga tctgctgcc                                                  499

<210> SEQ ID NO 55
<211> LENGTH: 501
<212> TYPE: DNA
<213> ORGANISM: Artificial Sequence
<220> FEATURE:
<223> OTHER INFORMATION: Variable heavy chain sequence of murine T2.5
      antibody

<400> SEQUENCE: 55
tacaggagag gtgtcaggga cttctgtgac taagattggt accctacctc gacctagaaa      60
gagaaggagg acagtccttg acgtccacag gtgagggtcc aagtcgacgt cgtcagacct     120
ggactcgacc acttgggacc ccgcagtcac ttcaacagga cgttccgaag accgaagtgg     180
aagtgttgga tgccatattt gacccacttc gtccccggac ctgtccctga actcacctaa     240
cctacctaaa taggatctct accatcatga ttgaagttac tcttaaagtt cctgttccgg     300
cgtaactgac atctgtgtag gaggtcgtgt cgcatgtacc ttgaggtgtc ggactgtaga     360
cttctgagac gccagataaa gacacgttct gactgaccac cctgtaagga actgataacc     420
ccggtcccgt ggtgagagtg tcagaggagt cggttttgct gtgggggtag acagataggt     480
gaccggggac ctagacgacg g                                               501

<210> SEQ ID NO 56
<211> LENGTH: 167
<212> TYPE: PRT
<213> ORGANISM: Artificial Sequence
<220> FEATURE:
<223> OTHER INFORMATION: Variable heavy chain sequence of murine T2.5
      antibody

<400> SEQUENCE: 56

Met Ser Ser Pro Gln Ser Leu Lys Thr Leu Ile Leu Thr Met Gly Trp
1               5                   10                  15

Ser Trp Ile Phe Leu Phe Leu Leu Ser Gly Thr Ala Gly Val His Ser
            20                  25                  30

Gln Val Gln Leu Gln Gln Ser Gly Pro Glu Leu Val Asn Pro Gly Ala
        35                  40                  45

Ser Val Lys Leu Ser Cys Lys Ala Ser Gly Phe Thr Phe Thr Thr Tyr
    50                  55                  60

Gly Ile Asn Trp Val Lys Gln Gly Pro Gly Gln Gly Leu Glu Trp Ile
65                  70                  75                  80

Gly Trp Ile Tyr Pro Arg Asp Gly Ser Thr Asn Phe Asn Glu Asn Phe
                85                  90                  95

Lys Asp Lys Ala Ala Leu Thr Val Asp Thr Ser Ser Ser Thr Ala Tyr
            100                 105                 110
```

```
Met Glu Leu His Ser Leu Thr Ser Glu Asp Ser Ala Val Tyr Phe Cys
            115                 120                 125

Ala Arg Leu Thr Gly Gly Thr Phe Leu Asp Trp Trp Gly Gln Gly Thr
        130                 135                 140

Thr Leu Thr Val Ser Ser Ala Lys Thr Thr Pro Pro Ser Val Tyr Pro
145                 150                 155                 160

Leu Ala Pro Gly Ser Ala Ala
                165

<210> SEQ ID NO 57
<211> LENGTH: 442
<212> TYPE: DNA
<213> ORGANISM: Artificial Sequence
<220> FEATURE:
<223> OTHER INFORMATION: Variable light chain sequence of murine T2.5
      antibody

<400> SEQUENCE: 57
atggagtcag acacactcct gctatgggtg ctgctgctct gggttccagg ctccactggt      60
gacattgtgc tcacccaatc tccagcttct ttggctgtgt ctctagggca gagagccacc     120
atctcctgca gagccagtga aaggttgaat attatgcac aagtttaatg cagtggtacc      180
aacagaaacc aggacagcca cccaaactcc tcatctttgg tgcatccaac gtagaatctg     240
gggtccctgt caggttcagt ggcagtgggt ctgggacaga cttcagcctc aacatccatc     300
ctgtggagga ggatgatatt gtaatgtatt tctgtcagca aagtaggaaa cttccgtgga     360
cgttcggtgg aggcaccaag ctggaaatca acgggctga tgctgcacca actgtatcca     420
tcttcccacc atccagtgag ca                                               442

<210> SEQ ID NO 58
<211> LENGTH: 443
<212> TYPE: DNA
<213> ORGANISM: Artificial Sequence
<220> FEATURE:
<223> OTHER INFORMATION: Variable light chain sequence of murine T2.5
      antibody

<400> SEQUENCE: 58
tacctcagtc tgtgtgagga cgatacccac gacgacgaga cccaaggtcc gaggtgacca      60
ctgtaacacg agtgggttag aggtcgaaga aaccgcacac gagatcccgt ctctcggtgg     120
tagaggacgt ctcggtcact ttcacaactt ataataccgt gttcaaatta cgtcaccatg     180
gttgtctttg gtcctgtcgg tgggtttgag gagtagaaac cacgtaggtt gcatcttaga     240
ccccagggac agtccaagtc accgtcaccc agaccctgtc tgaagtcgga gttgtaggta     300
ggacacctcc tcctactata acattacata aagacagtcg tttcatcctt tgaaggcacc     360
tgcaagccac ctccgtggtt cgacctttag tttgcccgac tacgacgtgg ttgacatagg     420
tagaagggtg gtaggtcact cgt                                              443

<210> SEQ ID NO 59
<211> LENGTH: 147
<212> TYPE: PRT
<213> ORGANISM: Artificial Sequence
<220> FEATURE:
<223> OTHER INFORMATION: Variable light chain sequence of murine T2.5
      antibody

<400> SEQUENCE: 59

Met Glu Ser Asp Thr Leu Leu Leu Trp Val Leu Leu Leu Trp Val Pro
1               5                   10                  15
```

```
Gly Ser Thr Gly Asp Ile Val Leu Thr Gln Ser Pro Ala Ser Leu Ala
            20                  25                  30

Val Ser Leu Gly Gln Arg Ala Thr Ile Ser Cys Arg Ala Ser Glu Ser
        35                  40                  45

Val Glu Tyr Tyr Gly Thr Ser Leu Met Gln Trp Tyr Gln Gln Lys Pro
    50                  55                  60

Gly Gln Pro Pro Lys Leu Leu Ile Phe Gly Ala Ser Asn Val Glu Ser
65                  70                  75                  80

Gly Val Pro Val Arg Phe Ser Gly Ser Gly Ser Gly Thr Asp Phe Ser
                85                  90                  95

Leu Asn Ile His Pro Val Glu Glu Asp Asp Ile Val Met Tyr Phe Cys
            100                 105                 110

Gln Gln Ser Arg Lys Leu Pro Trp Thr Phe Gly Gly Gly Thr Lys Leu
        115                 120                 125

Glu Ile Lys Arg Ala Asp Ala Ala Pro Thr Val Ser Ile Phe Pro Pro
    130                 135                 140

Ser Ser Glu
145

<210> SEQ ID NO 60
<211> LENGTH: 160
<212> TYPE: PRT
<213> ORGANISM: Homo sapiens

<400> SEQUENCE: 60

Met Leu Pro Phe Leu Phe Phe Ser Thr Leu Phe Ser Ser Ile Phe Thr
1               5                   10                  15

Glu Ala Gln Lys Gln Tyr Trp Val Cys Asn Ser Ser Asp Ala Ser Ile
            20                  25                  30

Ser Tyr Thr Tyr Cys Asp Lys Met Gln Tyr Pro Ile Ser Ile Asn Val
        35                  40                  45

Asn Pro Cys Ile Glu Leu Lys Gly Ser Lys Gly Leu Leu His Ile Phe
    50                  55                  60

Tyr Ile Pro Arg Arg Asp Leu Lys Gln Leu Tyr Phe Asn Leu Tyr Ile
65                  70                  75                  80

Thr Val Asn Thr Met Asn Leu Pro Lys Arg Lys Glu Val Ile Cys Arg
                85                  90                  95

Gly Ser Asp Asp Asp Tyr Ser Phe Cys Arg Ala Leu Lys Gly Glu Thr
            100                 105                 110

Val Asn Thr Thr Ile Ser Phe Ser Phe Lys Gly Ile Lys Phe Ser Lys
        115                 120                 125

Gly Lys Tyr Lys Cys Val Val Glu Ala Ile Ser Gly Ser Pro Glu Glu
    130                 135                 140

Met Leu Phe Cys Leu Glu Phe Val Ile Leu His Gln Pro Asn Ser Asn
145                 150                 155                 160

<210> SEQ ID NO 61
<211> LENGTH: 839
<212> TYPE: PRT
<213> ORGANISM: Homo sapiens

<400> SEQUENCE: 61

Met Met Ser Ala Ser Arg Leu Ala Gly Thr Leu Ile Pro Ala Met Ala
1               5                   10                  15

Phe Leu Ser Cys Val Arg Pro Glu Ser Trp Glu Pro Cys Val Glu Val
            20                  25                  30

Val Pro Asn Ile Thr Tyr Gln Cys Met Glu Leu Asn Phe Tyr Lys Ile
```

```
                35                  40                  45
Pro Asp Asn Leu Pro Phe Ser Thr Lys Asn Leu Asp Leu Ser Phe Asn
 50                  55                  60
Pro Leu Arg His Leu Gly Ser Tyr Ser Phe Phe Ser Phe Pro Glu Leu
 65                      70                  75                  80
Gln Val Leu Asp Leu Ser Arg Cys Glu Ile Gln Thr Ile Glu Asp Gly
                     85                  90                  95
Ala Tyr Gln Ser Leu Ser His Leu Ser Thr Leu Ile Leu Thr Gly Asn
                100                 105                 110
Pro Ile Gln Ser Leu Ala Leu Gly Ala Phe Ser Gly Leu Ser Ser Leu
            115                 120                 125
Gln Lys Leu Val Ala Val Glu Thr Asn Leu Ala Ser Leu Glu Asn Phe
130                 135                 140
Pro Ile Gly His Leu Lys Thr Leu Lys Glu Leu Asn Val Ala His Asn
145                 150                 155                 160
Leu Ile Gln Ser Phe Lys Leu Pro Glu Tyr Phe Ser Asn Leu Thr Asn
                    165                 170                 175
Leu Glu His Leu Asp Leu Ser Ser Asn Lys Ile Gln Ser Ile Tyr Cys
                180                 185                 190
Thr Asp Leu Arg Val Leu His Gln Met Pro Leu Leu Asn Leu Ser Leu
            195                 200                 205
Asp Leu Ser Leu Asn Pro Met Asn Phe Ile Gln Pro Gly Ala Phe Lys
210                 215                 220
Glu Ile Arg Leu His Lys Leu Thr Leu Arg Asn Asn Phe Asp Ser Leu
225                 230                 235                 240
Asn Val Met Lys Thr Cys Ile Gln Gly Leu Ala Gly Leu Glu Val His
                    245                 250                 255
Arg Leu Val Leu Gly Glu Phe Arg Asn Glu Gly Asn Leu Glu Lys Phe
                260                 265                 270
Asp Lys Ser Ala Leu Glu Gly Leu Cys Asn Leu Thr Ile Glu Glu Phe
            275                 280                 285
Arg Leu Ala Tyr Leu Asp Tyr Tyr Leu Asp Asp Ile Ile Asp Leu Phe
290                 295                 300
Asn Cys Leu Thr Asn Val Ser Ser Phe Ser Leu Val Ser Val Thr Ile
305                 310                 315                 320
Glu Arg Val Lys Asp Phe Ser Tyr Asn Phe Gly Trp Gln His Leu Glu
                    325                 330                 335
Leu Val Asn Cys Lys Phe Gly Gln Phe Pro Thr Leu Lys Leu Lys Ser
                340                 345                 350
Leu Lys Arg Leu Thr Phe Thr Ser Asn Lys Gly Gly Asn Ala Phe Ser
            355                 360                 365
Glu Val Asp Leu Pro Ser Leu Glu Phe Leu Asp Leu Ser Arg Asn Gly
370                 375                 380
Leu Ser Phe Lys Gly Cys Cys Ser Gln Ser Asp Phe Gly Thr Thr Ser
385                 390                 395                 400
Leu Lys Tyr Leu Asp Leu Ser Phe Asn Gly Val Ile Thr Met Ser Ser
                    405                 410                 415
Asn Phe Leu Gly Leu Glu Gln Leu Glu His Leu Asp Phe Gln His Ser
                420                 425                 430
Asn Leu Lys Gln Met Ser Glu Phe Ser Val Phe Leu Ser Leu Arg Asn
            435                 440                 445
Leu Ile Tyr Leu Asp Ile Ser His Thr His Thr Arg Val Ala Phe Asn
450                 455                 460
```

-continued

```
Gly Ile Phe Asn Gly Leu Ser Ser Leu Glu Val Leu Lys Met Ala Gly
465                 470                 475                 480

Asn Ser Phe Gln Glu Asn Phe Leu Pro Asp Ile Phe Thr Glu Leu Arg
            485                 490                 495

Asn Leu Thr Phe Leu Asp Leu Ser Gln Cys Gln Leu Glu Gln Leu Ser
                500                 505                 510

Pro Thr Ala Phe Asn Ser Leu Ser Ser Leu Gln Val Leu Asn Met Ser
            515                 520                 525

His Asn Asn Phe Phe Ser Leu Asp Thr Phe Pro Tyr Lys Cys Leu Asn
        530                 535                 540

Ser Leu Gln Val Leu Asp Tyr Ser Leu Asn His Ile Met Thr Ser Lys
545                 550                 555                 560

Lys Gln Glu Leu Gln His Phe Pro Ser Ser Leu Ala Phe Leu Asn Leu
                565                 570                 575

Thr Gln Asn Asp Phe Ala Cys Thr Cys Glu His Gln Ser Phe Leu Gln
            580                 585                 590

Trp Ile Lys Asp Gln Arg Gln Leu Leu Val Glu Val Glu Arg Met Glu
        595                 600                 605

Cys Ala Thr Pro Ser Asp Lys Gln Gly Met Pro Val Leu Ser Leu Asn
610                 615                 620

Ile Thr Cys Gln Met Asn Lys Thr Ile Ile Gly Val Ser Val Leu Ser
625                 630                 635                 640

Val Leu Val Val Ser Val Val Ala Val Leu Val Tyr Lys Phe Tyr Phe
                645                 650                 655

His Leu Met Leu Leu Ala Gly Cys Ile Lys Tyr Gly Arg Gly Glu Asn
            660                 665                 670

Ile Tyr Asp Ala Phe Val Ile Tyr Ser Ser Gln Asp Glu Asp Trp Val
        675                 680                 685

Arg Asn Glu Leu Val Lys Asn Leu Glu Glu Gly Val Pro Pro Phe Gln
    690                 695                 700

Leu Cys Leu His Tyr Arg Asp Phe Ile Pro Gly Val Ala Ile Ala Ala
705                 710                 715                 720

Asn Ile Ile His Glu Gly Phe His Lys Ser Arg Lys Val Ile Val Val
                725                 730                 735

Val Ser Gln His Phe Ile Gln Ser Arg Trp Cys Ile Phe Glu Tyr Glu
            740                 745                 750

Ile Ala Gln Thr Trp Gln Phe Leu Ser Ser Arg Ala Gly Ile Ile Phe
        755                 760                 765

Ile Val Leu Gln Lys Val Glu Lys Thr Leu Leu Arg Gln Gln Val Glu
770                 775                 780

Leu Tyr Arg Leu Leu Ser Arg Asn Thr Tyr Leu Glu Trp Glu Asp Ser
785                 790                 795                 800

Val Leu Gly Arg His Ile Phe Trp Arg Arg Leu Arg Lys Ala Leu Leu
                805                 810                 815

Asp Gly Lys Ser Trp Asn Pro Glu Gly Thr Val Gly Thr Gly Cys Asn
            820                 825                 830

Trp Gln Glu Ala Thr Ser Ile
        835
```

What is claimed is:

1. A composition comprising a combination of neutralizing antibodies, wherein said combination of neutralizing antibodies comprises an antibody that immunospecifically binds toll-like receptor 4 (TLR4) and an antibody that immunospecifically binds toll-like receptor 2 (TLR2), wherein the anti-TLR4 antibody is an antibody having a heavy chain variable region comprising the amino acid sequence of SEQ ID NO: 41 and a light chain variable region comprising the amino acid sequence of SEQ ID NO: 44; and wherein the anti-TLR2 antibody comprises a heavy chain variable region comprising the amino acid sequence of SEQ ID NO: 56 and a light chain variable region comprising the amino acid sequence of SEQ ID NO: 59; wherein the anti-TLR4 antibody and the anti-TLR2 antibody are present in an amount that is effective to produce synergistic inhibition of bacterial-induced IL-6 production in a solution comprising whole blood where the bacteria is added to the whole blood solution at a concentration of $10^6$ cfu/ml, as compared to the level of bacterial-induced IL-6 production in the whole blood solution in the absence of the combination of antibodies.

2. The composition of claim 1, wherein said combination of neutralizing antibodies further comprises an antibody that immunospecifically binds MD-2.

3. The composition of claim 1, wherein said combination of neutralizing antibodies further comprises an antibody that immunospecifically binds a toll-like receptor selected from the group consisting of toll-like receptor 1 (TLR1), toll-like receptor 5 (TLR5) and toll-like receptor 6 (TLR6).

4. A composition comprising a combination of antibodies, wherein said combination of antibodies comprises an antibody that immunospecifically binds toll-like receptor 4 (TLR4) and an antibody that immunospecifically binds toll-like receptor 2 (TLR2), wherein the anti-TLR4 antibody is an antibody having a heavy chain variable region comprising the amino acid sequence of SEQ ID NO: 41 and a light chain variable region comprising the amino acid sequence of SEQ ID NO: 44; and wherein the anti-TLR2 antibody comprises a heavy chain variable region comprising the amino acid sequence of SEQ ID NO: 56 and a light chain variable region comprising the amino acid sequence of SEQ ID NO: 59; wherein the anti-TLR4 antibody and the anti-TLR2 antibody are present in an amount that is effective to produce synergistic inhibition of bacterial-induced IL-6 production in a solution comprising whole blood where the bacteria is added to the whole blood solution at a concentration of $10^6$ cfu/ml, as compared to the level of bacterial-induced IL-6 production in the whole blood solution in the absence of the combination of antibodies.

5. The composition of claim 4, wherein said combination of antibodies further comprises an antibody that immunospecifically binds MD-2.

6. The composition of claim 1, wherein said combination of antibodies further comprises an antibody that immunospecifically binds a toll-like receptor selected from the group consisting of toll-like receptor 1 (TLR1), toll-like receptor 5 (TLR5) and toll-like receptor 6 (TLR6).

\* \* \* \* \*